US010543260B2

(12) United States Patent
Steinman et al.

(10) Patent No.: US 10,543,260 B2
(45) Date of Patent: Jan. 28, 2020

(54) REPLACEMENT GENE TOLERIZING VECTORS AND METHODS OF USE THEREOF

(71) Applicant: The Board of Trustees of the Leland Stanford Junior University, Stanford, CA (US)

(72) Inventors: Lawrence Steinman, Stanford, CA (US); Peggy Pui-Kay Ho, Cupertino, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 430 days.

(21) Appl. No.: 15/214,960

(22) Filed: Jul. 20, 2016

(65) Prior Publication Data

US 2017/0021000 A1 Jan. 26, 2017

Related U.S. Application Data

(60) Provisional application No. 62/195,622, filed on Jul. 22, 2015.

(51) Int. Cl.
*A61K 39/00* (2006.01)
*C12N 7/00* (2006.01)
*A61K 48/00* (2006.01)

(52) U.S. Cl.
CPC .............. *A61K 39/001* (2013.01); *C12N 7/00* (2013.01); *A61K 48/00* (2013.01); *A61K 2039/53* (2013.01); *A61K 2039/577* (2013.01); *C12N 2750/14143* (2013.01); *C12N 2750/14171* (2013.01)

(58) Field of Classification Search
CPC .... A61K 39/001; A61K 48/005; A61K 48/00; A61K 2039/53; A61K 2039/577; C12N 7/00; C12N 2750/14122; C12N 2750/14143; C12N 2750/14171; C12N 2800/107
See application file for complete search history.

(56) References Cited

U.S. PATENT DOCUMENTS

| 7,544,669 B2 | 6/2009 | Fontoura et al. |
| 8,748,404 B2 | 6/2014 | Steinman et al. |
| 2009/0208481 A1* | 8/2009 | Steinman ........... A61K 38/4866 424/94.64 |

FOREIGN PATENT DOCUMENTS

WO 2003/045316 A2 6/2003

OTHER PUBLICATIONS

Seto et al., Curr Gene Ther., 12(3): 139-151, Jun. 2012.*
Steinman J InternMed, 267: 441-451, 2010.*
Faust et al., J Clin Invest., 123(7):2994-3001, 2013.*
Ho et al., PNAS 115(30): E9182-E9191, 2018.*
Blake et al., "Function and Genetics of Dystrophin and Dystrophin-Related Proteins in Muscle", Physiol Rev, 2002, pp. 291-329, 82, American Physiological Society, Bethesda, MD.
Boccacccio et al., "Non-coding plasmid DNA induces IFN-y in vivo and suppresses autoimmune encephalomyelitis", International Immunology, 1999, pp. 289-296, vol. 11, No. 2, The Japanese Society for Immunology, Tokyo, Japan.
Bowles et al.,"Phase 1 Gene Therapy for Duchenne Muscular Dystrophy Using a Translational Optimized AAV Vector", Molecular Therapy, Feb. 2012, pp. 443-455, vol. 20, No. 2, The American Society of Gene & Cell Therapy, Milwaukee, WI.
Ehmsen et al., "The dystrophinassociated protein complex", Journal of Cell Science, 2002, pp. 2801-2803 , 115, The Company of Biologists Ltd, Cambridge, United Kingdom.
Ervasti, "Dystrophin, its interactions with other proteins, and implications for muscular dystrophy", Biochimica et Biophysica Acta, 2007, pp. 108-117, 1772, Elsevier, Amsterdam, Netherlands.
Fabb et al., "Adeno-associated virus vector gene transfer and sarcolemmal expression of a 144 kDa micro-dystrophin effectively restores the dystrophin-associated protein complex and inhibits myofibre degeneration in nude/mdx mice", Human Molecular Genetics, 2002, pp. 733-741, vol. 11, No. 7, Oxford University Press, Oxford, United Kingdom.
Flanigan et al., "Anti-Dystrophin T Cell Responses in Duchenne Muscular Dystrophy: Prevalence and a Glucocorticoid Treatment Effect", Human Gene Therapy, Sep. 2013, pp. 797-806, 24, Mary Ann Liebert, Inc. New Rochelle, NY.
Hoffman et al., "Restoring Dystrophin Expression in Duchenne Muscular Dystrophy Muscle", The American Journal of Pathology, Jul. 2011, pp. 12-22, vol. 179, No. 1, Elsevier, Amsterdam, Netherlands.
Ho et al., "Tolerizing DNA vaccines for autoimmune arthritis", Autoimmunity, Dec. 2006, pp. 675-682, 39(8), Informa UK Ltd., London, United Kingdom.
Malueka et al., "Categorization of 77 dystrophin exons into 5 groups by a decision tree using indexes of splicing regulatory factors as decision markers", BMC Genetics, 2012, pp. 1-10, 13:23, BioMed Central Ltd, London, United Kingdom.
Mendell et al., "Dystrophin Immunity in Duchenne's Muscular Dystrophy", N Engl J Med, Oct. 7, 2010, pp. 1429-1437, 363;15, Massachusetts Medical Society, Waltham, MA.

(Continued)

*Primary Examiner* — Thaian N Ton
(74) *Attorney, Agent, or Firm* — Pamela J. Sherwood; Bozicevic, Field & Francis LLP

(57) ABSTRACT

The instant disclosure provides replacement gene tolerizing vectors and methods of using such vectors for treating individuals receiving gene therapy for muscular dystrophy, e.g., Duchenne muscular dystrophy (DMD), Becker muscular dystrophy (BMD), etc. Aspects of the methods include administering to the individual, in need thereof, an effective amount of a gene therapy tolerizing vaccine composition that includes a replacement gene tolerizing vector to reduce one or more symptoms of a subject's immune response to gene therapy treatment for muscular dystrophy and/or improve the efficacy of the gene therapy. Compositions and kits for practicing the methods of the disclosure are also provided.

4 Claims, 15 Drawing Sheets
(10 of 15 Drawing Sheet(s) Filed in Color)
Specification includes a Sequence Listing.

(56) References Cited

OTHER PUBLICATIONS

Solvason et al., "Improved Efficacy of a Tolerizing DNA Vaccine for Reversal of Hyperglycemia through Enhancement of Gene Expression and Localization to Intracellular Sites", The Journal of Immunology, 2008, pp. 3298-8307, The American Association of Immunologists, Rockville, MD.

* cited by examiner

AAV6 WEEK 5

AAV6 WEEK 16

Correlation between twitch and tetanus.

Correlation between positive fibers and twitch.

Correlation between positive tissue and twitch.

Correlation between pixel intensity and twitch.

Correlation between positive pixels and twitch.

Correlation between positive fibers and tetanus.

Correlation between positive tissue and tetanus.

Correlation between pixel intensity and tetanus.

Correlation between positive pixels and tetanus.

Positive fibers in the different experimental conditions

Positive tissues in the different experimental conditions

Pixel intensity in the different experimental conditions

Positive pixels in the different experimental conditions

REPLACEMENT GENE TOLERIZING VECTORS AND METHODS OF USE THEREOF

CROSS-REFERENCE TO RELATED APPLICATIONS

This application claims priority to U.S. Provisional Application No. 62/195,622 filed on Jul. 22, 2015, which application is herein incorporated by reference in its entirety.

INCORPORATION BY REFERENCE OF SEQUENCE LISTING

A Sequence Listing is provided herewith as a text file, "STAN-1196_SeqList_ST25.txt" created on Jul. 20, 2016 and having a size of 76 KB. The contents of the text file are incorporated by reference herein in their entirety.

BACKGROUND

Since the advent of molecular genetics the correction of human genetic lesions through the introduction of replacement genes has been a goal of human gene therapy. Various methods of gene replacement have been investigated including in situ replacement of a disease gene or portion thereof, supplementation of a disease gene through providing a replacement gene exogenously, e.g., on a non-integrating transgene or a transgene designed to integrate at a exogenous locus, and various other methods. While these approaches have appeared promising in the laboratory and even in some pre-clinical animal models, in human clinical trials they have been hampered by many roadblocks including induction of a host immune activity in response to the gene therapy. An example of one such condition with well-studied genetic lesions that have been targeted with replacement gene therapy is muscular dystrophy.

Statistics for the prevalence of combined muscular dystrophies are scarce. A four state study estimated that 1 of every 5,600 to 7,700 males ages 5 through 24 years of age have either Duchenne or Becker muscular dystrophy, with 82% of such patients being wheelchair bound by 10 to 14 years of age and 90% by ages 15 to 24. In the absence of family history, Becker muscular dystrophy (BMD) and Duchenne muscular dystrophy (DMD) combined are generally diagnosed about 2.5 years from symptom onset which is generally noticed at an average age of 2.5 years and presents as proximal muscle weakness causing waddling gait, toe-walking, lordosis, frequent falls, and difficulty in standing up and climbing up stairs. Many patients also present with cognitive impairment including lower than expected IQ. Symptoms progress more rapidly in DMD than BMD and the course of BMD is generally more benign. DMD is a severe X-linked recessive, progressive muscle-wasting disease which alone affects about 1 in 3,500 boys. Patients with DMD generally do not survive past their late teens or early twenties. The primary cause of death in patients with DMD is respiratory failure, due to intercostal muscle weakness, and/or cardiac complications including cardiomyopathy.

Dystrophin-related muscular dystrophies, including DMD and BMD, are caused by mutations in the dystrophin gene, which encodes a 427-kDa β-spectrin/α-actinin protein family member protein, and/or mutations in genes encoding components of the dystrophin-associated protein complex. Various mutations in dystrophin-related muscular dystrophies result in complete absence of dystrophin protein (null mutation) as well as reduced levels of dystrophin protein, shortened dystrophin protein (deletion mutation), truncated dystrophin protein (premature stop codon mutation), tissue specific misexpression or reduced expression of dystrophin protein, reduced dystrophin-associated protein complex formation and combinations thereof. The human dystrophin gene is located on the X chromosome at position Xp21 and spans about 2.5 Mb of genomic sequence and is composed of 79 exons. The resulting 14-kb mRNA dystrophin transcript is expressed, through three independently regulated promoters, predominantly in skeletal and cardiac muscle with minor expression in the brain. While there is some correlation between severity of the genetic lesion causing a dystrophin-related muscular dystrophy and severity of the disease phenotype, some large deletions, e.g., in the dystrophin rod domain, appear to be uncorrelated resulting in relatively benign phenotypes.

These clinically mild yet dramatically shortened dystrophin mutant proteins have been the basis for the development of mini-dystrophin genes used in various dystrophin gene therapies. While dystrophin gene therapies, whether based on delivery of a mini-dystrophin gene or other dystrophin encoding nucleic acid, have shown promise in the laboratory and pre-clinical studies with muscular dystrophy animal models, human clinical studies have been met with significant setbacks, including dystrophin replacement gene specific immunity in treated DMD subjects.

PUBLICATIONS

Blake et al. *Physiol Rev.* 82:291-329, 2002.
Centers for Disease Control and Prevention (CDC). *MMWR Morb Mortal Wkly Rep.* 2009; 58(40):1119-22.
Ehmsen et al. *Journal of Cell Science.* 115:2801-2803, 2002.
Mendell et al. *New England Journal of Medicine.* 363(115): 1429-1437.

SUMMARY

Methods are provided for treating a subject having a host immune reaction associated with delivery of a replacement gene as part of a gene therapy administered to treat the subject for muscular dystrophy. Aspects of the method include administering to the subject a tolerizing vector to induce immunological tolerance to one or more specific antigens of a gene therapy vector. Suppression of a host immune response to muscular dystrophy gene therapy may be performed as an "add-on therapy" to supplement a muscular dystrophy replacement gene therapy and to generally improve the overall efficacy of the gene therapy. Aspects of the instant disclosure include replacement gene tolerizing vectors and methods of using such vectors. Such tolerizing vectors may be configured to express one or more particular antigens of a gene therapy vector, including polypeptides encoded from the replacement gene, and have a reduced number of immune stimulating motifs and/or an increased number of immune suppressive motifs, e.g., as compared to the gene therapy vector or other standard gene transfer vectors. Aspects of the subject methods further include administering to the individual, in need thereof, an effective amount of a replacement gene tolerizing vector to at least reduce one or more symptoms associated with a host immune response to a muscular dystrophy gene therapy and/or prevent the onset of one or more symptoms associated with a host immune response to a muscular dystrophy gene therapy. Also provided are compositions and kits for practicing the methods of the disclosure.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
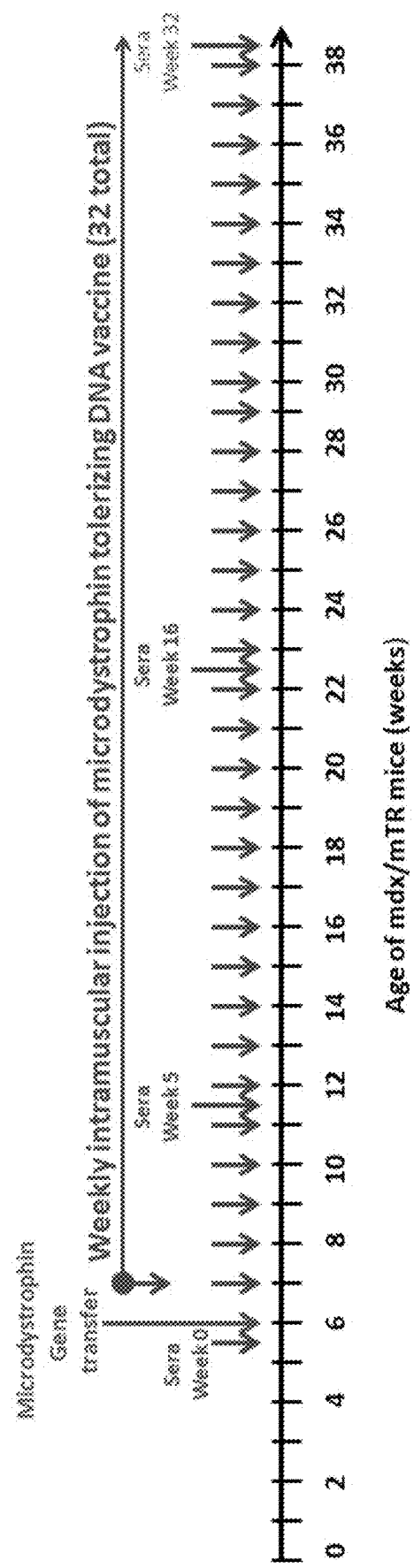
FIG. 1 provides a schematic representation of the dosing and serum collection schedule performed in experiments testing pBHT1CI-H3UDYS as described herein.

The instant disclosure provides replacement gene tolerizing vectors and methods of using such vectors for treating individuals receiving gene therapy for muscular dystrophy, e.g., Duchenne muscular dystrophy (DMD), Becker muscular dystrophy (BMD), etc. Aspects of the methods include administering to the individual, in need thereof, an effective amount of a gene therapy tolerizing vaccine composition that includes a replacement gene tolerizing vector to reduce one or more symptoms of a subject's immune response to gene therapy treatment for muscular dystrophy. Compositions and kits for practicing the methods of the disclosure are also provided.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", an, and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Definitions A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors, however, in some instances a vector may be configured to prevent, eliminate or inhibit the integration of the vector into a host cell genome.

The term "plasmids" are encompassed within the term "vector" and refers to any genetic element that is capable of replication by comprising proper control and regulatory elements when present in a host cell. Plasmids may be designated by a lower case p followed by letters and/or numbers. Starting plasmids are commercially available, publicly available on an unrestricted basis, can be constructed from available plasmids in accord with published procedures, can be isolated from organisms harboring the plasmid (e.g., naturally occurring organisms or laboratory stocks (e.g., bacterial stocks, etc.), or synthesized, in whole or in part, on a standard or custom basis, e.g., as provided by commercial suppliers such as DNA2.0, Inc. (Menlo Park, Calif.)). In addition, where equivalent plasmids to those described are known in the art such plasmids will be readily apparent to the ordinarily skilled artisan and the nucleic acid sequences of such plasmids may be readily available.

Vectors are capable of transferring nucleic acid sequences to target cells and, in some instances, are used to manipulate nucleic acid sequence, e.g., recombine nucleic acid sequences (i.e. to make recombinant nucleic acid sequences). For purposes of this invention examples of vectors include, but are not limited to, plasmids, phage, transposons, cosmids, virus, and the like.

"Naked nucleic acid" as used herein refers to a nucleic acid molecule that is not encapsulated (such as, e.g., within a viral particle, bacterial cell, or liposome) and not complexed with a molecule that binds to the nucleic acid (such as, e.g., DEAE-dextran) nor otherwise conjugated to the nucleic acid (e.g., gold particles or polysaccharide-based supports).

An "expression cassette" comprises any nucleic acid construct capable of directing the expression of any RNA transcript including gene/coding sequence of interest as well as non-translated RNAs. Such cassettes can be constructed into a "vector," "vector construct," "expression vector," or "gene transfer vector," in order to transfer the expression cassette into target cells. Thus, the term includes cloning and expression vehicles, as well as viral vectors.

The terms "polypeptide" and "protein" are used interchangeably to refer to a polymer of amino acid residues linked by peptide bonds, and for the purposes of the instant disclosure, have a minimum length of at least 5 amino acids. Oligopeptides, oligomers multimers, and the like, typically refer to longer chains of amino acids and are also composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 5 amino acids are encompassed by the definition. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity relevant to the purposes of the described methods. These modifications can be deliberate, as through site-directed mutagenesis, or can be accidental, such as through mutations of hosts that produce the proteins, or errors due to PCR amplification or other recombinant DNA methods.

Modified polypeptides may also include, e.g., those polypeptides that have been modified to improve their use as a therapeutic. Such polypeptide modification may include any combination of N- and/or C-terminal truncation (e.g., to achieve the minimal active sequence (MAS)), deletion of one or more consecutive amino acid(s) to achieve the MAS, combinatorial deletion with two or more positions omitted independently to achieve the MAS, structure simplification (e.g., following alanine or D amino acid scanning to identify non-active sites), cleave site elimination, cyclization between side chains, cyclization between terminal ends, cyclization between the backbone, cyclization between a terminal end and a side chain, cyclization between a terminal end and the backbone, cyclization between a side chain and the backbone, cyclization through disulfide bonding, modification to reduce polypeptide flexibility (e.g., through peptide bridging, e.g., lanthionine bridging, dicarba bridging, hydrazine bridging, lactam bridging), modification to reduce hydrogen bonding, modification to increase membrane permeability (e.g., by modifying the overall or regional (e.g., surface) charge of a polypeptide), unnatural amino acid (e.g., a D-amino acid) substitution, N-methyl-α-amino acid substitution, β-amino acid substitution, amide bond replacement, terminal end blocking (e.g., through N-acylation, N-pyroglutamate, C-amidation, etc.), addition of carbohydrate chains, N-terminal esterification, pegylation, and the like. Polypeptide modifications have been described, e.g., by Vlieghe et al. (2010) *Drug Discovery Today*. 15:(1/2) 40-56, the disclosure of which is incorporated herein by reference. The ordinary skilled artisan will readily understand where a polypeptide modification may be encoded (e.g., an amino acid substitution, amino acid addition, amino acid truncation, etc.) in a nucleic acid. The ordinary skilled artisan will also readily understand that where a polypeptide modification is initially synthetically produced (e.g., through enzymatic truncation of a polypeptide) such modification may, in some instances, also be achieved by modifying a nucleic acid that encodes the polypeptide (e.g., by truncating the nucleic acid).

The term "gene" refers to a particular unit of heredity present at a particular locus within the genetic component of an organism. A gene may be a nucleic acid sequence, e.g., a DNA or RNA sequence, present in a nucleic acid genome, a DNA or RNA genome, of an organism and, in some instances, may be present on a chromosome. Typically a gene will be a DNA sequence that encodes for an mRNA that encodes a protein. A gene may be comprised of a single exon and no introns or multiple exons and one or more introns. One of two or more identical or alternative forms of a gene present at a particular locus is referred to as an "allele" and, for example, a diploid organism will typically have two alleles of a particular gene. New alleles of a particular gene may be generated either naturally or artificially through natural or induced mutation and propagated through breeding or cloning.

The terms "specific binding," "specifically binds," and the like, refer to non-covalent or covalent preferential binding to a molecule relative to other molecules or moieties in a solution or reaction mixture (e.g., an antibody specifically binds to a particular polypeptide (e.g., antigen) or epitope relative to other available polypeptides). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Life Technologies, Inc., Sigma-Aldrich, and ClonTech.

Replacement Gene Tolerizing Vectors

Aspects of the disclosure include replacement gene tolerizing vectors comprising a nucleic acid (i.e., a tolerizing sequence) encoding for an antigenic polypeptide of a replacement dystrophin gene (i.e., therapeutic sequence) delivered to a host by a muscular dystrophy gene therapy vector (i.e., gene therapy vector) as part of a muscular dystrophy gene therapy. Aspects of the disclosure also include tolerizing vaccine compositions comprising such vectors, for the suppression of a host immune response (i.e., DMD gene therapy immune response) associated with a gene therapy vector. Replacement gene tolerizing vectors (i.e., tolerizing vectors) may be delivered separately or together. For example, a tolerizing vector may be delivered independently (e.g., as part of a separate therapy, e.g., responsive to a host immune reaction, prophylactically before a host immune response, etc.) and/or as part of a gene therapy composition that includes a replacement gene tolerizing vector (i.e., as an integrated gene therapy) delivered concomitantly. In many instances, administration of a tolerizing vector is delivered as an "add on therapy" following the gene therapy or following the start of the gene therapy. For example, the tolerizing vector may be administered following administration of the gene therapy but before the host mounts a robust immune response to the gene therapy, i.e., the tolerizing vector may be administered for suppression of a host immune response following gene therapy.

In some aspects of the disclosure, the tolerizing vector, e.g., as part of a tolerizing vaccine composition, has been modified relative to conventional vectors to have a low number of immunostimulatory CpG motifs. The number of immunostimulatory CpG motifs present in a tolerizing vector will vary, e.g., depending on the particular vector components present in the vector and the presence of immunostimulatory CpG motifs in the sequence of individual vector components. As such, the number of immunostimulatory CpG motifs present in a tolerizing vector, excluding any immunostimulatory CpG motifs that may be present in the tolerizing nucleic acid encoding the antigenic polypeptide(s), may range from 18 or less to 25 or more (but will generally be less than 31), including but not limited to, e.g., 30 or less, 29 or less, 28 or less, 27 or less, 26 or less, 25 or less, 24 or less, 23 or less, 22 or less, 21 or less, 20 or less, 19 or less, 18 or less, etc. Immunostimulatory motifs may be readily removed from non-coding and non-regulatory vector sequence (e.g., vector backbone) through the nucleotide substation. In some instances, immunostimulatory motifs may be removed from coding sequences through "silent" nucleotide substitution, i.e., nucleotide substitution that does not result in a change in the coded amino acid sequence. Such, substitutions need not necessarily be silent mutations provided any change in the coded amino acid sequence does not have a significant adverse impact the function of the coded polypeptide. In some instances, the number of immunostimulatory motifs present in a tolerizing vector may depend on immunostimulatory motifs present in regulatory sequences or coding sequences that cannot be altered without negatively impacting the function of the regulatory sequence or the polypeptide expressed from the coding sequence.

In some aspects of the disclosure, the tolerizing vector, e.g., as part of a tolerizing vaccine composition, is selected to include immunosuppressive GpG motifs or to have a high number of immunosuppressive GpG motifs relative to conventional vectors. For example, in some instances, the vector, e.g., the vector backbone, comprises at least one immunosuppressive GpG motif. The number of immunosuppressive GpG motifs present in the vector will vary and may range from 1 to 10 or more including but not limited to, e.g., 1 or more, 2 or more, 3 or more, 4 or more, 5 or more, 6 or more, 7 or more, 8 or more, 9 or more, etc.

In general, at least one coding sequence of the tolerizing vector will encode all or a portion of the antigenic polypeptide of the gene therapy vector. In aspects of the disclosure, the antigenic polypeptide of the gene therapy vector, e.g., for which a tolerizing vector and/or tolerizing vaccine composition is administered, is a polypeptide encoded from a dystrophin gene. In some instances, the therapeutic sequence of the gene therapy vector may be a microdystrophin gene. In some instances, the therapeutic sequence of the gene therapy vector may be a full length dystrophin gene. The tolerizing vector may encode for the entire therapeutic sequence or a portion thereof, including, e.g., one or more antigenic epitopes of the therapeutic sequence.

In some aspects of the disclosure, a tolerizing vaccine composition for suppression of a host immune response to a gene therapy vector may include a tolerizing vector directed at a vector-immunogen (i.e. a vector-immunogen tolerizing vector or "vehicle tolerizing vector"). Such vehicle tolerizing vectors may suppress a host immune response to a component of the gene therapy vector other than the antigenic polypeptide encoded from the therapeutic sequence, e.g., a component of the vector itself. Such a vehicle tolerizing vector may include DNA encoding for a vector-immunogen of the gene therapy vector.

In some aspects, a vehicle tolerizing vector may have been modified to have a low number of immunostimulatory CpG motifs relative to conventional vectors. For example, in some instances, the vector, excluding any immunostimulatory CpG motifs that may be present in the tolerizing nucleic acid encoding the vector-immunogen(s), may be modified to have 30 or fewer immunostimulatory CpG motifs, including but not limited to, e.g., 29 or less, 28 or less, 27 or less, 26 or less, 25 or less, 24 or less, 23 or less, 22 or less 21 of less, 20 or less, 19 or less, 18 or less, etc. In some aspects, a vehicle tolerizing vector is selected that includes immunosuppressive GpG motifs or has a high number of immunosuppressive GpG motifs relative to conventional vectors. For example, in some instances, the vector, e.g., the vector backbone, comprises at least one immunosuppressive GpG motif. In some instances, a vector-immunogen of a vehicle tolerizing vector may be a viral polypeptide of a viral gene therapy vector, e.g., a viral capsid polypeptide. The number of immunosuppressive GpG motifs present in the vector will vary and may range from 1 to 10 or more including but not limited to, e.g., 1 or more, 2 or more, 3 or more, 4 or more, 5 or more, 6 or more, 7 or more, 8 or more, 9 or more, etc.

In certain aspects of the disclosure, methods are provided for suppressing a host immune response to a gene therapy vector by administering to a host an effective amount of a tolerizing vector comprising nucleic acid sequence encoding for all or a portion of a muscular dystrophy replacement polypeptide encoded from the therapeutic sequence of a gene therapy vector. In some aspects, the therapeutic sequence is a microdystrophin gene. In some aspects, the therapeutic sequence is a full length dystrophin gene.

In some aspects of the disclosure, administration of an effective amount of a tolerizing vector comprising nucleic acid sequence encoding for all or a portion of a replacement polypeptide encoded from a therapeutic sequence results in a reduced host antibody response to the replacement polypeptide and/or improved efficacy of the gene therapy.

In some aspects of the disclosure, methods for suppressing a host immune response to a muscular dystrophy gene therapy vector may further include administration of an effective amount of a tolerizing vector comprising nucleic acid sequence encoding for a vector immunogen of the gene therapy vector. In some aspects, the immunogen may be a viral polypeptide of the gene therapy vector, e.g., a viral capsid polypeptide.

In some aspects of the disclosure, methods are provided for suppressing a host immune response to a muscular dystrophy gene therapy vector resulting in a reduced host antibody response to a component of the gene therapy vector, e.g., a vector immunogen, where the host immune response is a result of the gene therapy administered to a subject.

In some aspects of the disclosure, methods are provided for suppressing a host immune response to a muscular dystrophy gene therapy vector by administering a tolerizing vector following muscular dystrophy gene therapy. In some aspects of the disclosure, methods are provided for suppressing a host immune response to a muscular dystrophy gene therapy vector by administering a tolerizing vector following the start of the muscular dystrophy gene therapy. In some aspects of the disclosure, methods are provided for suppressing a host immune response to a muscular dystrophy gene therapy vector by administering a tolerizing vector following the start of the muscular dystrophy gene therapy but essentially before the host mounts a significant immune response to the gene therapy. In instances where the tolerizing vector is administered following the start of the gene therapy the time between the start of the gene therapy and the administration of the gene therapy vector will vary and will depend on, e.g., a predetermined tolerizing therapy schedule, the immune response of the host or lack thereof, the effectiveness of the gene therapy, and the like. As such, in some instances, the time between the start of the gene therapy and the administration of the tolerizing vector may range from hours to weeks or more including but not limited to, e.g., less than 12 hours, less than 24 hours, less than 2 days, less than 3 days, less than 4 days, less than 5 days, less than 6 days, less than a week, less than 2 weeks, more than 12 hours, more than 24 hours, more than 2 days, more than 3 days, more more 4 days, more than 5 days, more than 6 days, more than a week, from 12 hours to 24 hours, from 24 hours to 2 days, from 24 hours to 3 days, from 2 days to 3 days, from 2 days to 4 days, from 2 days to 5 days, from 3 days to 5 days, from 3 days to 6 days, from 4 days to 6 days, from 4 days to a week, from 5 days to a week, and the like.

Aspects of the disclosure include tolerizing vectors comprising nucleic acid encoding for a muscular dystrophy polypeptide and/or a polypeptide encoded from a therapeutic sequence. By "therapeutic sequence" is meant a nucleic acid sequence delivered as part of a gene therapy from which a replacement polypeptide is encoded (e.g., a dystrophin polypeptide meant to replace a disease-related dystrophin polypeptide of the host). In some instances, a muscular dystrophy polypeptide or a polypeptide encoded from a muscular dystrophy therapeutic sequence may be referred herein to as an antigen. Methods are provided, described in more detail below, for treating a subject having an adverse immune response to a muscular dystrophy gene therapy or one or more components thereof. Accordingly, as used herein, the terms "replacement gene tolerizing vector" and "tolerizing vector" may refer to a vector containing nucleic acid containing one or more therapeutic sequences and encoding for one or more muscular dystrophy replacement polypeptides.

Tolerizing vectors therefore include nucleic acid encoding for all or a portion of a replacement polypeptide of a gene therapy vector. For example, a tolerizing vector may comprise the entire therapeutic sequence of the gene therapy vector and thus encode the entire replacement polypeptide. In other instances, a tolerizing vector may comprise only a portion of the therapeutic sequence of the gene therapy vector and thus encode only a portion of the replacement polypeptide, e.g., one or more antigenic epitopes of the replacement polypeptide. Tolerizing vectors may further comprise, as described in more detail herein, sequence encoding for one or more antigenic components of the gene therapy vector itself apart from the replacement polypeptide, e.g., a component of the vehicle itself.

As described herein, a tolerizing vector may be a component of a gene therapy composition wherein the inclusion of the tolerizing vector in the gene therapy composition provides for suppression of host immune response that results from a component of the gene therapy vector. The components of a vaccine containing a tolerizing vector will vary and will include, at a minimum, a vector that contains a nucleic acid sequence encoding a gene therapy replacement gene polypeptide and the necessary components for expression of the replacement gene polypeptide from the vector. Nucleic acid sequence encoding for any gene therapy replacement gene polypeptide, including those described herein, may find use in a tolerizing vaccine.

Vector Minigenes

In some instances, a tolerizing vaccine includes a minigene that includes nucleic acid encoding for one or more polypeptides of muscular dystrophy gene. As used herein the term "minigene" refers to a minimal gene fragment that excludes one or more components of a native gene locus but includes the necessary elements for expression of the gene product or some portion of the gene product or a synthetic construct. In some instances, a muscular dystrophy gene therapy minigene may exclude at least one muscular dystrophy gene intron, or portion thereof, including but not limited to 1 or more introns, including e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 or 77 or more introns, including all the introns of the native muscular dystrophy genetic locus. In some instances, an muscular dystrophy gene therapy minigene may include at least one muscular dystrophy gene intron, or portion thereof, including but not limited to 1 or more introns, including e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 or 77 or more introns, or all the introns of the native muscular dystrophy genetic locus. In some instances, a muscular dystrophy gene therapy minigene may exclude at least one muscular dystrophy gene exon, or portion thereof, including but not limited to 1 or more exons, including e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 or 77 or more exons, or all but a portion of one exon of the native muscular dystrophy genetic locus. In some instances, a muscular dystrophy gene therapy minigene may include at least one muscular dystrophy gene exon, or portion thereof, including but not limited to 1 or more exons, including e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77 or 78 or more exons or more exons or all the exons of the native muscular dystrophy genetic locus. As such, given the large size of certain muscular dystrophy genes, e.g., dystrophin, and the varied length of exons and introns of such muscular dystrophy genes, in some instances a minigene may not necessarily be "mini" and may be large in terms of overall nucleic acid sequence depending on the particular configuration of the minigene, e.g., the number of exons included in the minigene, the number of introns included in the minigene, the particular exon(s) included in the minigene, the particular intron(s) included in the minigene, etc.

In some instances, a minigene may include nucleic acid encoding for one antigenic epitope of a muscular dystrophy gene. In some instances, a minigene may include two or more antigenic epitopes of a muscular dystrophy gene, e.g., arranged in series and joined with or without one or more optional linkers. In some instances, nucleic acid encoding for epitopes of two or more different components of a muscular dystrophy gene therapy vector may be included in a minigene construct including but not limited to, e.g., components of the muscular dystrophy gene therapy gene, components of the gene therapy vector, and the like. An antigenic epitope may consist of an exon or one or more portions thereof or portions of two or more exons. In some instances, multiple antigenic epitopes from the same exon and/or from multiple different exons are arranged in series and contained within a minigene. Methods of generating such strings of antigenic epitopes include but are not limited to, e.g., those described in Whitton et al. *J Virol.* 1993 January; 67(1): 348-352, the disclosure of which is incorporated herein by reference in its entirety.

A minigene will also include at least some regulatory sequence that controls or enhances the expression of the minigene transcript. In some instances, a minigene regulatory sequence will include a promoter. Promoters useful in muscular dystrophy gene therapy minigene will vary and selection of such a minigene promoter will depend on various factors including the desired expression level of the minigene transcript, the desired control of minigene expression, the desired size of the overall minigene, the intended use of the minigene, including the subject to which the minigene may be delivered. Such minigene promoters may include but are not limited to a native muscular dystrophy gene promoter, a native non-muscular dystrophy gene promoter (i.e., a promoter native to organism from which the muscular dystrophy gene sequence was derived but not associated with the native muscular dystrophy gene locus), a heterologous promoter (i.e., a promoter derived from an organism other than the organism from which the muscular dystrophy gene sequence was derived (e.g., a non-human promoter, a non-mammalian promoter, etc.)), a minimal promoter, a minipromter, a constitutive promoter, a tissue specific promoter, an inducible promoter, a synthetic promoter and the like.

Vector Backbones

In some instances, a replacement gene tolerizing vaccine will include a vector backbone, e.g., a plasmid polynucleotide backbone. Vector backbones useful in a replacement gene tolerizing vaccine will vary and may be selected based on a number of factors. For example, in some instances, a vector backbone may be selected based on the absence or minimal presence of nucleotide sequence that is homologous with one or more desired host organisms of the replacement gene tolerizing vaccine (i.e., an organism that will ultimately receive the replacement gene tolerizing vaccine) in order to prevent or minimize the likelihood of homologous recombination between the vector and the host organism genome. The amount of homologous sequence between the vector backbone and the host organism may vary and, in some instances, the vector backbone may not contain any sequence homologous to the host organism that is longer than 200 nucleotides, including but not limited to, e.g., longer than 150 nucleotides, longer than 100 nucleotides, longer than 90 nucleotides, longer than 80 nucleotides, longer than 70 nucleotides, longer than 60 nucleotides, longer than 50 nucleotides, longer than 40 nucleotides, longer than 30 nucleotides or longer than 25 nucleotides. In some instances, the vector may have further features that prevent integration into a host genome, e.g., the vector may be a closed-circular plasmid.

Vector Specific Elements and Immunomodulatory Motifs

A vector of a replacement gene tolerizing vaccine may include one or more vector specific elements. By "vector specific elements" is meant elements that are used in making, constructing, propagating, maintaining and/or assaying the vector before, during or after its construction and/or before its use in a replacement gene tolerizing vaccine. Such vector specific elements include but are not limited to, e.g., vector elements necessary for the propagation, cloning and selection of the vector during its use and may include but are not limited to, e.g., an origin of replication, a multiple cloning site, a prokaryotic promoter, a phage promoter, a selectable marker (e.g., an antibiotic resistance gene, an encoded enzymatic protein, an encoded fluorescent or chromogenic protein, etc.), and the like. Any convenient vector specific elements may find use, as appropriate, in the vectors as described herein.

In some instances, one or more vector specific elements, including the vector backbone, of a tolerizing vector is selected or configured to reduce the number of immunostimulatory motifs present in the vector. For example, a nucleic acid vector may be modified where a non-CpG dinucleotide is substituted for one or more CpG dinucleotides of the formula 5'-purine-pyrimidine-C-G-pyrimidine-pyrimidine-3' or 5'-purine-purine-C-G-pyrimidine-pyrimidine-3', thereby producing a vector in which immunostimulatory activity is reduced. Such vectors are useful, for example, in methods for administering immune modulatory nucleic acids and/or for administering a tolerizing vaccine encoding one or more muscular dystrophy immunogenic gene therapy vector polypeptides. For example, the cytosine of the CpG dinucleotide can be substituted with guanine, thereby yielding a region having a GpG motif of the formula 5'-purine-pyrimidine-G-G-pyrimidine-pyrimidine-3' or 5'-purine-purine-G-G-pyrimidine-pyrimidine-3'. The cytosine can also be substituted with any other non-cytosine nucleotide. The substitution can be accomplished, for example, using site-directed mutagenesis. Typically, the substituted CpG motifs are those CpGs that are not located in one or more regulatory regions of the vector (e.g., promoter regions) and/or vector specific element, as described herein. In addition, where the CpG is located within a coding region of an expression vector (e.g., the coding region of a vector specific element, such as a selectable marker), the non-cytosine substitution is typically selected to yield a silent mutation or a codon corresponding to a conservative substitution of the encoded amino acid.

For example, in certain embodiments, a modified pVAX1 vector is utilized in which one or more CpG dinucleotides of the formula 5'-purine-pyrimidine-C-G-pyrimidine-pyrimidine-3' has been mutated by substituting the cytosine of the CpG dinucleotide with a non-cytosine nucleotide. The pVAX1 vector is known in the art and is commercially available from Life Technologies, Inc. (Grand Island, N.Y.). In one exemplary embodiment, the modified pVAX1 vector has the following cytosine to non-cytosine substitutions within a CpG motif: cytosine to guanine at nucleotides 784, 1161, 1218, and 1966; cytosine to adenine at nucleotides 1264, 1337, 1829, 1874, 1940, and 1997; and cytosine to thymine at nucleotides 1963 and 1987; with additional cytosine to guanine mutations at nucleotides 1831, 1876, 1942, and 1999 where the nucleotide number designations as set forth above are according to the numbering system for pVAX1 provided by Life Technologies, Inc. (Grand Island, N.Y.). In some instances, a modified pVAX1 vector is pBHT1 (SEQ ID NO:1) and in some instances a tolerizing vector may comprise a modified pBHT1, e.g., pBHT1CI.

"pBHT1CI" as used herein refers to a pBHT1 vector into which a chimeric intron has been introduced to improve expression of any inserted tolerizing gene. Insertion of a chimeric intron into vector of interest can be achieved by any convenient method of targeted insertion, including digestion-ligation cloning, homology based cloning, etc. For example, for pBHT1CI, the chimeric intron was positionally cloned between the CMV promoter and the tolerizing gene coding sequence site of pBHT1 using the multiple cloning site present on the pBHT1 vector. Specifically, following positional cloning, the chimeric intron is present at positions 702-835 in the resultant pBHT1CI vector. Any convenient chimeric intron sufficient to appropriately increase expression of the tolerizing gene may be employed in this fashion. For example, for pBHT1CI, the chimeric intron was derived from the commercially available expression vector pTarget (Promega, Madison, Wis.; SEQ ID NO:2), specifically 133 base pairs from the pTarget vector. A non-limiting example of chimeric intron sequence that can be used in this fashion is the chimeric intron sequence of pTarget between positions 890-1022:

(SEQ ID NO: 3)
GTAAGTATCAAGGTTACAAGACAGGTTTAAGGAGACCAATAGAAACTGGG

CTTGTCGAGACAGAGAAGACTCTTGCGTTTCTGATAGGCACCTATTGGTC

TTACTGACATCCACTTTGCCTTTCTCTCCACAG.

In some instances, vector specific elements, including the vector backbone, include or exclude certain immune modulatory sequences, e.g., exclude immunostimulatory sequences and/or include immunoinhibitory sequences, or have increased numbers of immunoinhibitory sequences and/or decreased numbers of immunostimulatory sequences. The use of immune modulatory sequences, including but not limited to, e.g.: GTGGTT, ATGGTT, GCGGTT, ACGGTT, GTGGCT, ATGGCT, GCGGCT, ACGGCT, GTGGTC, ATGGTC, GCGGTC, ACGGTC, GTGCTT, ATGCTT, GCGCTT, ACGCTT, GTGCCT, ATGCCT, GCGCCT, ACGCCT, GTGCTC, ATGCTC, GCGCTC, ACGCTC, GGGGTT, AGGGTT, GAGGTT, AAGGTT, GGGGCT, AGGGCT, GAGGCT, AAGGCT, GGGGTC, AGGGTC, GAGGTC, AAGGTC, GGGCTT, AGGCTT, GAGCTT, AAGCTT, GGGCCT, AGGCCT, GAGCCT, AAGCCT, GGGCTC, AGGCTC, GAGCTC and AAGCTC; and the generation and use of vectors containing reduced numbers of immunostimulatory sequences and increased numbers of immunoinhibitory sequences have been described, e.g., in U.S. Pat. No. 7,811,813, the disclosure of which is incorporated herein by reference in its entirety.

A vector of a replacement gene tolerizing vaccine, whether or not configured to contain a minigene, will further include one or more regulatory elements. Such regulatory elements will vary and may include but are not limited to, e.g., a promoter, an enhancer, an intron, a polyadenylation signal, an initiation sequence (e.g., a Kozak sequence), and the like. Promoters useful in the expression of an replacement gene polynucleotide include but are not limited to, e.g., a promoter native to the replacement gene, a native promoter that is not naturally associated with the replacement gene (i.e., a promoter native to organism from which the replacement gene sequence was derived but not associated with the native replacement gene locus), a heterologous promoter (i.e., a promoter derived from an organism other than the organism from which the replacement gene sequence was derived (e.g., a non-human promoter, a non-mammalian promoter, etc.)), a minimal promoter, a minipromter, a constitutive promoter, a tissue specific promoter, an inducible promoter, a synthetic promoter and the like.

Promoters may be operably linked to a nucleic acid encoding the replacement gene polypeptide or fragment thereof to control production of encoded transcript either in vitro or in vivo. Such promoters may be constitutively active or controllable through the introduction of a stimulus, e.g., an environmental stimulus (e.g., change in temperature, pH, light exposure, and the like), a chemical or biological stimulus (e.g., a small molecule, a chemical, a polypeptide that binds to the promoter, and the like). In some instances, a vector of a replacement gene tolerizing vaccine may include a cytomegalovirus promoter.

A replacement gene tolerizing vaccine regulatory element may also include one or more enhancer elements. Enhancers may be operably linked to a nucleic acid encoding a replacement gene polypeptide to control production of encoded transcript either in vitro or in vivo. Such enhancers may be constitutively active or controllable through the introduction of a stimulus, e.g., an environmental stimulus (e.g., change in temperature, pH, light exposure, and the like), a chemical or biological stimulus (e.g., a small molecule, a chemical, a polypeptide that binds to the enhancer, and the like). In some instances, a vector of a replacement gene tolerizing vaccine may include a cytomegalovirus enhancer.

Suitable promoter and enhancer elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable inducible promoters, including reversible inducible promoters are known in the art. Such inducible promoters may be isolated and derived from many organisms, e.g., eukaryotes and prokaryotes. Modification of inducible promoters derived from a first organism for use in a second organism, e.g., a first prokaryote and a second a eukaryote, a first eukaryote and a second a prokaryote, etc., is well known in the art. Such inducible promoters, and systems based on such inducible promoters but also comprising additional control proteins, include, but are not limited to, e.g., tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), temperature regulated promoters (e.g., heat shock inducible promoters (e.g., HSP-70, HSP-90, etc.), synthetic inducible promoters, and the like.

Transcriptional control elements, e.g., promoters, enhancers, etc., may be bound to a nucleic acid encoding a replacement gene polypeptide singly or in arrays containing multiple transcriptional control elements, e.g., about 2, about 3, about 4, about 5, or more than 5 transcriptional control elements. In certain embodiments, transcriptional control elements are operably linked, directly or indirectly to the 5' end of a nucleic acid encoding a replacement gene polypeptide with or without intervening "spacer" nucleic acid(s). Transcriptional control elements, methods of making and/or arranging and/or modifying transcription control elements (e.g., in expression cassettes) useful in the nucleic acids described herein may, in some instances, include those described in Liu et al., *Gene Therapy* (2004) 11:52-60; Zheng & Baum, *Methods Mol Biol.* 2008, 434:205-19; Papadakis et al., *Curr Gene Ther.* 2004, 4(1):89-113; the disclosures of which are incorporated herein by reference in their entirety.

A replacement gene tolerizing vaccine regulatory element may also include one or more introns wherein inclusion of the intron in the vector and/or minigene enhances the expression of the encoded polypeptide of the tolerizing vector. Such introns may be introns of the replacement gene (i.e., introns or portions thereof derived from a native genetic locus of the replacement gene) or may be native introns not associated with the natural replacement gene (i.e., introns derived from the intended host genome but from a locus other than the natural genetic locus of the replacement gene) or may be heterologous introns (i.e., introns derived from a genome or organism other than the intended host genome or host organism). For example, in some instances, a replacement gene tolerizing vaccine may include an intron, or fragment thereof, from a virus. For example, an intron from a cytomegalovirus including but not limited to the first intron of the cytomegalovirus or a minimal intron, including a minimal first intron, of the cytomegalovirus and/or those introns described in Quilici et al. *Biotechnol Lett.* 2013, 35(1):21-7 and Xu et al. *Gene.* 2001, 272(1-2):149-56; the disclosures of which are incorporated herein by reference in their entirety.

In some instances, a replacement gene tolerizing vaccine includes an appropriate diluent, e.g., a suitable solution or liquid for dissolving or suspending a vector as described herein. Such diluents may vary and may depend upon, e.g., the concentration of vector to be suspended, the pharmaceutical formulation, of the replacement gene tolerizing vaccine, the mode of delivery of the replacement gene tolerizing vaccine, the method of storage of the replacement gene tolerizing vaccine, and the like. In some instances, a suitable solution or liquid may include but is not limited to, e.g., aqueous solutions, water (e.g., nuclease-free water, water for injection (WFI), etc.), saline, phosphate buffered saline (PBS), tris buffer saline (TBS), tris-EDTA (TE) buffer, combinations thereof, and the like. Pharmaceutical formulations of DNA tolerizing vaccines are discussed in more detail below.

Muscular Dystrophy Gene Therapy Nucleic Acids and Polypeptides Encoded Therefrom Aspects of the disclosure include tolerizing nucleic acids and polypeptides encoded therefrom for use in treating a host immune response associated with administration of a muscular dystrophy gene therapy. By "tolerizing nucleic acid" is meant a nucleic acid, that encodes a polypeptide or portion thereof used in muscular dystrophy gene therapy, e.g., to replace or supplement a disease-associated muscular dystrophy polypeptide encoded from a disease-associated muscular dystrophy allele of the subject. A therapeutic nucleic acid administered as part of a muscular dystrophy gene therapy may be referred to herein as a "replacement gene". Such replacement genes may or may not resemble the native genetic locus of the disease allele. For example, in some instances, a replacement gene may be essentially the same as the native genetic locus of the disease gene but for correction of the disease-causing genetic lesion. In other instances, a replacement gene may vary greatly from the native gene of the disease locus and may be partly or wholly synthetic or recombinant. As such, the encoded polypeptide of a tolerizing vector may be based on the replacement gene of a gene therapy vector and all or a portion of an immunogenic polypeptide or epitope encoded therefrom. The following provides a description of exemplary replacement genes, and components thereof, upon which a tolerizing nucleic acid may be based or may resemble.

Muscular Dystrophy Replacement Genes

A replacement gene may be provided in a gene therapy approach for any muscular dystrophy arising out of a congenital or novel (i.e. new or non-inherited) genetic defect including but not limited to, e.g., Duchenne Muscular Dystrophy (DMD), Becker Muscular Dystrophy (BMD), Facioscapulohumeral Muscular Dystrophy 1 (FSHD1), Limb-Girdle Muscular Dystrophies, Congenital Merosin-Deficient Muscular Dystrophy, Emery-Dreifuss Muscular Dystrophies, Muscular Dystrophy-Dystroglycanopathies, Ullrich Congenital Muscular Dystrophy, Rigid Spine Muscular Dystrophy, Myotonic Dystrophy, Oculopharyngeal Muscular Dystrophy, Tibial Muscular Dystrophy, Miyoshi Muscular Dystrophies, Congenital Megaconial Type Muscular Dystrophy, Bethlem Myopathy, Integrin Alpha-7 Deficiency Muscular Dystrophy, Myofibrillar Myopathy, Lmna-Related Congenital Muscular Dystrophy, Congenital Lipodystrophy, X-Linked Myopathy, Progressive Pectorodorsal Muscular Dystrophy, Congenital Merosin-Positive Muscular Dystrophy, Scapulohumeral Muscular Dystrophy, Pseudohypertrophic Muscular Dystrophy, Welander Distal Myopathy, Autosomal Dominant Spinal Muscular Atrophy, Familial Visceral Myopathy, Mabry Type Muscular Dystrophy, Barnes Type Muscular Dystrophy, X-Linked Spinal And Bulbar Muscular Atrophy, Myotonic Dystrophies, and the like. In some instances, the disease causing genetic locus and/or the genetic lesion of a muscular dystrophy for which a replacement gene is supplied through gene therapy is identified in one or more publically available databases of genetic disorders including but not limited to, e.g., the Online Mendelian Inheritance in Man® (OMIM) database maintained by the Johns Hopkins University and available online at www(dot)omim(dot)org.

In some instances, the replacement gene or therapeutic sequence of a gene therapy vector is a dystrophin gene or is derived from a dystrophin gene or engineered based on a dystrophin gene. Such replacement genes may be collectively referred to herein as "dystrophin replacement genes". Dystrophin replacement genes are used in gene therapy of a subject having one or more dysfunctional dystrophin alleles, including but not limited to e.g., those subjects suffering from or having an increased likelihood of being afflicted by DMD, BMD, and the like.

Dystrophin Polypeptides

Dystrophin replacement genes encode one or more dystrophin polypeptides or portions thereof. Generally, dystrophin polypeptides serve as a component of protein complexes (e.g., the dystrophin-associated protein complex (DAPC), dystrophin-glycoprotein complex (DGC), etc.) to anchor the extracellular matrix to the cellular cytoskeleton through F-actin and, in some instances, as a component of protein complexes that act in cell signaling. Components of an assembled dystrophin containing complex and proteins that interact directly or functionally with a dystrophin containing complex include but are not limited to dystrophin, dystroglycans, sarcoglycans, sarcospan, α-dystrobrevins, syntrophins, syncoilin, laminin-2, caveolin-3, proteins of sodium channels, etc. including, e.g., those described in Ehmsen et al. *J Cell Sci* (2002) 115:2801-2803; the disclosure of which is incorporated herein by reference in its entirety.

Dystrophin polypeptides include those polypeptides and portions thereof having homology with one or more known dystrophin proteins, e.g., including those dystrophin proteins identified in *H. sapiens* (e.g., RefSeq: NP_003997.1), *R. norvegicus* (e.g., RefSeq: NP_001005244.1), *X. laevis* (e.g., RefSeq: NP_001084146.1), *M. musculus* (e.g., RefSeq: NP_031894.1), *D. rerio* (e.g., RefSeq: NP_571860.1), *D. melanogaster* (e.g., RefSeq: NP_001036727.1), *C. elegans* (e.g., RefSeq: NP_492946.1), and the like.

In some instances, a dystrophin polypeptide or dystrophin gene may be derived, in part or in whole, from a vertebrate dystrophin gene, including but not limited to, e.g., bird dystrophins, bony fish dystrophins, lizard dystrophins, crocodylia dystrophins, turtle dystrophins, amphibian dystrophins, coelacanth dystrophins, and the like. Vertebrate dystrophins include those polypeptides encoded by vertebrate dystrophin genes including but are not limited to, e.g., *Rattus norvegicus* dystrophin (NCBI GeneID: 24907); *Mus musculus* dystrophin (NCBI GeneID:13405), *Homo sapiens* dystrophin (NCBI GeneID:1756), *Danio rerio* dystrophin (NCBI GeneID:83773), *Gallus gallus* dystrophin (NCBI GeneID:396236), *Sus scrofa* dystrophin (NCBI GeneID:497636), *Xenopus* (Silurana) *tropicalis* dystrophin (NCBI GeneID:493417), *Oryctolagus cuniculus* dystrophin (NCBI GeneID:100355731), *Anolis carolinensis* dystrophin (NCBI GeneID:100557883), *Nannospalax galili* dystrophin (NCBI GeneID:103725389), *Aotus nancymaae* dystrophin (NCBI GeneID:105714758), *Mandrillus leucophaeus* dystrophin (NCBI GeneID:105532517), *Colobus angolensis* palliatus dystrophin (NCBI GeneID:105522567), *Macaca nemestrina* dystrophin (NCBI GeneID:105490348), *Aquila chrysaetos canadensis* dystrophin (NCBI GeneID:105403783), *Pteropus vampyrus* dystrophin (NCBI GeneID:105304409), *Camelus bactrianus* dystrophin (NCBI GeneID:105081023), *Esox lucius* dystrophin (NCBI GeneID:105022562), *Notothenia coriiceps* dystrophin (NCBI GeneID:104966511), *Larimichthys crocea* dystrophin (NCBI GeneID:104929880), *Fukomys damarensis* dystrophin (NCBI GeneID:104851347), *Haliaeetus leucocephalus* dystrophin (NCBI GeneID:104834171), *Corvus cornix cornix* dystrophin (NCBI GeneID:104686213), *Rhinopithecus roxellana* dystrophin (NCBI GeneID:104672934), *Balearica regulorum gibbericeps* dystrophin (NCBI GeneID:104640283), *Phaethon lepturus* dystrophin (NCBI GeneID:104625761), *Caprimulgus carolinensis* dystrophin (NCBI GeneID:104522201), *Buceros rhinoceros silvestris* dystrophin (NCBI GeneID:104498896), *Pterocles gutturalis* dystrophin (NCBI GeneID:104461840), *Chaetura pelagica* dystrophin (NCBI GeneID:104394850), *Opisthocomus hoazin* dystrophin (NCBI GeneID:104338658), *Haliaeetus albicilla* dystrophin (NCBI GeneID:104318552), *Picoides pubescens* dystrophin (NCBI GeneID:104306050), *Charadrius vociferus* dystrophin (NCBI GeneID:104285133), *Apaloderma vittatum* dystrophin (NCBI GeneID:104275657), *Gavia stellata* dystrophin (NCBI GeneID:104264787), *Struthio camelus australis* dystrophin (NCBI GeneID:104151459), *Egretta garzetta* dystrophin (NCBI GeneID:104133073), *Cuculus canorus* dystrophin (NCBI GeneID:104057367), *Nipponia nippon* dystrophin (NCBI GeneID:104020090), *Pygoscelis adeliae* dystrophin (NCBI GeneID:103925972), *Aptenodytes forsteri* dystrophin (NCBI GeneID:103902048), *Serinus canaria* dystrophin (NCBI GeneID:103815902), *Manacus vitellinus* dystrophin (NCBI GeneID:103765876), *Ursus maritimus* dystrophin (NCBI GeneID:103668295), *Corvus brachyrhynchos* dystrophin (NCBI GeneID:103615032), *Galeopterus variegatus* dystrophin (NCBI GeneID:103594405),

*Equus przewalskii* dystrophin (NCBI GeneID:103562210), *Calypte anna* dystrophin (NCBI GeneID:103534395), *Poecilia reticulata* dystrophin (NCBI GeneID:103473963), *Stegastes partitus* dystrophin (NCBI GeneID:103359867), *Eptesicus fuscus* dystrophin (NCBI GeneID:103297853), *Tarsius syrichta* dystrophin (NCBI GeneID:103272458), *Chlorocebus sabaeus* dystrophin (NCBI GeneID: 103231777), *Orycteropus afer afer* dystrophin (NCBI GeneID:103205306), *Poecilia formosa* dystrophin (NCBI GeneID:103147219), *Erinaceus europaeus* dystrophin (NCBI GeneID:103109704), *Lipotes vexillifer* dystrophin (NCBI GeneID:103086365), *Python bivittatus* dystrophin (NCBI GeneID:103059503), *Panthera tigris altaica* dystrophin (NCBI GeneID:102970912), *Chelonia mydas* dystrophin (NCBI GeneID:102930140), *Peromyscus maniculatus bairdii* dystrophin (NCBI GeneID:102918405), *Elephantulus edwardii* dystrophin (NCBI GeneID:102852699), *Alligator mississippiensis* dystrophin (NCBI GeneID: 102566273), *Alligator sinensis* dystrophin (NCBI GeneID: 102371806), *Latimeria chalumnae* dystrophin (NCBI GeneID:102348135), *Pantholops hodgsonii* dystrophin (NCBI GeneID:102344909), *Capra hircus* dystrophin (NCBI GeneID:102168618), *Macaca fascicularis* dystrophin (NCBI GeneID:102141166), *Pseudopodoces humilis* dystrophin (NCBI GeneID:102102544), *Columba livia* dystrophin (NCBI GeneID:102085508), *Zonotrichia albicollis* dystrophin (NCBI GeneID:102061137), *Geospiza fortis* dystrophin (NCBI GeneID:102033021), *Chinchilla lanigera* dystrophin (NCBI GeneID:102027455), *Ictidomys tridecemlineatus* dystrophin (NCBI GeneID:101958964), *Chrysemys picta* dystrophin (NCBI GeneID:101947427), *Falco peregrinus* dystrophin (NCBI GeneID:101918966), *Melopsittacus undulatus* dystrophin (NCBI GeneID:101878899), *Mesocricetus auratus* dystrophin (NCBI GeneID: 101825505), *Ficedula albicollis* dystrophin (NCBI GeneID: 101818554), *Anas platyrhynchos* dystrophin (NCBI GeneID:101802816), *Mustela putorius furo* dystrophin (NCBI GeneID:101672364), *Jaculus jaculus* dystrophin (NCBI GeneID:101611029), *Octodon degus* dystrophin (NCBI GeneID:101582838), *Ochotona princeps* dystrophin (NCBI GeneID:101530539), *Dasypus novemcinctus* dystrophin (NCBI GeneID:101413298), *Trichechus manatus latirostris* dystrophin (NCBI GeneID:101357999), *Oryzias latipes* dystrophin (NCBI GeneID:101167685), *Ovis aries* dystrophin (NCBI GeneID:101114682), *Felis catus* dystrophin (NCBI GeneID:101084937), *Saimiri boliviensis* dystrophin (NCBI GeneID:101028672), *Pan paniscus* dystrophin (NCBI GeneID:100979033), *Cricetulus griseus* dystrophin (NCBI GeneID:100774409), *Cavia porcellus* dystrophin (NCBI GeneID:100727002), *Loxodonta africana* dystrophin (NCBI GeneID:100670372), *Nomascus leucogenys* dystrophin (NCBI GeneID:100580690), *Meleagris gallopavo* dystrophin (NCBI GeneID:100546390), *Ailuropoda melanoleuca* dystrophin (NCBI GeneID:100484758), *Callithrix jacchus* dystrophin (NCBI GeneID:100406331), *Taeniopygia guttata* dystrophin (NCBI GeneID:100228890), *Ornithorhynchus anatinus* dystrophin (NCBI GeneID: 100075838), *Monodelphis domestica* dystrophin (NCBI GeneID:100029652), *Orcinus orca* dystrophin (NCBI GeneID:101274622), *Sarcophilus harrisii* dystrophin (NCBI GeneID:100921237), *Macaca mulatta* dystrophin (NCBI GeneID:707966), and the like.

Dystrophin polypeptides, e.g., used as replacement genes in a gene therapy vector, may be recombinantly or synthetically produced and may vary in their homology with naturally occurring dystrophin polypeptides. As such, a dystrophin polypeptide of the instant disclosure may share 100% or less sequence identity with a naturally occurring dystrophin polypeptide. A dystrophin polypeptide having less than 100% sequence identity with a naturally occurring dystrophin polypeptide may be a modified polypeptide, e.g., recombinantly modified, such that one or more amino acid residues of a naturally occurring dystrophin polypeptide sequence have been modified such that the recombinant dystrophin polypeptide is a non-naturally occurring dystrophin polypeptide.

In some instances, a recombinant dystrophin polypeptide may be encoded from a recombinant dystrophin nucleic acid. Such recombinant dystrophin polypeptides may contain one or more amino acid residue mutations relative to a naturally occurring dystrophin polypeptide. By "mutations" is meant any amino acid reside substitution, deletion or insertion in the primary amino acid sequence relative to a starting dystrophin polypeptide, e.g., a naturally occurring dystrophin polypeptide or other reference dystrophin polypeptide sequence. Amino acid mutations may be generated through synthetic means, e.g., through mutation of a naturally occurring or reference nucleic acid sequence encoding a dystrophin polypeptide. In some instances, a recombinant dystrophin nucleic acid excludes one or more non-coding sequences included in a naturally occurring dystrophin gene or genetic locus. For example, in some instances, a recombinant dystrophin nucleic acid may be a dystrophin cDNA that excludes one or more introns of a dystrophin gene or genetic locus. The number of excluded non-coding sequences in a dystrophin cDNA may vary depending on, e.g., the overall length of the cDNA, the particular dystrophin gene from which the cDNA may be derived, the length of the particular dystrophin from which the cDNA may be derived, the particular isoform from which the cDNA may be derived, the particular dystrophin allele or mutant allele from which the cDNA may be derived, etc., and may range from 1 to 78 or more, including 1 or more including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 or more. In some instances, a dystrophin cDNA may comprise the entire coding region of the dystrophin gene and exclude all non-coding sequences, e.g., all introns and untranslated regions, of the reference gene locus and/or transcript.

In some instances, a dystrophin protein, e.g., as encoded by a dystrophin gene, may be described in terms of sequence similarity and/or sequence identity in relationship to a described amino acid sequence. As such, a dystrophin polypeptide may share up to 100% sequence identity with a particular amino acid sequence, e.g., one or more of the dystrophin amino acid sequences described herein. In some instances, a dystrophin polypeptide may share less than 100% sequence identity to a particular amino acid sequence, e.g., one or more of the dystrophin amino acid sequences described herein, including but not limited to, e.g., at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71% or at least 70% sequence identity with a dystrophin amino acid sequence described herein. In some instances, a dystrophin polypeptide may share no less than 60% sequence identity to one or more of the dystrophin sequences described herein.

In some instances, a dystrophin polypeptide, e.g., as encoded from a dystrophin replacement gene nucleic acid, may share 100% sequence identity with a vertebrate dystrophin polypeptide or less than 100% sequence identity with a vertebrate dystrophin polypeptide including but not limited to at least 75% or more sequence identity, 80% or more sequence identity, 85% or more sequence identity, 90% or more sequence identity, 95% or more sequence identity, 96% or more sequence identity, 97% or more sequence identity, 98% or more sequence identity, 99% or more sequence identity, 99.5% or more sequence identity, 99.9% or more sequence identity, etc.

In some instances, a polypeptide encoded from a replacement gene may include all or a portion of a related or homologous non-dystrophin polypeptide that serves to replace or supplement a diseased, non-functional, or absent dystrophin. Such non-dystrophin polypeptides, as used herein, include polypeptides that are highly related, at least in part, to dystrophin in function and/or primary sequence and include but are not limited to e.g., utrophins. In some instances, a non-dystrophin polypeptide, e.g., as encoded from a dystrophin replacement gene nucleic acid, may share 100% sequence identity with a vertebrate non-dystrophin polypeptide or less than 100% sequence identity with a vertebrate non-dystrophin polypeptide including but not limited to at least 75% or more sequence identity, 80% or more sequence identity, 85% or more sequence identity, 90% or more sequence identity, 95% or more sequence identity, 96% or more sequence identity, 97% or more sequence identity, 98% or more sequence identity, 99% or more sequence identity, 99.5% or more sequence identity, 99.9% or more sequence identity, etc.

In some instances, a dystrophin polypeptide or dystrophin gene may be derived, in part or in whole, from a mammalian dystrophin gene. Mammalian dystrophin genes include placentalia dystrophins, monotremata dystrophins and marsupialia dystrophins. Placentalia dystrophins include those of primates, rodents, even-toes ungulates, carnivores, bats, odd-toed ungulates, insectivores, rabbits and hares, cingulata, macroscelidea, tenrecidae, scandentia, dermoptera, proboscidea, tubulidentata, chrysochloridae, and sirenia. Primate dystrophins include but are not limited to those of baboons (e.g., *Papio papio*, *Papio Anubis*, *Papio cynocephalus*, *Papio hamadryas*, *Papio ursinus* and the like), macaques (e.g., *Macaca fascicularis*, *Macaca nemestrina*, *Macaca mulatta*, and the like), green monkeys (e.g., *Chlorocebus* genus), mangabey (e.g., *Cercocebus agilis*, *Cercocebus galeritus*, *Cercocebus torquatus*, *Cercocebus atys*, *Cercocebus lunulatus*, and the like), patas monkeys (e.g., *Erythrocebus patas*), squirrel monkeys (e.g., *Saimiri sciureus*), species of the family Hominidae (e.g., chimpanzees, gorillas, orangutans, and humans). Rodent dystrophins include but are not limited to those of mouse, rat, squirrel, gopher, vole, hamster, gerbil, guinea pig and the like.

In some instances, a dystrophin polypeptide, e.g., as used in a dystrophin replacement gene therapy, may share 100% sequence identity with a mammalian dystrophin polypeptide. In some instances, a dystrophin polypeptide, e.g., as used in a dystrophin replacement gene therapy, may share less than 100% sequence identity with a mammalian dystrophin polypeptide or a mammalian non-dystrophin polypeptide (e.g., utrophin) including but not limited to at least 75% or more sequence identity, 80% or more sequence identity, 85% or more sequence identity, 90% or more sequence identity, 95% or more sequence identity, 96% or more sequence identity, 97% or more sequence identity, 98% or more sequence identity, 99% or more sequence identity, 99.5% or more sequence identity, 99.9% or more sequence identity, etc.

Mammalian dystrophin polypeptides and non-dystrophin polypeptides of interest include but are not limited to, e.g., those polypeptides having GenBank Accession Numbers: AAA35765.1, AAA35779.1, AAA37530.1, AAA52330.1, AAA53189.1, AAA74506.1, AAA74507.1, AAA74508.1, AAA87068.1, AAB01216.1, AAB02797.1, AAB19347.1, AAB19754.1, AAB20692.1, AAB20693.1, AAB20694.1, AAB20695.1, AAB20696.1, AAB21810.1, AAB21811.1, AAB21812.1, AAB21813.1, AAB22395.2, AAB22396.2, AAB22397.1, AAB22814.1, AAB53001.1, AAB59464.1, AAC31661.1, AAC51631.1, AAC83646.1, AAC98346.1, AAC98347.1, AAD03808.1, AAD03809.1, AAD13820.1, AAD13821.1, AAD13910.1, AAD14085.1, AAD14362.1, AAD14363.1, AAD47295.1, AAF00076.1, AAF59413.1, AAH28720.1, AAH70078.1, AAH94758.1, AAI50142.1, AAL35752.1, AAL61549.1, AAL61550.1, AAL61551.1, AAL61552.1, AAL61553.1, AAL61554.1, AAL61555.1, AAL61556.1, AAL61557.1, AAL61558.1, AAL61559.1, AAL61560.1, AAL61561.1, AAL61562.1, AAL61563.1, AAL61564.1, AAL61565.1, AAL61566.1, AAL61567.1, AAL61568.1, AAL61569.1, AAL61570.1, AAL61571.1, AAL61572.1, AAL61573.1, AAL61574.1, AAL61575.1, AAL61576.1, AAL61577.1, AAL61578.1, AAL61579.1, AAL61580.1, AAL61581.1, AAL61582.1, AAL61583.1, AAL61584.1, AAL61585.1, AAL61586.1, AAL61587.1, AAL61588.1, AAL61589.1, AAL65098.1, AAL65099.1, AAL65100.1, AAN87132.1, AAO46054.1, AAP86212.1, AAP92119.2, AAP92120.2, AAP92121.2, AAS75890.1, ACZ04324.1, ADZ31225.1, ADZ31226.1, AEA76517.1, AER97304.1, AER97305.1, AER97306.1, AEX28223.1, AFE73316.1, AFE75015.1, AFE75016.1, AFE75017.1, AFE75018.1, AFE75019.1, AFE75020.1, AFE75021.1, AFE76990.1, AFH29105.1, AFH31353.1, AFH31354.1, AFI36416.1, AFI36417.1, AGV74356.1, AHY82830.1, AHY82831.1, AHY82832.1, AHY82833.1, AKG49712.1, BAA90413.1, BAA90414.1, BAA90415.1, BAA90416.1, BAA90417.1, BAA90418.1, BAA90419.1, BAA90420.1, BAD92073.1, CAA31452.1, CAA33246.1, CAA38589.1, CAA41157.1, CAD30261.1, CAI26302.1, DAA12694.1, DAA12701.1, DAA12725.1, EAW47845.1, EAW47846.1, EAW47847.1, EAW47848.1, EAW99061.1, EAW99062.1, EAW99063.1, EAW99064.1, EAW99065.1, EAW99066.1, EDL29159.1, EDL96057.1, EDL96058.1, EGW01122.1, EGW01123.1, EGW13991.1, EHB05475.1, ELK13062.1, ELK13063.1, ELK13064.1, ELK32004.1, ELK32005.1, ELK32006.1, ELR53510.1, ELR53512.1, ELR53513.1, ELW48318.1, ELW48319.1, EPQ19100.1, EPQ19101.1, EPQ19102.1, EPQ19105.1, EPQ19106.1, EPY73376.1, EPY73889.1, JAA03380.1, JAA03381.1, JAB18665.1, JAB29803.1, JAB29804.1, JAB29805.1, JAB41839.1, KFO21657.1, KFO21658.1, KFO21660.1, KFO21661.1, KFO21662.1, NP_000100.2, NP_001003343.1, NP_001005244.1, NP_001005246.1, NP_001012408.1, NP_001103554.1, NP_001125766.1, NP_003997.1, NP_004000.1, NP_004001.1, NP_004002.2, NP_004003.1, NP_004004.1, NP_004005.1, NP_004006.1, NP_004007.1, NP_004008.1, NP_004009.1, NP_004010.1, NP_004011.2, NP_004012.1, NP_004013.1, NP_004014.1, NP_031894.1, NP_036830.2, and the like.

In some embodiments of the invention, the dystrophin of interest, e.g., the dystrophin encoded by a replacement gene, is a human dystrophin or portion thereof, including without limitation human dystrophin isoforms Dp427c, Dp427m, Dp427p1, etc. The sequences of human dystrophin are publicly available, e.g. the reference sequence of dystrophin Dp427c isoform is GenBank Accession NP_000100.2 (encoded by GenBank Accession NM_000109.3); the reference sequence of dystrophin Dp427m isoform is GenBank Accession NP_003997.1 (encoded by GenBank Accession NM_004006.2); the reference sequence of dystrophin Dp427p1 isoform is GenBank Accession NP_004000.1 (encoded by GenBank Accession NM_004009.3); the reference sequence of dystrophin Dp427p2 isoform is GenBank Accession NP_004001.1 (encoded by GenBank Accession NM_004010.3); the reference sequence of dystrophin Dp260-1 isoform is GenBank Accession NP_004002.2 (encoded by GenBank Accession NM_004011.3); the reference sequence of dystrophin Dp260-2 isoform is GenBank Accession NP_004003.1 (encoded by GenBank Accession NM_004012.3); the reference sequence of dystrophin Dp140 isoform is GenBank Accession NP_004004.1 (encoded by GenBank Accession NM_004013.2); the reference sequence of dystrophin Dp116 isoform is GenBank Accession NP_004005.1 (encoded by GenBank Accession NM_004014.2); the reference sequence of dystrophin Dp71 isoform is GenBank Accession NP_004006.1 (encoded by GenBank Accession NM_004015.2); the reference sequence of dystrophin Dp71b isoform is GenBank Accession NP_004007.1 (encoded by GenBank Accession NM_004016.2); the reference sequence of dystrophin Dp71a isoform is GenBank Accession NP_004008.1 (encoded by GenBank Accession NM_004017.2); the reference sequence of dystrophin Dp71ab isoform is GenBank Accession NP_004009.1 (encoded by GenBank Accession NM_004018.2); the reference sequence of dystrophin Dp40 isoform is GenBank Accession NP_004010.1 (encoded by GenBank Accession NM_004019.2); the reference sequence of dystrophin Dp140c isoform is GenBank Accession NP_004011.2 (encoded by GenBank Accession NM_004020.3); the reference sequence of dystrophin Dp140b isoform is GenBank Accession NP_004012.1 (encoded by GenBank Accession NM_004021.2); the reference sequence of dystrophin Dp140ab isoform is GenBank Accession NP_004013.1 (encoded by GenBank Accession NM_004022.2); the reference sequence of dystrophin Dp140bc isoform is GenBank Accession NP_004014.1 (encoded by GenBank Accession NM_004023.2); the reference sequence of dystrophin isoform 4 is UniProtID P11532-1; the reference sequence of dystrophin isoform 1 is UniProtID P11532-2; the reference sequence of dystrophin isoform 2 is UniProtID P11532-3; the reference sequence of dystrophin isoform 3 is UniProtID P11532-4; the reference sequence of dystrophin isoform 5 is UniProtID P11532-5; the reference sequence of dystrophin isoform 6 is UniProtID P11532-6; the reference sequence of dystrophin isoform 7 is UniProtID P11532-7; the reference sequence of dystrophin isoform 8 is UniProtID P11532-8; the reference sequence of dystrophin isoform 9 is UniProtID P11532-9 and the reference sequence of dystrophin isoform 10 is UniProtID P11532-10. The ordinary skilled artisan will readily appreciate that, where a replacement gene nucleic acid contains sequence encoding for a disease-related dystrophin isoform, the replacement gene nucleic acid may be modified to correct the genetic lesion or to resemble a functional (i.e., non-disease associated) isoform throughout the entire sequence or at particular locations within the sequence, e.g., at disease associated domains of the sequence.

In some instances, a dystrophin protein, e.g., as encoded by a dystrophin replacement gene, may share 100% sequence identity or less (including but not limited to, e.g., at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71% or at least 70%) with a human dystrophin sequence, including but not limited to, e.g., human dystrophin isoform Dp427c (GenBank Accession NP_000100.2) the amino acid sequence of which is:

```
                                        (SEQ ID NO: 4)
MEDEREDVQKKTFTKWVNAQFSKFGKQHIENLFSDLQDGRRLLDLLEGL

TGQKLPKEKGSTRVHALNNVNKALRVLQNNNVDLVNIGSTDIVDGNHKL

TLGLIWNIILHWQVKNVMKNIMAGLQQTNSEKILLSWVRQSTRNYPQVN

VINFTTSWSDGLALNALIHSHRPDLFDWNSVVCQQSATQRLEHAFNIAR

YQLGIEKLLDPEDVDTTYPDKKSILMYITSLFQVLPQQVSIEAIQEVEM

LPRPPKVTKEEHFQLHHQMHYSQQITVSLAQGYERTSSPKPRFKSYAYT

QAAYVTTSDPTRSPFPSQHLEAPEDKSFGSSLMESEVNLDRYQTALEEV

LSWLLSAEDTLQAQGEISNDVEVVKDQFHTHEGYMMDLTAHQGRVGNIL

QLGSKLIGTGKLSEDEETEVQEQMNLLNSRWECLRVASMEKQSNLHRVL

MDLQNQKLKELNDWLTKTEERTRKMEEEPLGPDLEDLKRQVQQHKVLQE

DLEQEQVRVNSLTHMVVVVDESSGDHATAALEEQLKVLGDRWANICRWT

EDRWVLLQDILLKWQRLTEEQCLFSAWLSEKEDAVNKIHTTGFKDQNEM

LSSLQKLAVLKADLEKKKQSMGKLYSLKQDLLSTLKNKSVTQKTEAWLD

NFARCWDNLVQKLEKSTAQISQAVTTTQPSLTQTTVMETVTTVTTREQI

LVKHAQEELPPPPPQKKRQITVDSEIRKRLDVDITELHSWITRSEAVLQ

SPEFAIFRKEGNFSDLKEKVNAIEREKAEKFRKLQDASRSAQALVEQMV

NEGVNADSIKQASEQLNSRWIEFCQLLSERLNWLEYQNNIIAFYNQLQQ

LEQMTTTAENWLKIQPTTPSEPTAIKSQLKICKDEVNRLSGLQPQIERL

KIQSIALKEKGQGPMFLDADFVAFTNHFKQVFSDVQAREKELQTIFDTL

PPMRYQETMSAIRTWVQQSETKLSIPQLSVTDYEIMEQRLGELQALQSS

LQEQQSGLYYLSTTVKEMSKKAPSEISRKYQSEFEEIEGRWKKLSSQLV

EHCQKLEEQMNKLRKIQNHIQTLKKWMAEVDVFLKEEWPALGDSEILKK

QLKQCRLLVSDIQTIQPSLNSVNEGGQKIKNEAEPEFASRLETELKELN

TQWDHMCQQVYARKEALKGGLEKTVSLQKDLSEMHEWMTQAEEEYLERD

FEYKTPDELQKAVEEMKRAKEEAQQKEAKVKLLTESVNSVIAQAPPVAQ

EALKKELETLTTNYQWLCTRLNGKCKTLEEVWACWHELLSYLEKANKWL

NEVEFKLKTTENIPGGAEEISEVLDSLENLMRHSEDNPNQIRILAQTLT

DGGVMDELINEELETFNSRWRELHEEAVRRQKLLEQSIQSAQETEKSLH

LIQESLTFIDKQLAAYIADKVDAAQMPQEAQKIQSDLTSHEISLEEMKK

HNQGKEAAQRVLSQIDVAQKKLQDVSMKFRLFQKPANFEQRLQESKMIL

DEVKMHLPALETKSVEQEVVQSQLNHCVNLYKSLSEVKSEVEMVIKTGR

QIVQKKQTENPKELDERVTALKLHYNELGAKVTERKQQLEKCLKLSRKM

RKEMNVLTEWLAATDMELTKRSAVEGMPSNLDSEVAWGKATQKEIEKQK

VHLKSITEVGEALKTVLGKKETLVEDKLSLLNSNWIAVTSRAEEWLNLL
```

LEYQKHMETFDQNVDHITKWIIQADTLLDESEKKKPQQKEDVLKRLKAE
LNDIRPKVDSTRDQAANLMANRGDHCRKLVEPQISELNHRFAAISHRIK
TGKASIPLKELEQFNSDIQKLLEPLEAEIQQGVNLKEEDFNKDMNEDNE
GTVKELLQRGDNLQQRITDERKREEIKIKQQLLQTKHNALKDLRSQRRK
KALEISHQWYQYKRQADDLLKCLDDIEKKLASLPEPRDERKIKEIDREL
QKKKEELNAVRRQAEGLSEDGAAMAVEPTQIQLSKRWREIESKFAQFRR
LNFAQIHTVREETMMVMTEDMPLEISYVPSTYLTEITHVSQALLEVEQL
LNAPDLCAKDFEDLFKQEESLKNIKDSLQQSSGRIDIIHSKKTAALQSA
TPVERVKLQEALSQLDFQWEKVNKMYKDRQGRFDRSVEKWRRFHYDIKI
FNQWLTEAEQFLRKTQIPENWEHAKYKWYLKELQDGIGQRQTVVRTLNA
TGEEIIQQSSKTDASILQEKLGSLNLRWQEVCKQLSDRKKRLEEQKNIL
SEFQRDLNEFVLWLEEADNIASIPLEPGKEQQLKEKLEQVKLLVEELPL
RQGILKQLNETGGPVLVSAPISPEEQDKLENKLKQTNLQWIKVSRALPE
KQGEIEAQIKDLGQLEKKLEDLEEQLNHLLLWLSPIRNQLEIYNQPNQE
GPFDVQETEIAVQAKQPDVEEILSKGQHLYKEKPATQPVKRKLEDLSSE
WKAVNRLLQELRAKQPDLAPGLTTIGASPTQTVTLVTQPVVTKETAISK
LEMPSSLMLEVPALADFNRAWTELTDWLSLLDQVIKSQRVMVGDLEDIN
EMIIKQKATMQDLEQRRPQLEELITAAQNLKNKTSNQEARTIITDRIER
IQNQWDEVQEHLQNRRQQLNEMLKDSTQWLEAKEEAEQVLGQARAKLES
WKEGPYTVDAIQKKITETKQLAKDLRQWQTNVDVANDLALKLLRDYSAD
DTRKVHMITENINASWRSIHKRVSEREAALEETHRLLQQFPLDLEKFLA
WLTEAETTANVLQDATRKERLLEDSKGVKELMKQWQDLQGEIEAHTDVY
HNLDENSQKILRSLEGSDDAVLLQRRLDNMNFKWSELRKKSLNIRSHLE
ASSDQWKRLHLSLQELLVWLQLKDDELSRQAPIGGDFPAVQKQNDVHRA
FKRELKTKEPVIMSTLETVRIFLTEQPLEGLEKLYQEPRELPPEERAQN
VTRLLRKQAEEVNTEWEKLNLHSADWQRKIDETLERLQELQEATDELDL
KLRQAEVIKGSWQPVGDLLIDSLQDHLEKVKALRGEIAPLKENVSHVND
LARQLTTLGIQLSPYNLSTLEDLNTRWKLLQVAVEDRVRQLHEAHRDFG
PASQHFLSTSVQGPWERAISPNKVPYYINHETQTTCWDHPKMTELYQSL
ADLNNVRFSAYRTAMKLRRLQKALCLDLLSLSAACDALDQHNLKQNDQP
MDILQIINCLTTIYDRLEQEHNNLVNVPLCVDMCLNWLLNVYDTGRTGR
IRVLSFKTGIISLCKAHLEDKYRYLFKQVASSTGFCDQRRLGLLLHDSI
QIPRQLGEVASFGGSNIEPSVRSCFQFANNKPEIEAALFLDWMRLEPQS
MVWLPVLHRVAAAETAKHQAKCNICKECPIIGFRYRSLKHFNYDICQSC
FFSGRVAKGHKMHYPMVEYCTPTTSGEDVRDFAKVLKNKFRTKRYFAKH
PRMGYLPVQTVLEGDNMETPVTLINFWPVDSAPASSPQLSHDDTHSRIE
HYASRLAEMENSNGSYLNDSISPNESIDDEHLLIQHYCQSLNQDSPLSQ
PRSPAQILISLESEERGELERILADLEEENRNLQAEYDRLKQQHEHKGL
SPLPSPPEMMPTSPQSPRDAELIAEAKLLRQHKGRLEARMQILEDHNKQ
LESQLHRLRQLLEQPQAEAKVNGTTVSSPSTSLQRSDSSQPMLLRVVGS

QTSDSMGEEDLLSPPQDTSTGLEEVMEQLNNSFPSSRGRNTPGKPMRED
TM or human dystrophin isoform 4 (UniProtID P11532-1) the amino acid sequence of which is:

(SEQ ID NO: 5)
MLWWEEVEDCYEREDVQKKTFTKWVNAQFSKFGKQHIENLFSDLQDGRR
LLDLLEGLTGQKLPKEKGSTRVHALNNVNKALRVLQNNNVDLVNIGSTD
IVDGNHKLTLGLIWNIILHWQVKNVMKNIMAGLQQTNSEKILLSWVRQS
TRNYPQVNVINFTTSWSDGLALNALIHSHRPDLFDWNSVVCQQSATQRL
EHAFNIARYQLGIEKLLDPEDVDTTYPDKKSILMYITSLFQVLPQQVSI
EAIQEVEMLPRPPKVTKEEHFQLHHQMHYSQQITVSLAQGYERTSSPKP
RFKSYAYTQAAYVTTSDPTRSPFPSQHLEAPEDKSFGSSLMESEVNLDR
YQTALEEVLSWLLSAEDTLQAQGEISNDVEVVKDQFHTHEGYMMDLTAH
QGRVGNILQLGSKLIGTGKLSEDEETEVQEQMNLLNSRWECLRVASMEK
QSNLHRVLMDLQNQKLKELNDWLTKTEERTRKMEEEPLGPDLEDLKRQV
QQHKVLQEDLEQEQVRVNSLTHMVVVVDESSGDHATAALEEQLKVLGDR
WANICRWTEDRWVLLQDILLKWQRLTEEQCLFSAWLSEKEDAVNKIHTT
GFKDQNEMLSSLQKLAVLKADLEKKKQSMGKLYSLKQDLLSTLKNKSVT
QKTEAWLDNFARCWDNLVQKLEKSTAQISQAVTTTQPSLTQTTVMETVT
TVTTREQILVKHAQEELPPPPPQKKRQITVDSEIRKRLDVDITELHSWI
TRSEAVLQSPEFAIFRKEGNFSDLKEKVNAIEREKAEKFRKLQDASRSA
QALVEQMVNEGVNADSIKQASEQLNSRWIEFCQLLSERLNWLEYQNNII
AFYNQLQQLEQMTTTAENWLKIQPTTPSEPTAIKSQLKICKDEVNRLSD
LQPQIERLKIQSIALKEKGQGPMFLDADFVAFTNHFKQVFSDVQAREKE
LQTIFDTLPPMRYQETMSAIRTWVQQSETKLSIPQLSVTDYEIMEQRLG
ELQALQSSLQEQQSGLYYLSTTVKEMSKKAPSEISRKYQSEFEEIEGRW
KKLSSQLVEHCQKLEEQMNKLRKIQNHIQTLKKWMAEVDVFLKEEWPAL
GDSEILKKQLKQCRLLVSDIQTIQPSLNSVNEGGQKIKNEAEPEFASRL
ETELKELNTQWDHMCQQVYARKEALKGGLEKTVSLQKDLSEMHEWMTQA
EEEYLERDFEYKTPDELQKAVEEMKRAKEEAQQKEAKVKLLTESVNSVI
AQAPPVAQEALKKELETLTTNYQWLCTRLNGKCKTLEEVWACWHELLSY
LEKANKWLNEVEFKLKTTENIPGGAEEISEVLDSLENLMRHSEDNPNQI
RILAQTLTDGGVMDELINEELETFNSRWRELHEEAVRRQKLLEQSIQSA
QETEKSLHLIQESLTFIDKQLAAYIADKVDAAQMPQEAQKIQSDLTSHE
ISLEEMKKHNQGKEAAQRVLSQIDVAQKKLQDVSMKFRLFQKPANFEQR
LQESKMILDEVKMHLPALETKSVEQEVVQSQLNHCVNLYKSLSEVKSEV
EMVIKTGRQIVQKKQTENPKELDERVTALKLHYNELGAKVTERKQQLEK
CLKLSRKMRKEMNVLTEWLAATDMELTKRSAVEGMPSNLDSEVAWGKAT
QKEIEKQKVHLKSITEVGEALKTVLGKKETLVEDKLSLLNSNWIAVTSR
AEEWLNLLLEYQKHMETFDQNVDHITKWIIQADTLLDESEKKKPQQKED

```
-continued
VLKRLKAELNDIRPKVDSTRDQAANLMANRGDHCRKLVEPQISELNHRF

AAISHRIKTGKASIPLKELEQFNSDIQKLLEPLEAEIQQGVNLKEEDFN

KDMNEDNEGTVKELLQRGDNLQQRITDERKREEIKIKQQLLQTKHNALK

DLRSQRRKKALEISHQWYQYKRQADDLLKCLDDIEKKLASLPEPRDERK

IKEIDRELQKKKEELNAVRRQAEGLSEDGAAMAVEPTQIQLSKRWREIE

SKFAQFRRLNFAQIHTVREETMMVMTEDMPLEISYVPSTYLTEITHVSQ

ALLEVEQLLNAPDLCAKDFEDLFKQEESLKNIKDSLQQSSGRIDIIHSK

KTAALQSATPVERVKLQEALSQLDFQWEKVNKMYKDRQGRFDRSVEKWR

RFHYDIKIFNQWLTEAEQFLRKTQIPENWEHAKYKWYLKELQDGIGQRQ

TVVRTLNATGEEIIQQSSKTDASILQEKLGSLNLRWQEVCKQLSDRKKR

LEEQKNILSEFQRDLNEFVLWLEEADNIASIPLEPGKEQQLKEKLEQVK

LLVEELPLRQGILKQLNETGGPVLVSAPISPEEQDKLENKLKQTNLQWI

KVSRALPEKQGEIEAQIKDLGQLEKKLEDLEEQLNHLLLWLSPIRNQLE

IYNQPNQEGPFDVKETEIAVQAKQPDVEEILSKGQHLYKEKPATQPVKR

KLEDLSSEWKAVNRLLQELRAKQPDLAPGLTTIGASPTQTVTLVTQPVV

TKETAISKLEMPSSLMLEVPALADFNRAWTELTDWLSLLDQVIKSQRVM

VGDLEDINEMIIKQKATMQDLEQRRPQLEELITAAQNLKNKTSNQEART

IITDRIERIQNQWDEVQEHLQNRRQQLNEMLKDSTQWLEAKEEAEQVLG

QARAKLESWKEGPYTVDAIQKKITETKQLAKDLRQWQTNVDVANDLALK

LLRDYSADDTRKVHMITENINASWRSIHKRVSEREAALEETHRLLQQFP

LDLEKFLAWLTEAETTANVLQDATRKERLLEDSKGVKELMKQWQDLQGE

IEAHTDVYHNLDENSQKILRSLEGSDDAVLLQRRLDNMNFKWSELRKKS

LNIRSHLEASSDQWKRLHLSLQELLVWLQLKDDELSRQAPIGGDFPAVQ

KQNDVHRAFKRELKTKEPVIMSTLETVRIFLTEQPLEGLEKLYQEPREL

PPEERAQNVTRLLRKQAEEVNTEWEKLNLHSADWQRKIDETLERLQELQ

EATDELDLKLRQAEVIKGSWQPVGDLLIDSLQDHLEKVKALRGEIAPLK

ENVSHVNDLARQLTTLGIQLSPYNLSTLEDLNTRWKLLQVAVEDRVRQL

HEAHRDFGPASQHFLSTSVQGPWERAISPNKVPYYINHETQTTCWDHPK

MTELYQSLADLNNVRFSAYRTAMKLRRLQKALCLDLLSLSAACDALDQH

NLKQNDQPMDILQIINCLTTIYDRLEQEHNNLVNVPLCVDMCLNWLLNV

YDTGRTGRIRVLSFKTGIISLCKAHLEDKYRYLFKQVASSTGFCDQRRL

GLLLHDSIQIPRQLGEVASFGGSNIEPSVRSCFQFANNKPEIEAALFLD

WMRLEPQSMVWLPVLHRVAAAETAKHQAKCNICKECPIIGFRYRSLKHF

NYDICQSCFFSGRVAKGHKMHYPMVEYCTPTTSGEDVRDFAKVLKNKFR

TKRYFAKHPRMGYLPVQTVLEGDNMETPVTLINFWPVDSAPASSPQLSH

DDTHSRIEHYASRLAEMENSNGSYLNDSISPNESIDDEHLLIQHYCQSL

NQDSPLSQPRSPAQILISLESEERGELERILADLEEENRNLQAEYDRLK

QQHEHKGLSPLPSPPEMMPTSPQSPRDAELIAEAKLLRQHKGRLEARMQ

ILEDHNKQLESQLHRLRQLLEQPQAEAKVNGTTVSSPSTSLQRSDSSQP

MLLRVVGSQTSDSMGEEDLLSPPQDTSTGLEEVMEQLNNSFPSSRGRNT

PGKPMREDTM.
```

In some instances, a dystrophin polypeptide or a nucleic acid encoding a dystrophin polypeptide may include or exclude all or a portion of a domain of the dystrophin protein. Domains of dystrophin include but are not limited to topological, homology, and/or functional domains. Such domains include but are not limited to, e.g., actin-binding domains, e.g., from amino acids 1 to 240 of UniProtID P11532; calponin-homology domains, e.g., from amino acids 15 to 199 and 134-237 of UniProtID P11532; spectrin repeat domains, e.g., from amino acids 339-447, 448-556, 559-667, 719-828, 830-934, 943-1045, 1048-1154, 1157-1263, 1266-1367, 1368-1463, 1468-1568, 1571-1676, 1679-1778, 1779-1874, 1877-1979, 1992-2101, 2104-2208, 2211-2318, 2319-2423, 2475-2577, 2580-2686, 2689-2802, 2808-2930 and 2935-3040 of UniProtID P11532; WW/rsp5/WWP domains, e.g., from amino acids 3055-3088 of UniProtID P11532; and the like.

In some instances, a dystrophin polypeptide or a nucleic acid encoding a dystrophin polypeptide may include or exclude one or more modification sites of the dystrophin protein. Modification sites may include but are not limited to, e.g., phosphorylation sites, glycosylation sites, etc. Such sites may include but are not limited to the following phosphoserine sites relative to the sequence of UniProtID P11532: residue 3483, residue 3490, residue 3500, residue 3612, residue 3613, residue 3617, residue 3623, residue 3624 and residue 3666. In some instances, a dystrophin polypeptide may include or exclude one or more post-translational modifications.

In some instances, a dystrophin polypeptide, i.e., of a dystrophin replacement gene therapy, include a minidystrophin or a microdystrophin and, accordingly, a replacement gene nucleic acid may contain a miniaturized dystrophin expression cassettes and a nucleic acid of a tolerizing vector may include nucleic acid encoding a minidystrophin or microdystrophin or portion thereof. Minidystrophins and micro dystrophins may comprise one or more deletions relative to a full-length dystrophin isoform and therefore may exclude one or more dystrophin domains or portions thereof (including but not limited to e.g., those dystrophin domains described herein) resulting in a shortened dystrophin polypeptide relative to a full-length dystrophin. Minidystrophins and microdystrophins, whether naturally occurring or synthetically derived or recombinantly modified, generally maintain critical functional domains or critical portions thereof and thus retain at least partial function as compared to full-length dystrophin isoforms. For example, in some instances, minidystrophins and microdystrophins maintain particular binding functionality, through the maintenance of associated binding domains, including but not limited to e.g., actin binding, dystroglycan binding, dystrobrevin binding, syntrophin binding, etc. In some instances, where a minidystrophin or microdystrophin is derived by modification of a nucleic acid sequence of a full-length dystrophin isoform, e.g., through deletion mutation (whether naturally or artificially introduced), the modification occurs or is configured to occur in such a manner that the nucleic acid sequence prior to and following the modification remains "in frame", i.e., that both the sequence before and after the mutation is capable of encoding polypeptide, e.g., without the introduction of a premature stop codon or missense mutation.

The term "minidystrophin", as used herein, generally refers to an internally deleted but functional dystrophin isoform, including, e.g., naturally occurring shortened but functional dystrophin isoforms and synthetic dystrophin isoforms derived from or based on naturally occurring shortened but functional dystrophin isoforms. For example, in some instances, a minidystrophin includes an N-terminal dystrophin domain (i.e., an actin binding domain) and a dystrophin cysteine rich domain but excludes one or more dystrophin rod domains or spectrin-like repeat domains or hinge region domains or the C-terminal domain or a WW domain or a ZZ domain or a coiled-coil domain or some combination thereof. In some instances, a minidystrophin may specifically include one or more dystrophin rod domains or spectrin-like repeat domains or hinge region domains or the C-terminal domain or a WW domain or a ZZ domain or a coiled-coil domain or some combination thereof.

In some instances, minidystrophins include those shortened but functional dystrophin polypeptide isoforms and nucleic acids encoding such polypeptides as described in Love D R, et al. (1990) Am J Med Genet 37(1):136-42; England S B, et al. (1990) Nature 343(6254):180-2; Ragot T, et al., (1993) Nature 361(6413):647-50; Vincent N, et al., (1993) Nat Genet 5(2):130-4; Wells D J, et al., (1995) Hum Mol Genet 4(8):1245-50; Wang B, et al., (2000) Proc Natl Acad Sci USA 97(25):13714-9; Watchko J, et al., (2002) Hum Gene Ther 13(12):1451-60; Li S, et al., (2005) Gene Ther 12(14):1099-108; Liang Y, et al., (2005) Zhonghua Yi Xue Yi Chuan Xue Za Zhi 22(5):493-6; Vandebrouck A, et al., (2006) FASEB J 20(1):136-8; Friedrich O, et al., (2008) Biophys J 94(12):4751-65; Wang B, et al., (2008) Gene Ther 15(15):1099-106; Wang B, et al., (2009) J Orthop Res 27(4):421-6; Yang J, et al., (2009) Acta Biochim Biophys Sin (Shanghai) 41(12):1053-60; Koppanati B M, et al., (2010) Gene Ther 17(11):1355-62; Reay D P, et al., (2012) Mol Med 18:466-76; Clemens P R, et al. (1995) Hum Gene Ther 6(11):1477-85; Harper S Q, et al. (2002) Nat Med 8(3):253-61; Lai Y, et al. J Clin Invest 119(3):624-35. and Zhang Y, et al. (2012) Hum Gene Ther 23(1): 98-103, the disclosures of which are incorporated herein by reference in their entirety.

The term "microdystrophin", as used herein, generally refers to a shortened, relative to full-length dystrophin isoforms, but functional dystrophin polypeptide, including, e.g., a shorted but functional dystrophin polypeptide or dystrophin isoform, including, e.g., naturally occurring shortened or truncated but functional dystrophin isoforms and synthetic shortened or truncated but functional dystrophins. Microdystrophins may be partially or wholly synthetic or recombinantly derived and will contain some combination of critical dystrophin domains or sequence based on critical dystrophin domains, including but not limited to, e.g., an actin binding domain (e.g., N-terminal actin binding domain) and a cysteine-rich domain. As such, relative to a full-length dystrophin isoform or other naturally occurring dystrophin isoform, a microdystrophin may exclude one or more dystrophin domains including but not limited to, e.g., a hinge region domain, a spectrin-like repeat domain, a non-terminal actin binding domain, a C-terminal domain, and the like. In some instances, a microdystrophin will specifically include one or more non-critical domains including but not limited to, e.g., a hinge region domain, a spectrin-like repeat domain, a non-terminal actin binding domain, a C-terminal domain, and the like.

Microdystrophin polypeptides and nucleic acids encoding microdystrophin include but are not limited to, e.g., those described in Fabb S A, et al. (2002) Hum Mol Genet 11(7):733-41; Sakamoto M, et al. (2002) Biochem Biophys Res Commun 293(4):1265-72; Roberts M L, et al. (2002) Hum Mol Genet 11(15):1719-30; Yue Y, et al. (2003) Circulation 108(13):1626-32; Bachrach E, et al. (2004) Proc Natl Acad Sci USA 101(10):3581-6; Yoshimura M, et al. (2004) Mol Ther 10(5):821-8; Liu M, et al. (2005) Mol Ther 11(2):245-56; Weisbart R H, et al. (2005) J Drug Target 13(2):81-7; Abmayr S, et al. (2005) Mol Ther 12(3):441-50; Yue Y, et al. (2006) Mol Ther 14(1):79-87; Gregorevic P, et al. (2006) Nat Med 12(7):787-9; Townsend D, et al. (2007) Mol Ther 15(6):1086-92; Xiong F, et al. (2007) Hum Gene Ther 18(6):490-501; Xiong F, et al. (2007) BMC Neurosci 8:50; Percival J M, et al. (2007) Traffic 8(10):1424-39; Ikemoto M, et al. (2007) Mol Ther 15(12):2178-85; Rodino-Klapac L R, et al. (2007) J Transl Med 5:45; Gregorevic P, et al. (2008) Mol Ther 16(4):657-64; Bostick B, et al. (2008) Hum Gene Ther 19(8):851-6; Foster H, et al. (2008) Mol Ther 16(11):1825-32; Jorgensen L H, et al. (2009) Hum Gene Ther 20(6):641-50; Rodino-Klapac L R, et al. (2010) Mol Ther 18(1):109-17; Pichavant C, et al. (2010) Mol Ther 18(5):1002-9; Xiong F, et al. (2010) Transplant Proc 42(7): 2731-9; Athanasopoulos T, et al. (2011) Methods Mol Biol 709:21-37; Shin J H, et al. (2011) Gene Ther 18(9):910-9; Koo T, et al. (2011) Hum Gene Ther 22(11):1379-88; Bostick B, et al. (2011) Mol Ther 19(10):1826-32; Shin J H, et al. (2012) Hum Gene Ther 23(2):202-9; Koo T, et al. (2011) J Gene Med 13(9):497-506; Schinkel S, et al. (2012) Hum Gene Ther 23(6):566-75; Feng S W, et al. (2012) Biochem Biophys Res Commun 419(1):1-6; Bostick B, et al. (2012) J Mol Cell Cardiol 53(2):217-22; Shin J H, et al. (2013) Mol Ther 21(4):750-7; Benabdallah B F, et al. (2013) Mol Ther Nucleic Acids 2:e68; Rodino-Klapac L R, et al. (2013) Hum Mol Genet 22(24):4929-37; Chicoine L G, et al. (2014) Mol Ther 22(2):338-47 and Hayashita-Kinoh H, et al. (2015) Mol Ther 23(4):627-37, the disclosures of which are incorporated herein by reference in their entirety.

In some instances, a microdystrophin utilized as a replacement gene and/or as part of a tolerizing vector may be a microdystrophin lacking spectrin-like repeats 4 to 23. In some instances, a microdystrophin utilized as a replacement gene and/or as part of a tolerizing vector may be a microdystrophin lacking hinge region 3. In some instances, a microdystrophin utilized as a replacement gene and/or as part of a tolerizing vector may be a microdystrophin lacking a combination of spectrin-like repeats 4 to 23 and hinge region 3.

In some instances, a dystrophin replacement polypeptide may be a hybrid dystrophin polypeptide. Hybrid dystrophin polypeptides include but are not limited to polypeptides that include, in a single dystrophin construct, sequence and/or domains from two or more different dystrophin polypeptides, different dystrophin isoforms, or different related but non-dystrophin polypeptides. As such, a hybrid dystrophin may contain any assemblage of domains and/or sequence provided the hybrid dystrophin provides at least partial function of native dystrophin and/or can restore the structural or signaling functions of a dysfunctional dystrophin, and reduce at least one symptom of a dystrophin related muscular dystrophy. For example, in some instances, a hybrid dystrophin may contain dystrophin domains or sequences from two more dystrophins derived from different species of animals, e.g., different vertebrates, different mammals, different primates, etc. In some instances, a hybrid dystrophin may contain dystrophin domains or sequences from two more dystrophins derived from different dystrophin isoforms from the same or different species of animal. In some instances, a hybrid dystrophin may contain one or more dystrophin domains or sequences derived from a dystrophin polypeptide and one or more domains or sequences derived from a non-dystrophin polypeptide, e.g., a utrophin or other polypeptide related in structure or function.

In some instances, a dystrophin (including e.g., dystrophins, dystrophin fragments, microdystrophins, minidystrophins, etc.) of the instant disclosure may include those dystrophins that have been, are, or are in preparation for a human clinical trial for the treatment of human subjects, including human subjects afflicted by muscular dystrophy, including but not limited to ClinicalTrials(dot)gov identifiers NCT02376816 (Clinical Intramuscular Gene Transfer Trial of rAAVrh74.MCK.Micro-Dystrophin to Patients With Duchenne Muscular Dystrophy, rAAVrh74.MCK.micro-Dystrophin) and NCT00428935 (Safety Study of Mini-dystrophin Gene to Treat Duchenne Muscular Dystrophy, rAAV2.5-CMV-minidystrophin (d3990)). In some instances, a dystrophin (including e.g., dystrophins, dystrophin fragments, microdystrophins, minidystrophins, etc.) of the instant disclosure may include those dystrophins described in US Patent Publication No. 20050158281 A1, the disclosure of which is incorporated herein by reference in its entirety.

In some instances, a dystrophin polypeptide, e.g., as encoded from a nucleic acid of the subject disclosure, may include a portion of a full length dystrophin amino acid sequence, e.g., a dystrophin amino acid sequence disclosed herein. The length of such portions of dystrophin amino acid sequence may vary and may range, e.g., from 5 to 3684 amino acids in length, including, e.g., 5-10, 10-20, 20-30, 30-40, 40-50, 50-60, 60-70, 70-80, 80-90, 90-100, 100-200, 200-300, 300-400, 400-500, 500-600, 600-700, 700-800, 800-900, 900-1000, 1000-1500, 1000-2000, 1000-2500, 1000-3000 and 1000-3500 residues in length. In some instances, such polypeptide portions of a dystrophin may include specific amino acid residues relative to a human dystrophin sequence where the first amino acid of the polypeptide portion may range from residues 1-3680 of UniProtID P11532 and the last amino acid of the polypeptide portion may range from residues 5-3685 of UniProtID P11532 and the polypeptide portion may include or exclude any particular protein feature(s), e.g., domains or portions thereof or modified residues, including but not limited to those described above.

In some instances, modification of a dystrophin polypeptide, including e.g., selection of amino acid mutations, amino acid deletions, and/or amino acid insertion sites, may be performed based on the three-dimensional structure of the dystrophin polypeptide. For example, in some instances, a modified dystrophin polypeptide and/or a nucleic acid encoding a modified dystrophin polypeptide may be based on rational design of the modified dystrophin polypeptide three-dimensional structure. Rational design of modified dystrophin polypeptides may be achieved through use of one or more three-dimensional dystrophin protein structures including but not limited to, e.g., RCSP Protein Data Bank (PDB) structures 1DXX_A, 1DXX_B, 1DXX_C, 1DXX_D, 1EG3_A, 1EG4_A, 1QAG_A, 1QAG_B, 3UUN_A, 3UUN_B, and the like.

In some instances, a dystrophin nucleic acid, e.g., as provided as a dystrophin replacement gene, may be derived from human dystrophin nucleotide sequence, e.g., including but not limited to those dystrophin transcript reference sequences disclosed herein and portions thereof.

In some instances, a nucleic acid as described herein may be appended with one or more additional nucleic acids or one or more additional nucleotides. Additional nucleic acid may be appended to the described nucleic acids for a variety of purposes including but not limited to, e.g., cloning purposes (e.g., to facilitate homologous recombination, to facilitate ligation, etc.). As such, in some instances a nucleic acid as described herein may be appended with one or more additional nucleic acids to attach one or more nucleic acid spacers, one or more homologous sequences (e.g., a sequence homologous with a vector into which the subject nucleic acid may be cloned), one or more restriction enzyme recognition sites, and the like. Additional sequences appended to a subject nucleic acid may be added through any convenient method including but not limited to, e.g., ligation-based methods, PCR-based methods, de novo polynucleotide synthesis, etc.

Methods and Compositions
Methods of Treating

Aspects of the disclosure include methods and compositions for repressing an immune response to a gene therapy, e.g., a muscle dystrophy replacement gene therapy, in a subject. Because such methods can be used to treat a subject, such methods can also be referred to as methods of treating an individual for an immune response to a gene therapy. Aspects of the subject methods generally involve the administration of a therapeutically effective amount of a tolerizing vector, as described herein, to a subject in need thereof.

A "therapeutically effective amount" or "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of tolerizing vector (e.g., dystrophy replacement gene tolerizing vector, and the like) and/or compositions (e.g., tolerizing vector compositions (e.g., replacement gene tolerizing vaccines)) is an amount that is sufficient, when administered to (e.g., injected into, delivered intravenously, etc.) the individual, to palliate, ameliorate, stabilize, reverse, prevent, slow or delay the progression of the immune response to the gene therapy (e.g., a component of the gene therapy vehicle, the replacement gene, etc.). Administration of an effective amount of a tolerizing vector may, for example, result in reducing the subject's general immune activity, reducing the subject's specific immune response, reducing the subject's immune response to a polypeptide encoded from a replacement gene, reducing the subject's immune response to a component of the gene therapy vehicle, or some combination thereof. In some instances, an effective amount reduces one or more symptoms of the immune response to the gene therapy (including but not limited to, e.g., inflammation, reduced effectiveness of the gene therapy, etc.).

In some instances, a therapeutically effective dose, whether delivered in a single administration or multiple administrations, of a tolerizing vector may remain effective for an extended period of time, e.g., by nature of the extended transient expression of the encoded polypeptide. The extended time period during which an administered therapeutically effective dose of a tolerizing vector may remain effective will vary and may range from days to weeks including but not limited to, e.g., 2-3 days, 3-4 days, 4-5 days, 5-6 days, 6-7 days, 2-5 days, 3-6 days, 4-7 days, 1 week to 2 weeks, 2 weeks to 3 weeks, 3 weeks to 4 weeks, 1 week to 3 weeks, 2 weeks to 4 weeks, 1 week to 4 weeks, etc.

Tolerizing vectors, as described herein, may be configured for enhanced expression, e.g., through the use of one or more vector specific elements (i.e., promoters, enhancers, introns, etc.) as described herein and/or known to the ordinary skilled artisan. However, the administered tolerizing therapy is generally performed such that the tolerizing gene of the vector is expressed at a low level as compared to the expression of the replacement gene of the gene therapy vector to which the subject may mount an immune response. The desired ratio of low expression of the tolerizing gene to high expression of the replacement gene may be achieved by any convenient means or combination thereof. As a non-limiting example, relatively low expression of the tolerizing gene to the replacement gene may be achieved through the use of different vectors with generally different average expression levels, e.g., in some embodiments, a tolerizing gene may be expressed from a bacterial vector having generally lower expression as compared to the expression of a replacement gene expressed from a viral vector. In some instances, lower expression of the tolerizing vector may be achieved by administering the tolerizing vector at a reduced dosage as compared to the gene therapy vector. In some instances, lower expression of the tolerizing vector may be achieved by administering the gene therapy vector at an elevated dosage as compared to the tolerizing vector. In some instances, relatively low expression of the tolerizing vector as compared to the gene therapy vector may be achieved by using a less efficient route of delivery for the tolerizing vector as compared to the gene therapy vector. Modulation of relative vector expression levels to a desired ratio to optimize a treatment regimen as described herein is within the skill of the relevant practitioner.

The terms "treatment", "treating", "treat" and the like are used herein to generally refer to obtaining a desired pharmacologic and/or physiologic effect. The effect can be prophylactic in terms of completely or partially preventing a disease (wherein the term "disease" may encompass an immune response to a gene therapy) or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s). Those in need of treatment can include those already inflicted (e.g., those with already having an immune response to gene therapy) as well as those in which prevention is desired (e.g., those that will receive gene therapy, those that will receive muscle dystrophy gene therapy, those that have an increased likelihood of having an immune response to gene therapy, those that have an increased likelihood of having an immune response to muscle dystrophy gene therapy, those having one or more risk factors for developing an immune response to a gene therapy, those with one or more risk factors for developing an immune response to a muscle dystrophy gene therapy, etc.).

A therapeutic treatment is one in which the subject is inflicted prior to administration and a prophylactic treatment is one in which the subject is not inflicted prior to administration. With respect to relapsing conditions, a prophylactic treatment may include a treatment administered to a subject with a diagnosed condition in a remitting state, e.g., to prevent a relapse of the condition or to prevent the reoccurrence of one or more symptoms of the condition (e.g., to prevent the reoccurrence or relapse of an immune response to a gene therapy after being treated for an immune response to a gene therapy). In some embodiments, the subject has an increased likelihood of becoming inflicted or is suspected of having an increased likelihood of becoming inflicted (e.g., relative to a standard, e.g., relative to the average individual, e.g., a subject may have a genetic predisposition to developing an immune response to gene therapy and/or a family history indicating increased risk of developing an immune response to a gene therapy), in which case the treatment can be a prophylactic treatment.

In some embodiments, the individual to be treated is an individual undergoing muscle dystrophy gene therapy or in need of muscle dystrophy gene therapy including but not limited to virus mediated muscle dystrophy gene therapy (e.g., adenovirus mediated gene therapy, adeno-associated virus mediated gene therapy (e.g., adeno-associated virus type 6 (AAV6) mediated gene therapy), alphavirus mediated gene therapy, herpesvirus (e.g., cytomegalovirus) mediated gene therapy, retrovirus (e.g., lentivirus) mediated gene therapy, vaccinia virus mediated gene therapy, etc.), integrating or non-integrating nucleic acid mediated gene therapy (e.g., systemic nucleic acid gene therapy, local/regional nucleic acid gene therapy, synthetic nucleic acid gene therapy, naked DNA gene transfer therapy, liposome/micelle mediated gene therapy, cationic polymer mediated gene therapy, particle bombardment mediated gene therapy, etc.), replacement and/or corrective gene therapy (e.g., zinc-finger endonuclease mediated gene therapy, CRISPR/CAS mediated gene therapy, etc.), and the like.

As such, in instances where the host mounts an immune response to the replacement gene of a gene therapy the tolerizing vector may be configured to prevent/inhibit/repress/ameliorate the host immune response to the replacement gene expression product. In some instances, e.g., where the host mounts an immune response to a non-replacement gene component of the gene therapy the tolerizing vector may be configured to prevent/inhibit/repress/ameliorate the host immune response to the non-replacement gene component of the gene therapy, e.g., component of the gene therapy vector itself excluding the replacement gene gene product. In some instances, e.g., where the host mounts an immune response to both the replacement gene and a non-replacement gene component of the gene therapy one or more tolerizing vectors may be employed and configured to prevent/inhibit/repress/ameliorate the host immune responses to both the replacement gene and the non-replacement gene component of the gene therapy.

The terms "individual", "subject", "recipient", "host", and "patient", are used interchangeably herein and refer to any mammalian subject for whom treatment or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human. In some instances, a subject may also be a research subject, including but not limited to, e.g., a human research subject (e.g., a clinical trial participant), a preclinical research subject (e.g., a mammalian research subject, a laboratory animal, etc.), an animal model (e.g., a rodent animal model, a mouse model, a rat model, etc.).

Animal models as used herein include but are not limited to animal models of muscular dystrophy which may include but are not limited to, e.g., a mouse model of muscular dystrophy (e.g., including but not limited to, e.g., the mdx mouse model, the mdx52 mouse model, the mdx/mTR mouse model, etc.), a canine model of muscular dystrophy (e.g., including but not limited to, e.g., the canine X-linked muscular dystrophy (CXMD) model, the golden retriever muscular dystrophy (GRMD) model, the Cavalier King Charles Spaniels with Muscular Dystrophy (CKCS-MD) model, etc.), feline muscular dystrophy models (hypertrophic feline muscular dystrophy (HFMD), etc.), and those described in, e.g., Kornegay et al. (2012) Mamm Genome 23(1-2):85-108; Clollins and Morgan (2003) Int J Exp Pathol. 2003 August; 84(4): 165-172; Nakamura and Takeda (2010) J Biomed Biotechnol 2011:184393, the disclosures of which are incorporated herein by reference in their entirety. In some instances, a method of treatment and/or a tolerizing vector and/or nucleic acid, as described herein, may be evaluated, tested, or developed through the use of one or more animal models. In such instances, a treated animal model or group thereof may be compared to one or more controls, including positive controls and/or negative controls, and/or control groups.

In some instances, a nucleic acid and/or tolerizing vector, as described herein may be co-administered with one or more agents of one or more additional therapies. For example, a nucleic acid and/or tolerizing vector may be co-administered with one or more conventional immunosuppressive therapies. In some instances, two or more nucleic acids and/or tolerizing vectors, as described herein may be administered in combination, e.g., as part of a nucleic acid and/or tolerizing vector "cocktail". As a non-limiting example, such a cocktail may include a dystrophin tolerizing vector and a second tolerizing vector configured to inhibit or suppress or prevent and immune response to a component of the gene therapy other than the polypeptide encoded from replacement gene, e.g., a component of the gene therapy vector itself.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

Whether administered alone or as part of a combination therapy, any convenient and appropriate method of delivery of the nucleic acids and/or tolerizing vectors described herein may be utilized. Nucleic acid constructs can be delivered with cationic lipids (Goddard, et al, *Gene Therapy*, 4:1231-1236, 1997; Gorman, et al, *Gene Therapy* 4:983-992, 1997; Chadwick, et al, *Gene Therapy* 4:937-942, 1997; Gokhale, et al, *Gene Therapy* 4:1289-1299, 1997; Gao, and Huang, *Gene Therapy* 2:710-722, 1995, the disclosures of which are incorporated herein by reference in their entirety), by uptake of "naked DNA", and the like. In some instances, a method of delivery of the nucleic acids and/or tolerizing vectors may include or may be enhanced by electroporation, particle bombardment (i.e., biolistics), sonoporation, magnetofection, hydrodynamic delivery and the like. In some instances, a method of delivery of the nucleic acids and/or tolerizing vectors may include or may be enhanced by the use of one or more chemical methods to enhance delivery including but not limited to, e.g., the use of nucleic acid specifically modified to enhance delivery, lipoplexes, polymersomes, polyplexes, dendrimers, nanoparticles (e.g., inorganic nanoparticles), cell-penetrating peptides, cell-penetrating proteins (e.g., supercharged proteins), and the like. In some instances, the exact formulation, route of administration and dosage can be chosen empirically. Methods of nucleic acid and/or DNA vaccine delivery include but are not limited to, e.g., those described in U.S. Pat. Nos. 9,018,187, 8,877,729, 8,785,202, 8,759,499, 8,754,062, 8,747,903, 8,697,667, 8,591,862, 8,466,122, 8,338,584, 8,268,796, 8,242,089, 8,178,128, 7,922,709, 7,915,230, 7,829,657, 7,795,380, 7,795,017, 7,767,456, 7,655,467, 7,604,803, 7,534,424, 7,294,511, 7,015,040, the disclosures of which are incorporated herein by reference in their entirety.

Methods of interest for the delivery of nucleic acids and tolerizing vectors, as described herein, include but are not limited to injection delivery, oral delivery, inhalation delivery, topical delivery (e.g., transdermal delivery, transmucosal delivery, etc.), and the like. Such delivery methods may or may not make use of methods for enhancing nucleic acid delivery, e.g., as described above, where appropriate. Of interest are injection delivery methods, including but not limited to needle and needleless injection methods. As such, in many instances, nucleic acids may be delivered in a suitable diluent by intramuscular injection and, in some instances, a course of therapy may include multiple intramuscular injections, e.g., according to a pre-determined treatment schedule. In some instances, methods of intramuscular injection of nucleic acids and tolerizing vectors, as described herein, may include formulating the subject nucleic acid or tolerizing vectors in phosphate buffered saline (PBS) as a sterile solution.

Pharmaceutical Compositions

A pharmaceutical composition (e.g., a tolerizing vector composition) of the instant disclosure is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Kolliphor EL or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Methods of Assaying Therapy

In some instances, methods of evaluating tolerizing therapy effectiveness may include measuring the level of one or more makers of the replacement gene therapy vector or a polypeptide expressed therefrom. For example, in some instances, the effectiveness of the tolerizing therapy may be assessed based on the level of a polypeptide or portion thereof expressed from the replacement gene nucleic acid. In some instances, the effectiveness of the tolerizing therapy may be assessed based on the level of a nucleic acid (e.g., an mRNA) expressed from the replacement gene nucleic acid. In some instances, the effectiveness of the tolerizing therapy may be assessed based on the directly measured amount of a component of the gene therapy vector including but not limited to, e.g., the replacement gene nucleic acid, the vector itself, a protein of the delivery vehicle, etc. In some instances, a plurality of similar or different components of the replacement gene therapy vector or nucleic acids or polypeptides expressed therefrom and/or host derived components (e.g., host dystrophin mRNA, host dystrophin polypeptide, host immune factors, etc.) may be independently or simultaneously assayed (e.g., in array format) to assess the effectiveness of the tolerizing therapy.

In some instances, the effectiveness of the tolerizing therapy may be assessed based on the presence or absence or relative amount of a host-produced immune product to a component of the gene therapy. For example, in some instances, the effectiveness of the tolerizing therapy may be assessed based on the presence or absence or relative amount or level of an antibody or immunoglobulin to a component of the gene therapy including but not limited to e.g., a an antibody to a replacement gene polypeptide, an antibody to a component of the replacement gene vector itself, and the like. In some instances, a dystrophin replacement gene polypeptide antibody, e.g., for the detection and or measurement of a dystrophin gene therapy immune response, may be directly measured. For example, in some instances, the level of one or more dystrophin replacement polypeptide antibodies (i.e., anti-dystrophin, anti-microdystrophin, etc.) present in a biological sample from a subject may be measured through an assay involving binding of a detectable specific binding member to an dystrophin replacement polypeptide antibody of the sample.

In some instances, methods as described herein may include methods for assaying for the effectiveness of a tolerizing vector. Methods of evaluating tolerizing therapy effectiveness may include measuring the level of one or more specific biomarkers of the host immune response (i.e., the host immune response to the gene therapy) in a biological sample from the subject. In some instances, the level of a host immune response biomarker may include the use of one or more specific binding agents of a component of the host immune system including but not limited to, e.g., host immune cells, host immunoglobulins, host cytokines (e.g., inflammatory cytokines), expression products of the host immune system (e.g., immune system genes), etc.

In other instances, the level of an indirect biomarker, e.g., of dystrophin levels, of dystrophin antibody levels, of immune system activation, etc. may be measured or detected as a means of assessing a tolerizing vector treatment as described herein. For example, in some instances the level of one or more immune system activation markers (e.g., one or more cytokines, IL-6, IL-17a, IFN-gamma, etc.) may be measured in a biological sample from a subject as a means of determining the subject's general response to treatment with a tolerizing vector. In some instances, general immunoglobulin levels may be assessed in a sample from a subject, including but not limited to, e.g., IgG levels, IgM levels, total immunoglobulin, etc., as a means of evaluating a subject's response to tolerizing vector treatment. In some instances, the number, relative amounts, and/or activity of immune cells, e.g., collected from a biological sample from a subject, may be assessed as a means of determining a subject's response to tolerizing vector treatment. Any convenient immune system evaluation assay may find use in assessing the immune system of a subject undergoing or having had treatment with a tolerizing vector as described herein.

In some instances, a subject's response to therapy may be determined by measuring the response of one or more immune cell populations of the subject to the therapy. Immune cell populations that may be measured as a means of determining a subject's immune response may include but are not limited to, e.g., granulocytes and their progeny (e.g., basophils, eosinophils, and neutrophils), mast cells, monocytes and their progeny (e.g., macrophages, dendritic cells), natural killer cells, T cells (e.g., CD8+ T cells, CD4+ T cells (e.g., TH1 CD4+ T cells, TH2 CD4+ T cells, TH17 CD4+ T cells, and Treg CD4+ T cells), B cells, and the like. In some instances, a subject's response to treatment may be evaluated based on a subject's T cell response. In some instances, a subject's response to treatment may be evaluated based on a subject's B cell response. Methods of measuring a subject's immune system activity including response to therapy or autoimmune response include but are not limited to, e.g., T-cell proliferation assay, immunoblot assay, autoantibody detection (e.g., dystrophin autoantibody detection), flow cytometric methods, etc. and those methods described in Seyfert-Margolis et al., *Diabetes.* 2006 55(9): 2588-2594; Bercovici et al., *Clin Vaccine Immunol.* 2000 7(6): 859-864; Gratama et al. *Cytometry A.* 2008 73(11): 971-974; the disclosures of which are incorporated herein by reference in their entirety. The ordinary artisan will readily recognize where a particular immune assay, e.g., an assay for a particular autoimmune disease, may be adapted for use in the methods as described herein, e.g., adaptation of an existing immune response assay for evaluation of a treatment response as described herein.

In some instances, assessments of a subject's immune system and/or immune response to a particular component of a gene therapy treatment may be performed prior to tolerizing vector administration, e.g., to establish a baseline. In some instances, assessments of a subject's immune system and/or immune response to a particular component of a gene therapy treatment may be performed during therapy, e.g., at a pre-determined time point after the first administration and before the final administration (e.g., as according to a particular schedule including but not limited to one or more measurements performed within the first month of treatment, within the second month of treatment, within the third month of treatment, within the fourth month of treatment, within the fifth month of treatment, within the sixth month of treatment, within the seventh month of treatment, within the eight month of treatment, within the ninth month of treatment, within the tenth month of treatment, within the eleventh month of treatment, within the first year of treatment, etc.), to assess a subject's response to tolerizing vector therapy. In some instances, assessments of a subject's immune system and/or immune response to a particular component of a gene therapy treatment may be performed after therapy, e.g., at a pre-determined time point after administration of the final dose (e.g., as according to a particular schedule including but not limited to one or more measurements performed after the first month of treatment, after the second month of treatment, after the third month of treatment, after the fourth month of treatment, after the fifth month of treatment, after the sixth month of treatment, after the seventh month of treatment, after the eight month of treatment, after the ninth month of treatment, after the tenth month of treatment, after the eleventh month of treatment, after the first year of treatment, etc.), to assess a subject's response to the course of tolerizing vector treatment. In some instances, the results of such assessments may inform the therapeutic regimen and therapy may be adjusted, e.g., extended or terminated or modified (e.g., dose modification), based on the results of one or more of the assessments described herein.

In some instances, one or more functional assays may be performed as a means of assaying the effectiveness of the gene therapy and indirectly assaying the effectiveness of the tolerizing therapy. For example, in some instances, one or more functional measurements of disease recovery or disease progression may be measured in accordance with the described methods and/or as part of a therapy regimen. As non-limiting examples, functional tests that may be used to assay muscular dystrophy progression and/or recovery include muscle function tests including but not limited to force measurements of shoulder flexion, shoulder extension, shoulder abduction, shoulder lateral rotation, shoulder medial rotation, elbow flexion, elbow extension, wrist extension, hip flexion, hip abduction, knee flexion, knee extension, ankle dorsiflexion, and the like. In some instances, muscle force tests may be compared to control or normative values, e.g., as described in Andrews et al., *Phys Ther* (1996) 76(3):248-59; Brussock et al. *Phys Ther* (1992) 72(2):105-14 and Lerario et al. *BMC Neurol* (2012) 12:91, the disclosures of which are incorporated herein by reference in their entirety. In some instances, muscular dystrophy progression and/or recovery assays may be performed using techniques involving electrical stimulation and/or electrical monitoring, including e.g., those methods routinely performed in the research setting, including e.g., muscle twitch force measurements as described in Sacco et al. *Cell* (2010) 143:1059-1071, the disclosure of which is incorporated herein by reference in its entirety, and those performed in the clinical setting, including e.g., electromyography or nerve conduction tests as described in Paganoni & Amato, *Phys Med Rehabil Clin N Am* (2013) 24(1):193-207, the disclosure of which is incorporated herein by reference in its entirety. Any convenient test routinely used for monitoring or diagnosing muscular dystrophies, including but not limited to blood enzyme tests, muscle biopsy, etc., may find use in evaluating treatments described herein.

Kits

Also provided are kits for use in the subject methods. The subject kits include any combination of components and compositions for performing the subject methods. In some embodiments, a kit can include the following: a tolerizing vector, a vector delivery device, a suitable buffer and any combination thereof.

In some embodiments, a subject kit includes lyophilized tolerizing vector and a suitable diluent for resuspending the lyophilized tolerizing vector before use where the tolerizing vector and the diluent are present in separate containers. In some instances, a subject kit may include one or more pre-formulated doses of tolerizing vector in "ready-to-use" format (e.g., as injectable gene tolerizing vaccine). In instances where a dosing regimen is desired that includes multiple administrations of one or more tolerizing vectors, a subject kit may include two or more doses of tolerizing vector, in a pre-formulated or an unformulated configuration, and may, optionally, include instructions (e.g., instructions as to when each dose should be administered, instruction for preparing unformulated doses, instructions for dose delivery, etc.). In some instances, a subject kit may include one or more testing reagents or testing devices or combinations thereof for assaying a subject's need for therapy (e.g., before or after therapy), assaying the effectiveness of therapy (e.g., during or after therapy), etc. Such devices may include but are not limited to, e.g., an array of a plurality of specific binding members to assess the effectiveness of tolerizing vector treatment.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (ph; seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1

Construction of Tolerizing Vector

Plasmid DNA vector encoding human microdystrophin was engineered by inserting the 3630 bp microdystrophin, hinge 3 microdystrophin (deltaH2-R23+H3/deltaCT) cDNA into the 3052 bp pBHT1CI plasmid backbone driven by the CMV promoter, to generate a tolerizing plasmid DNA vector encoding human microdystrophin, pBHT1CI-H3UDYS. The backbone of pBHT1CI has been modified to decrease the number of immunostimulatory CpG motifs and substituted with immunosuppressive GpG motifs.

Tolerizing Treatment

Six-week old male mdx/mTR (mdx represents a point mutation in Dystrophin gene resulting in near-complete absence of dystrophin protein and mTR represents a mutation resulting in a lack of telomerase activity resulting in reduced regenerative capacity in myogenic stem cells) mice were administered a bolus of $3 \times 10^{12}$ AAV6-CMV-H3UDYS vector genome intravenously for systemic gene delivery of human microdystrophin. For these experiments, empty vector, pBHT1CI, and vector-less vehicle (PBS) were used as controls. Five days after administration of AAV6-CMV-H3UDYS both quadriceps of the mice were injected intramuscularly (i.m.) with 0.25% bupivicaine-HCL. Two days following bupivicaine injection the mice were randomly divided into three groups of five mice each and injected i.m. into both quadriceps with either vehicle (1×PBS), pBHT1CI or pBHT1CIH3UDYS. In summary, the mice received thirty-two weekly i.m. injections of vehicle, pBHT1CI or pBTH1CI-H3UDYS. Sera was collected for peptide microarray analysis of antibodies to dystrophin and AAV6 peptides at weeks 0, 5, 16 and 32. A schematic of the dosing schedule and sera collection is provided in FIG. 1.

Expression Analysis

Autoantibody responses in serum derived from mdx/mTR and C57BL/6 wild-type mice was analyzed on a 1,404-feature dystrophin proteome arrays contain 306 distinct antigens consisting of overlapping peptides representing human dystrophin, AAV6 capsid, and control peptides and proteins.

Arrays incubated with this serum revealed that mice developed autoantibody reactivity against epitopes derived from human dystrophin. The significance analysis of microarrays (SAM) algorithm was applied to identify antigen features with statistically significant differences in array reactivity between the treated groups. A hierarchical cluster algorithm using a pairwise similarity function was then used to order SAM-selected antigen features on the basis of the degree of similarity in their autoantibody reactivity profiles.

Figure 2:
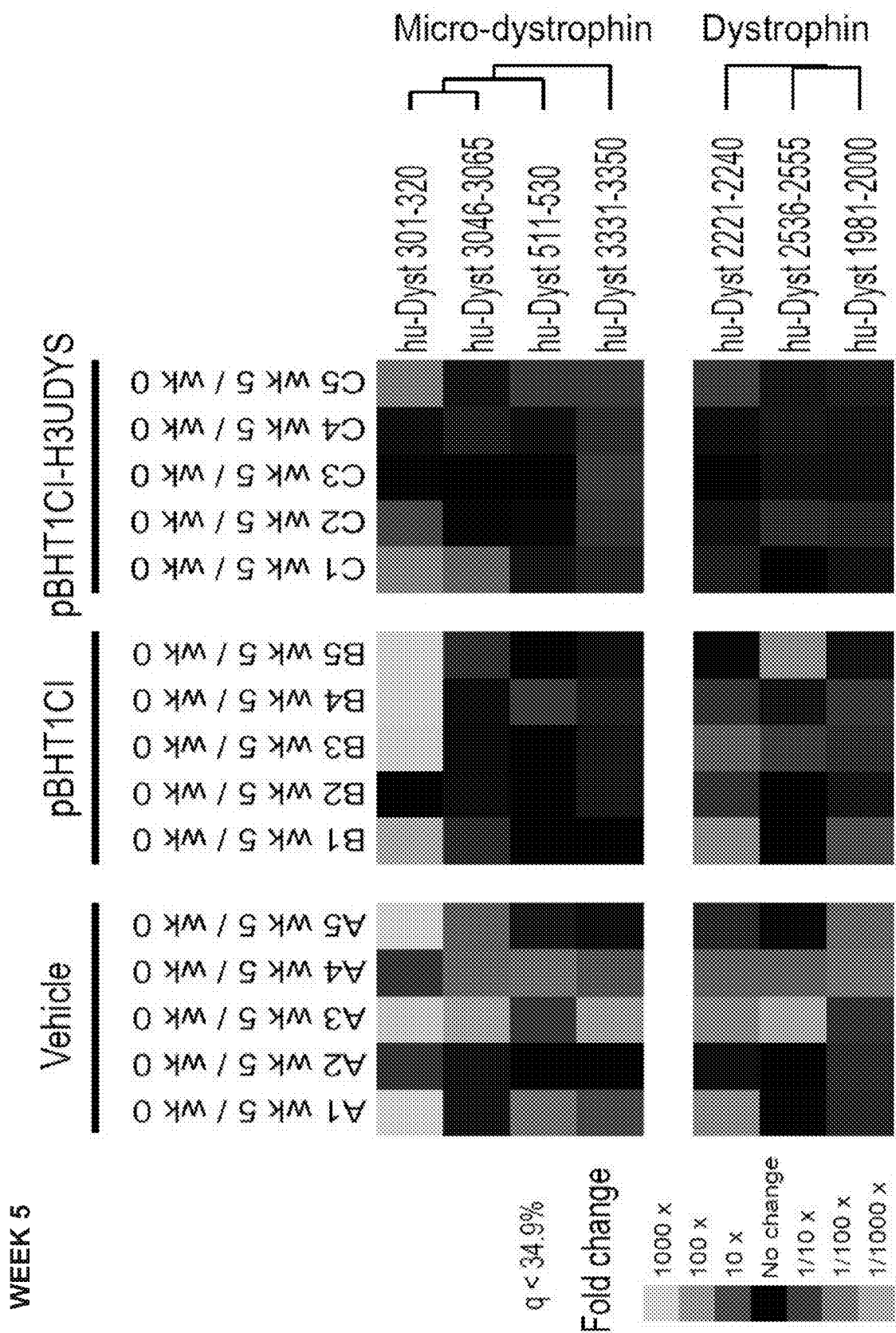
FIG. 2 depicts mdx/mTR mouse antibody responses to micro-dystrophin and dystrophin polypeptides at week five in vehicle, empty vector control (pBHT1CI), and tolerizing vector (pBHT1CI-H3UDYS) treatment groups.
Figure 3:
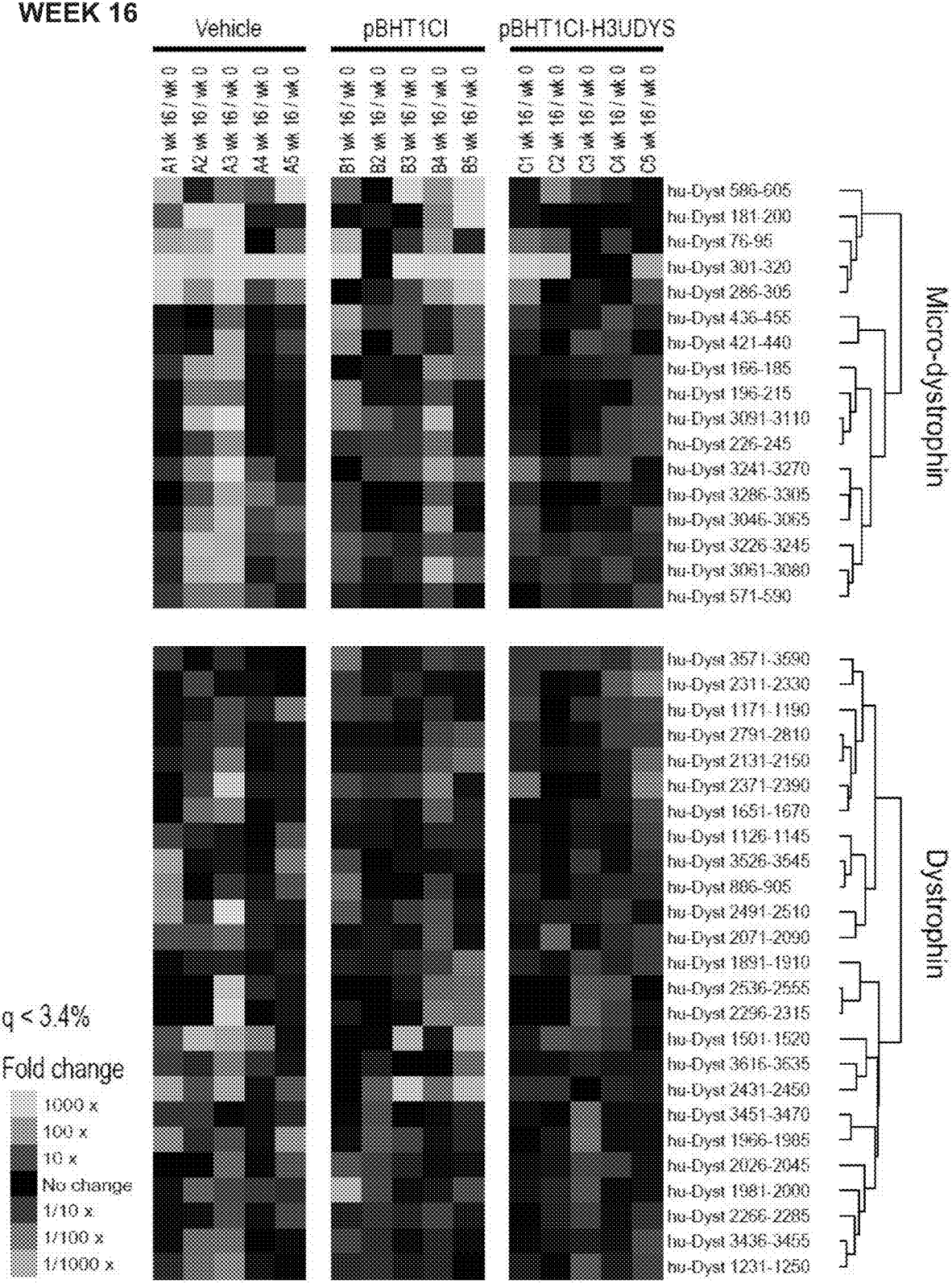
FIG. 3 depicts mdx/mTR mouse antibody responses to micro-dystrophin and dystrophin polypeptides at week 16 in vehicle, empty vector control (pBHT1CI), and tolerizing vector (pBHT1CI-H3UDYS) treatment groups.
Figure 4:
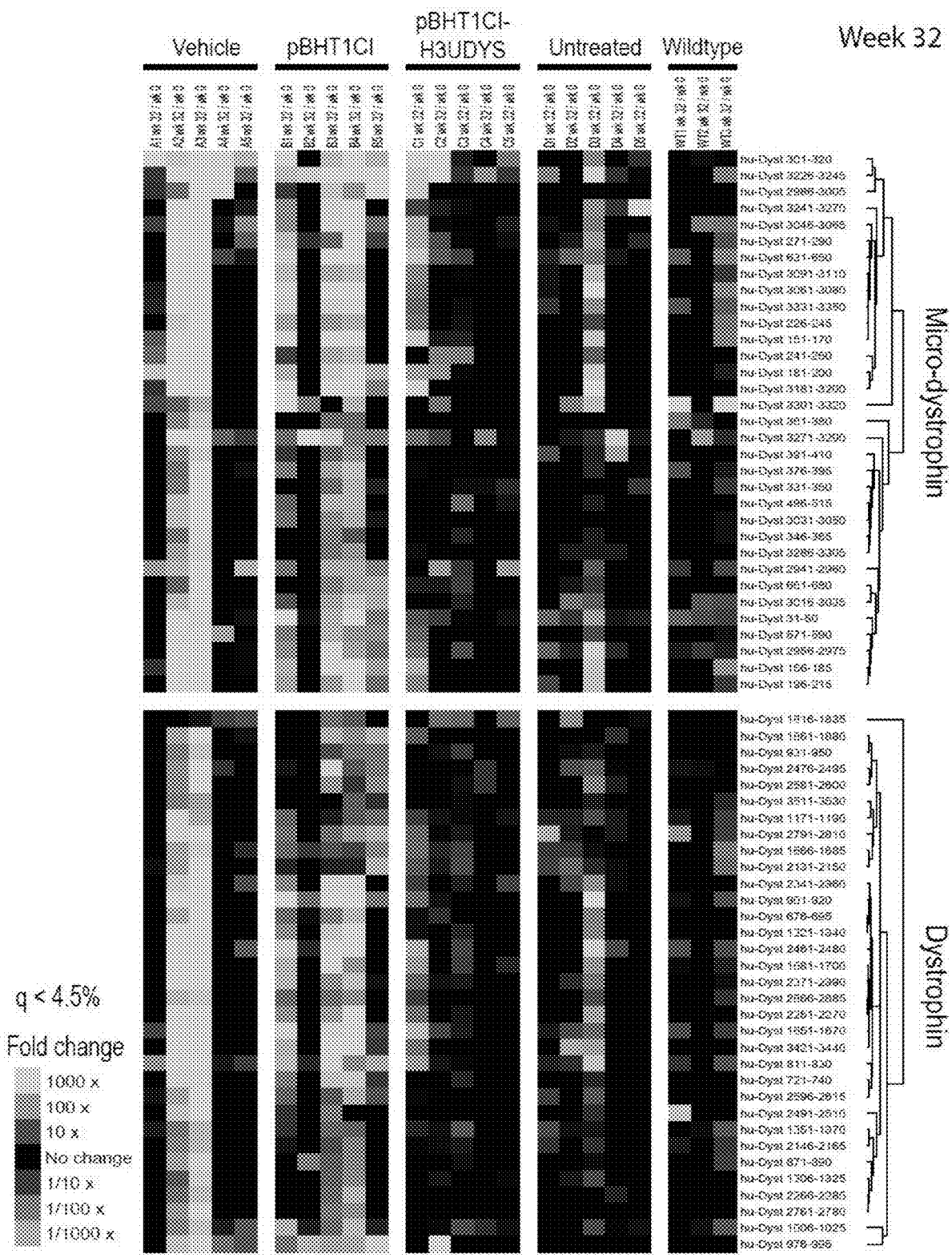
FIG. 4 depicts mdx/mTR mouse antibody responses to micro-dystrophin and dystrophin polypeptides at week 32 in vehicle, empty vector control (pBHT1CI), and tolerizing vector (pBHT1CI-H3UDYS) treatment groups.
Figure 5:
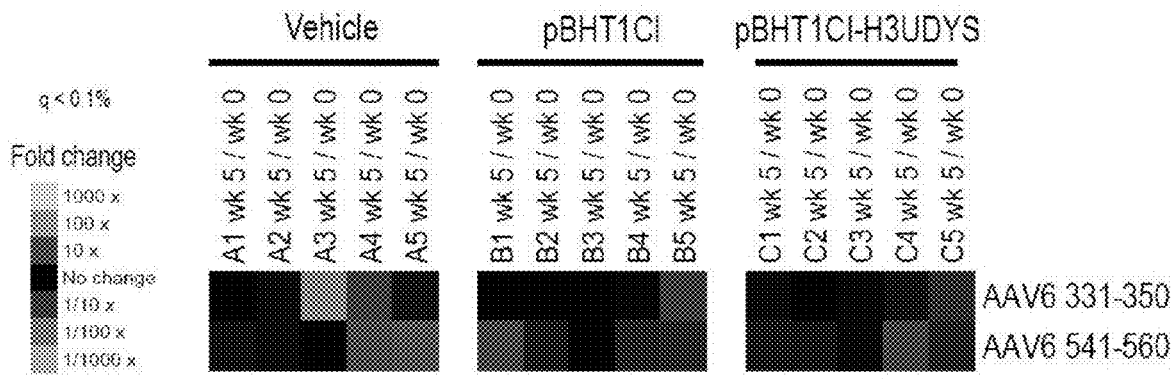
FIG. 5 depicts mdx/mTR mouse antibody responses to AAV6 capsid polypeptides at week five in vehicle, empty vector control (pBHT1CI), and tolerizing vector (pBHT1CI-H3UDYS) treatment groups.
Figure 6:
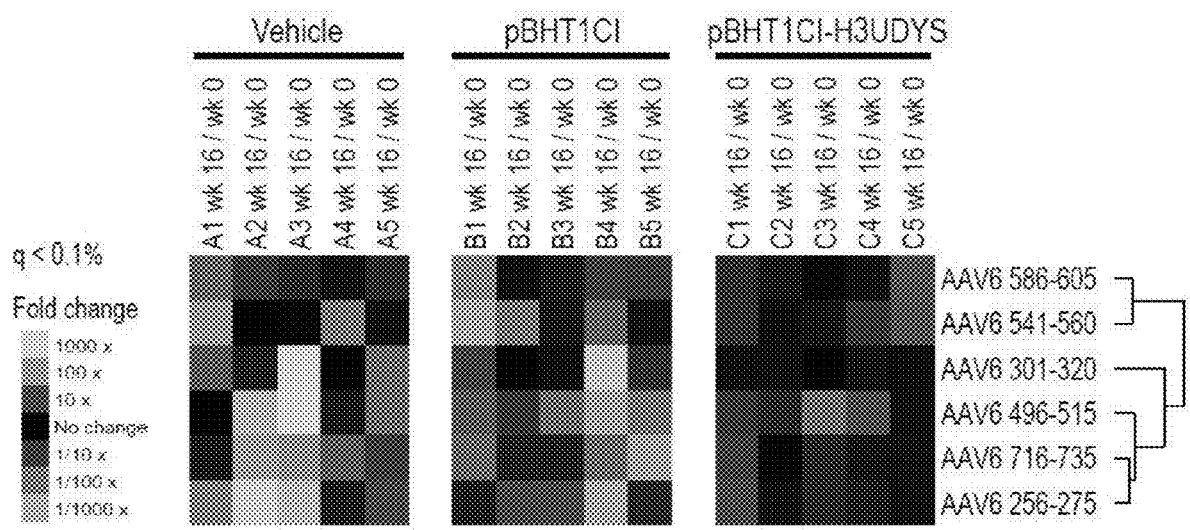
FIG. 6 depicts mdx/mTR mouse antibody responses to AAV6 capsid polypeptides at week 16 in vehicle, empty vector control (pBHT1CI), and tolerizing vector (pBHT1CI-H3UDYS) treatment groups.
Figure 7:
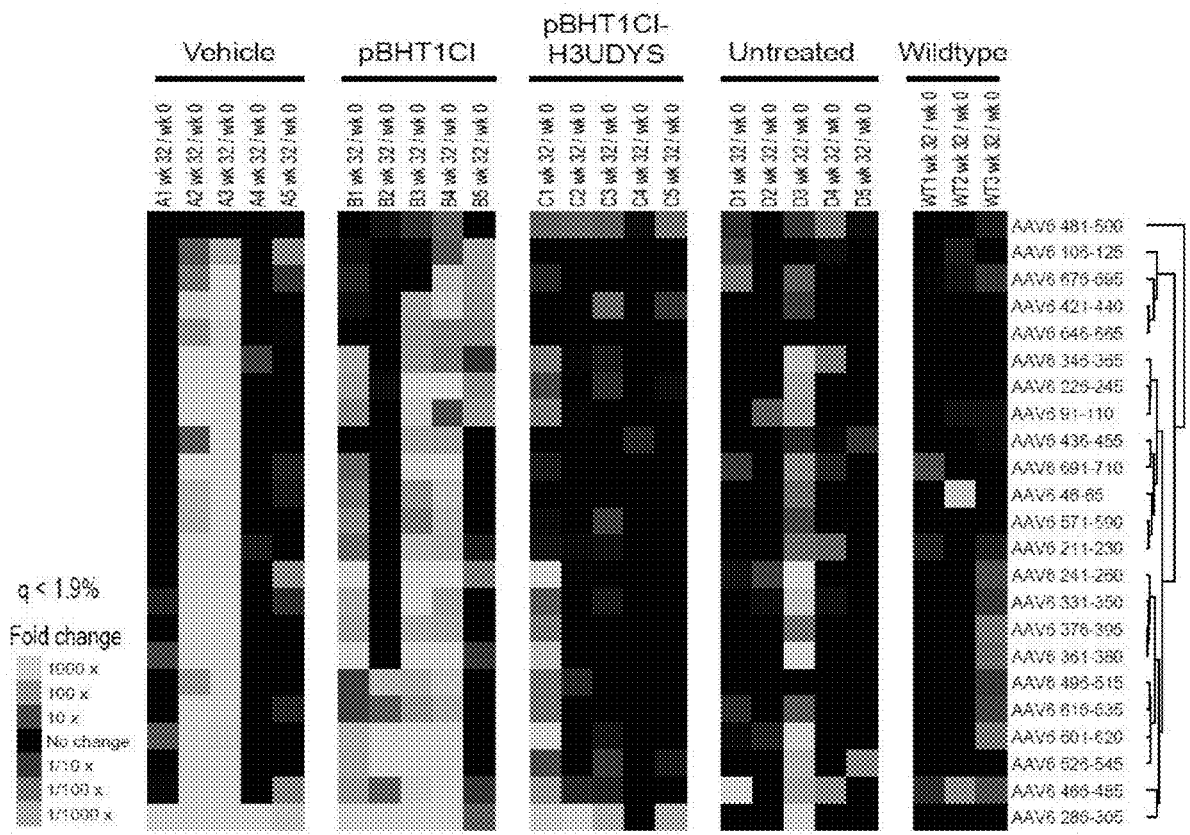
FIG. 7 depicts mdx/mTR mouse antibody responses to AAV6 capsid polypeptides at week 36 in vehicle, empty vector control (pBHT1CI), and tolerizing vector (pBHT1CI-H3UDYS) treatment groups.
Figure 8:
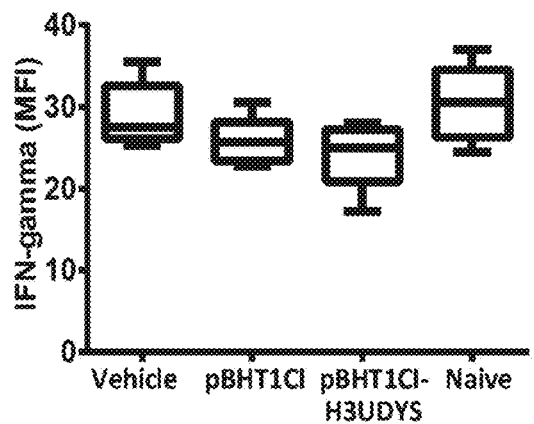
FIG. 8 depicts IFN-γ serum levels measured in mice receiving vector-less vehicle, empty vector or microdystrophin tolerizing vector following gene therapy and untreated mice at 5 weeks.
Figure 11:
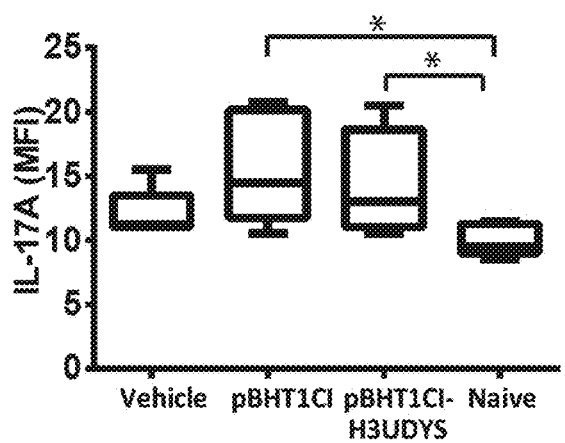
FIG. 11 depicts IL-17A serum levels measured in mice receiving vector-less vehicle, empty vector or microdystrophin tolerizing vector following gene therapy and untreated mice at 5 weeks.
Figure 9:
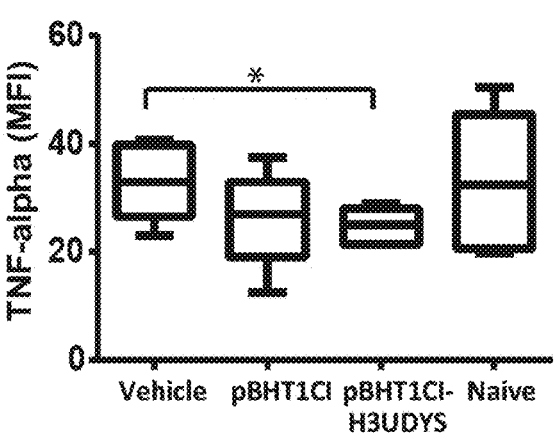
FIG. 9 depicts TNF-α serum levels measured in mice receiving vector-less vehicle, empty vector or microdystrophin tolerizing vector following gene therapy and untreated mice at 5 weeks.
Figure 12:
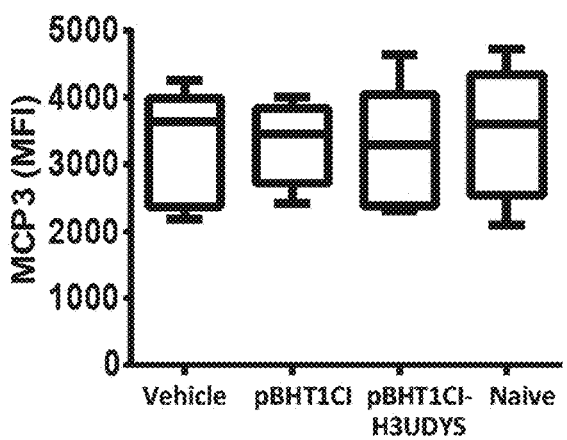
FIG. 12 depicts MCP3 serum levels measured in mice receiving vector-less vehicle, empty vector or microdystrophin tolerizing vector following gene therapy and untreated mice at 5 weeks.
Figure 10:
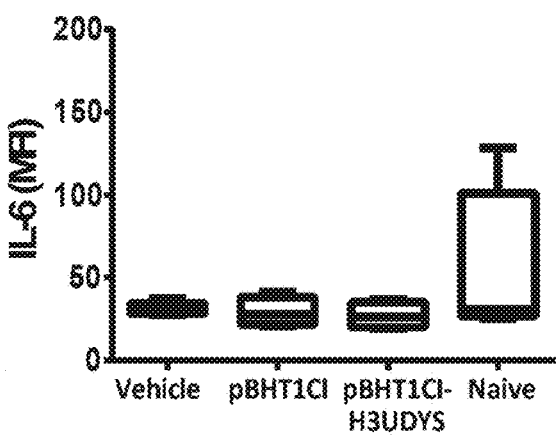
FIG. 10 depicts IL-6 serum levels measured in mice receiving vector-less vehicle, empty vector or microdystrophin tolerizing vector following gene therapy and untreated mice at 5 weeks.
Figure 13:
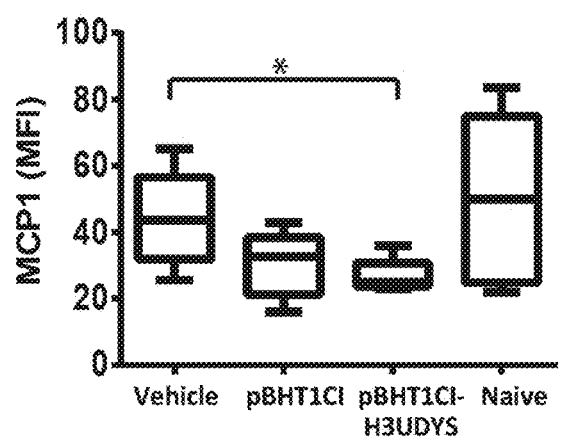
FIG. 13 depicts MCP1 serum levels measured in mice receiving vector-less vehicle, empty vector or microdystrophin tolerizing vector following gene therapy and untreated mice at 5 weeks.
Figure 14:
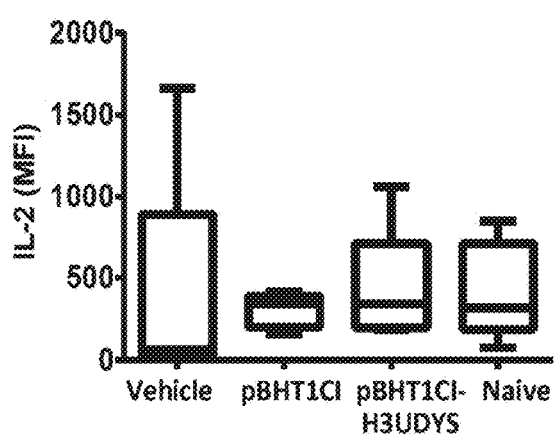
FIG. 14 depicts IL-2 serum levels measured in mice receiving vector-less vehicle, empty vector or microdystrophin tolerizing vector following gene therapy and untreated mice at 5 weeks.
Figure 17:
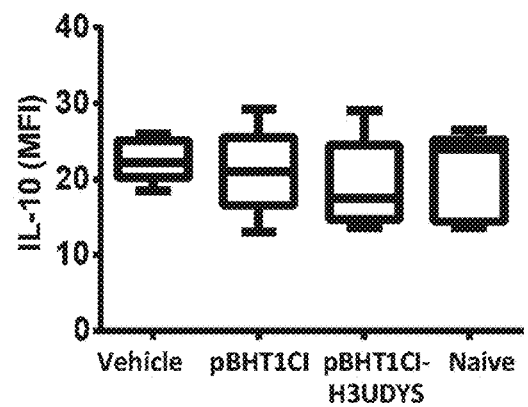
FIG. 17 depicts IL-10 serum levels measured in mice receiving vector-less vehicle, empty vector or microdystrophin tolerizing vector following gene therapy and untreated mice at 5 weeks.
Figure 15:
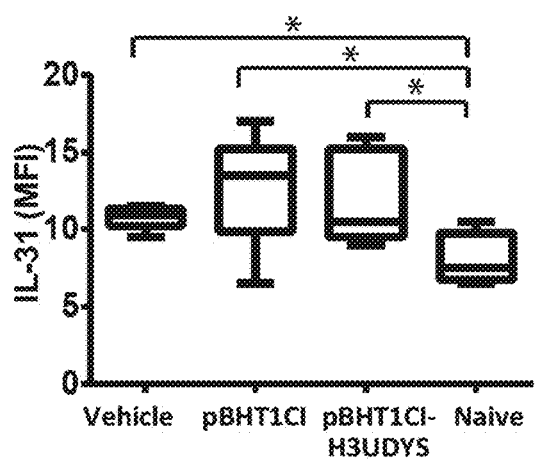
FIG. 15 depicts IL-31 serum levels measured in mice receiving vector-less vehicle, empty vector or microdystrophin tolerizing vector following gene therapy and untreated mice at 5 weeks.
Figure 18:
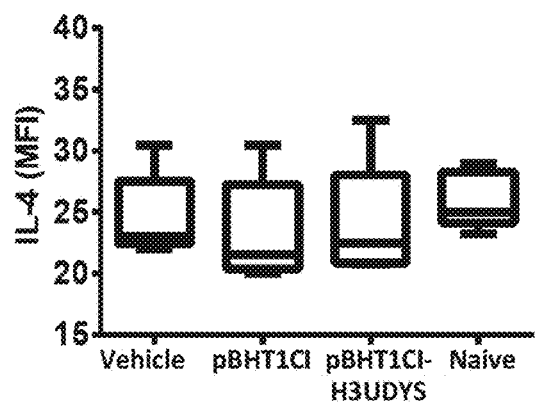
FIG. 18 depicts IL-4 serum levels measured in mice receiving vector-less vehicle, empty vector or microdystrophin tolerizing vector following gene therapy and untreated mice at 5 weeks.
Figure 16:
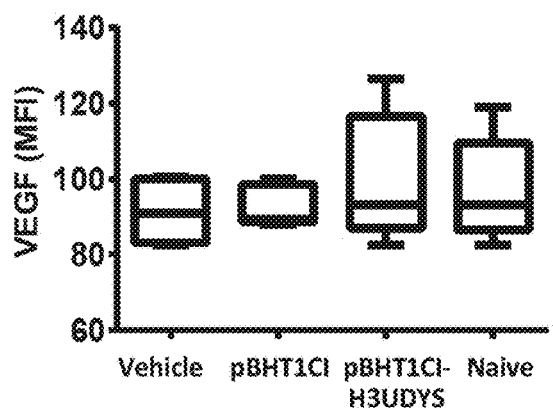
FIG. 16 depicts VEGF serum levels measured in mice receiving vector-less vehicle, empty vector or microdystrophin tolerizing vector following gene therapy and untreated mice at 5 weeks.
Figure 19:
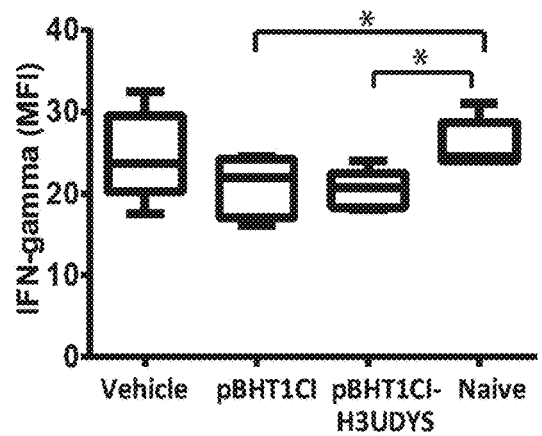
FIG. 19 depicts IFN-γ serum levels measured in mice receiving vector-less vehicle, empty vector or microdystrophin tolerizing vector following gene therapy and untreated mice at 32 weeks.
Figure 20:
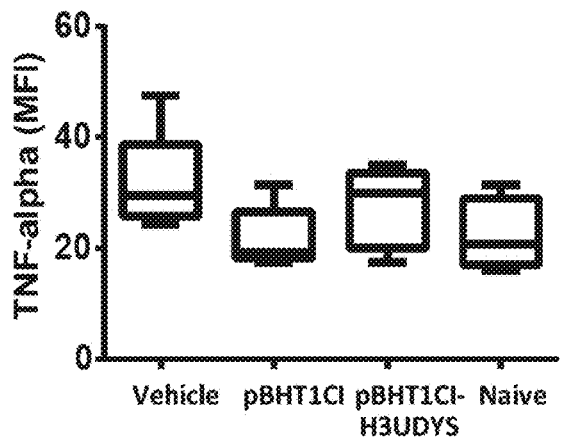
FIG. 20 depicts TNF-α serum levels measured in mice receiving vector-less vehicle, empty vector or microdystrophin tolerizing vector following gene therapy and untreated mice at 32 weeks.
Figure 23:
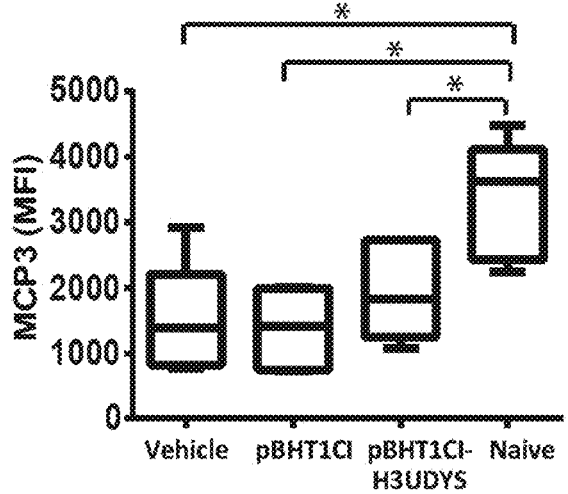
FIG. 23 depicts MCP3 serum levels measured in mice receiving vector-less vehicle, empty vector or microdystrophin tolerizing vector following gene therapy and untreated mice at 32 weeks.
Figure 21:
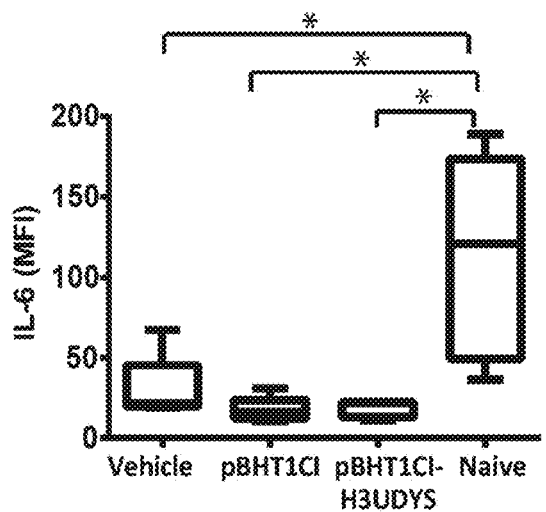
FIG. 21 depicts IL-6 serum levels measured in mice receiving vector-less vehicle, empty vector or microdystrophin tolerizing vector following gene therapy and untreated mice at 32 weeks.
Figure 24:
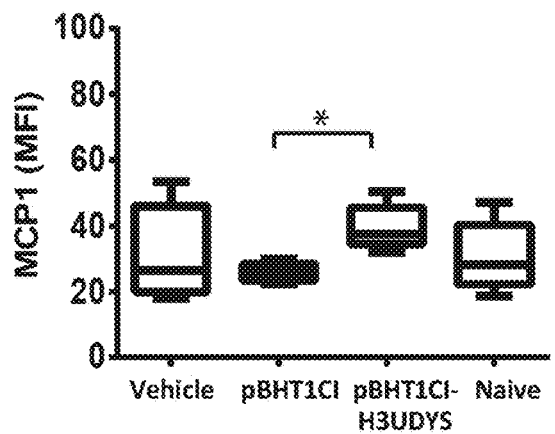
FIG. 24 depicts MCP1 serum levels measured in mice receiving vector-less vehicle, empty vector or microdystrophin tolerizing vector following gene therapy and untreated mice at 32 weeks.
Figure 22:
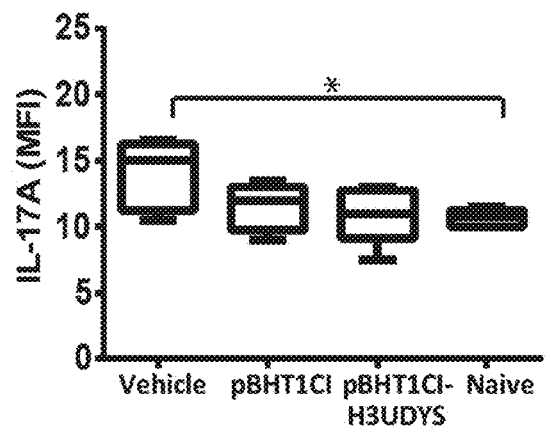
FIG. 22 depicts IL-17A serum levels measured in mice receiving vector-less vehicle, empty vector or microdystrophin tolerizing vector following gene therapy and untreated mice at 32 weeks.
Figure 25:
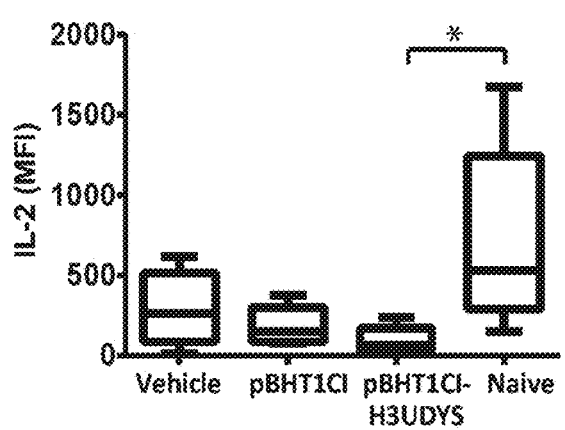
FIG. 25 depicts IL-2 serum levels measured in mice receiving vector-less vehicle, empty vector or microdystrophin tolerizing vector following gene therapy and untreated mice at 32 weeks.
Figure 26:
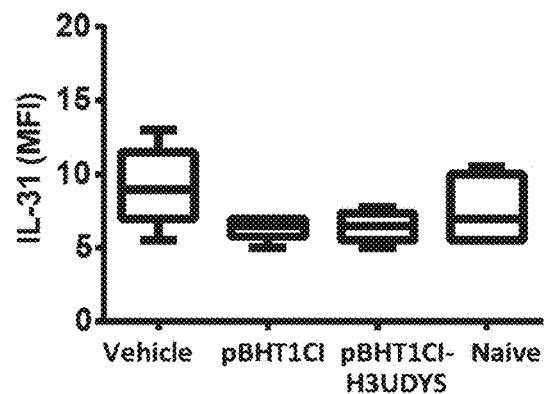
FIG. 26 depicts IL-31 serum levels measured in mice receiving vector-less vehicle, empty vector or microdystrophin tolerizing vector following gene therapy and untreated mice at 32 weeks.
Figure 28:
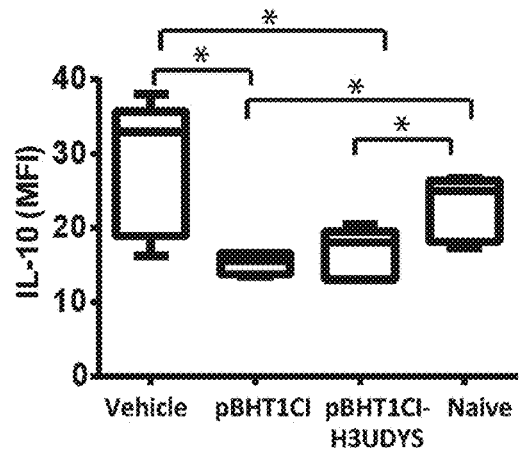
FIG. 28 depicts IL-10 serum levels measured in mice receiving vector-less vehicle, empty vector or microdystrophin tolerizing vector following gene therapy and untreated mice at 32 weeks.
Figure 27:
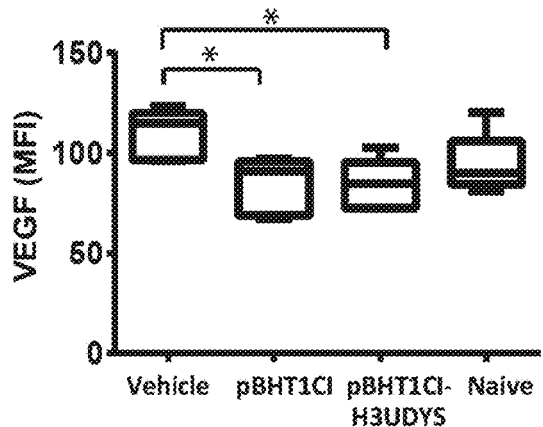
FIG. 27 depicts VEGF serum levels measured in mice receiving vector-less vehicle, empty vector or microdystrophin tolerizing vector following gene therapy and untreated mice at 32 weeks.
Figure 29:
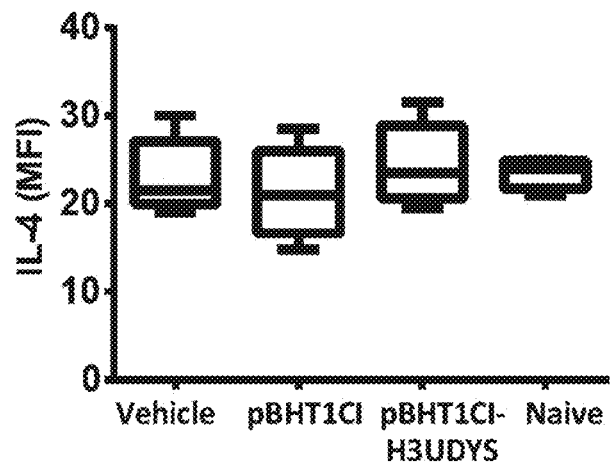
FIG. 29 depicts IL-4 serum levels measured in mice receiving vector-less vehicle, empty vector or microdystrophin tolerizing vector following gene therapy and untreated mice at 32 weeks.

Antibody reactivity to dystrophin peptides was detected as early as week 5 and a reduction was seen after 5 treatments with microdystrophin tolerizing DNA vaccine (FIG. 2). By week 16 (16 treatments) (FIG. 3) and week 32 (32 treatments) (FIG. 4) there was statistical significance between the untreated group following microdystrophin gene replacement therapy (group A), and the microdystrophin tolerizing DNA vaccine treated group (group C), in which group C had lower antibody responses to dystrophin than group A. The results of the statistical testing were as follows: Week 5: A vs C (q-value=34.9%), A vs B (71.0%), B vs C (40.5%); Week 16: A vs C (q-value=3.4%), A vs B (32.5%), B vs C (77.6%) Week 32: A vs C (q-value=4.5%), A vs B (55.8%), B vs C (11.5%). Antibody response to AAV6 capsid was also detected after microdystrophin gene therapy and such responses were also reduced after treatment with microdystrophin tolerizing DNA vaccine at week 5 (FIG. 5), week 16 (FIG. 6) and week 32 (FIG. 7).

Immune Response Testing

The serum collected from the gene therapy treated mice receiving vector-less vehicle (Vehicle), empty vector (pBHT1CI) and tolerizing vector (PBHT1CI-H3UDYS) and untreated mice was further analyzed for immune system activity by measuring serum cytokine levels via a 38-plex Luminex Assay at week 5 (FIGS. 8-18) and week 32 (FIGS. 19-29) after treatment. The serum of mice receiving the tolerizing vector showed a decrease in a number of the tested immune system activity markers including e.g., interferon gamma (IFN-γ), interleukin 6 (IL-6) and interleukin 2 (IL-2) demonstrating a reduction in immune response following tolerizing therapy.

Physiological Testing

Histological and functional physiological testing was performed at thirty-eight weeks of age. Standard protocols were used for histological staining muscle force tests.

Figure 30:
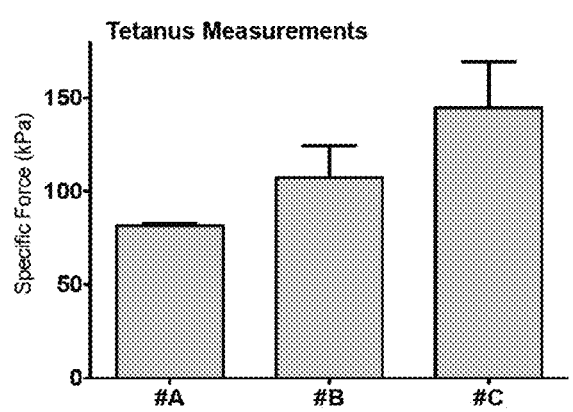
FIG. 30 depicts tetanus measurements in the three treatment/control groups (A=vehicle control, B=pBHT1CI and C=pBHT1CI-H3UDYS).
Figure 31:
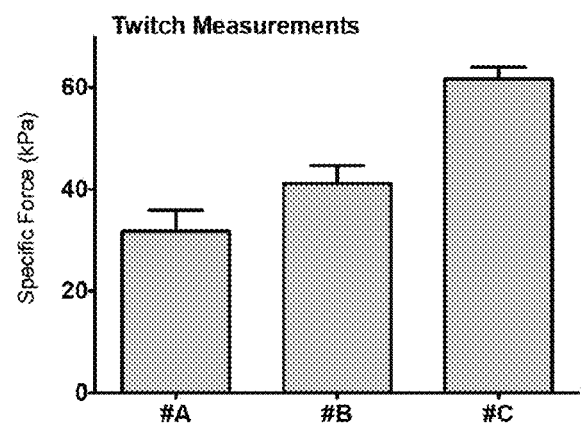
FIG. 31 depicts twitch measurements in the three treatment/control groups (A=vehicle control, B=pBHT1CI and C=pBHT1CI-H3UDYS).
Figure 32:
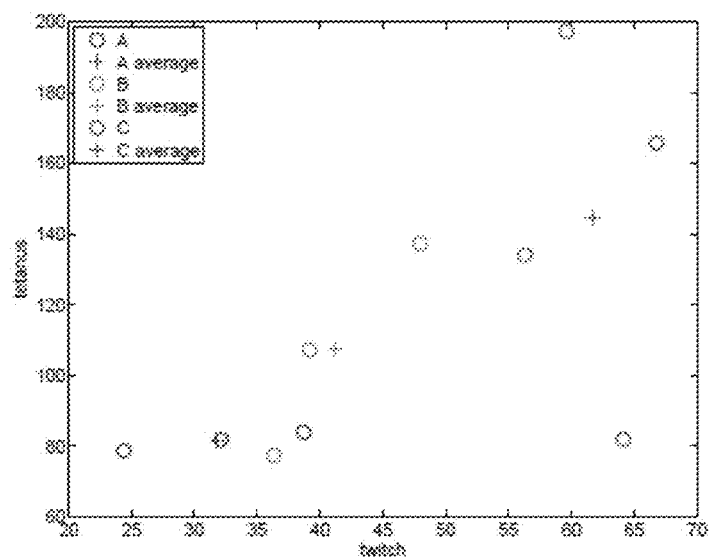
FIG. 32 depicts the correlation between twitch and tetanus force measurements from the three treatment/control groups (A=vehicle control, B=pBHT1CI and C=pBHT1CI-H3UDYS).

For muscle force tests the male mdx/mTR mice were anesthetized and force measurements of the gastrocnemius muscle were performed in situ. Significant differences were observed between the treatment and control groups (#A=vehicle control, #B=pBHT1CI and #C=pBHT1CI-H3UDYS) in twitch force and specific tetanus force with the pBHT1CI-H3UDYS treatment group performing best (FIG. 30 and FIG. 31). Correlation analysis between twitch force and specific tetanus force further elucidated the functional improvement in the pBHT1CI-H3UDYS treatment group (FIG. 32).

Figure 33:
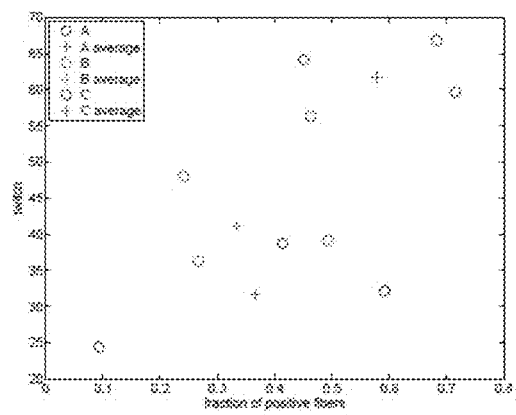
FIG. 33 depicts the correlation between the number of microdystrophin positive fibers and twitch force measurements in samples from the three treatment/control groups (A=vehicle control, B=pBHT1CI and C=pBHT1CI-H3UDYS).
Figure 34:
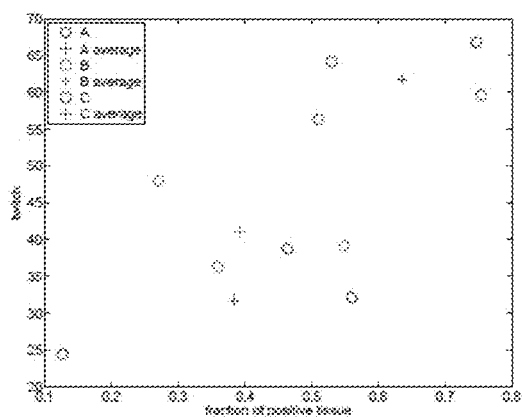
FIG. 34 depicts the correlation between the amount of microdystrophin positive tissue and twitch force measurements in samples from the three treatment/control groups (A=vehicle control, B=pBHT1CI and C=pBHT1CI-H3UDYS).
Figure 35:
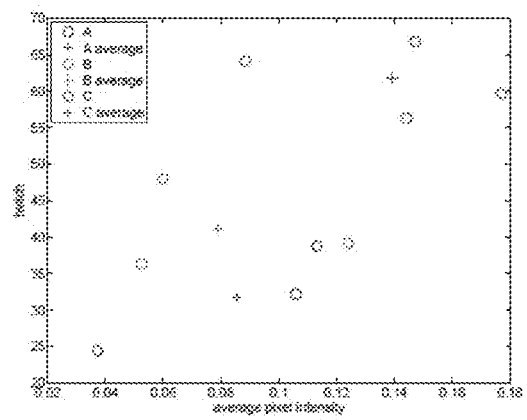
FIG. 35 depicts the correlation between the sample pixel intensity in microdystrophin stained samples and twitch force measurements from the three treatment/control groups (A=vehicle control, B=pBHT1CI and C=pBHT1CI-H3UDYS).
Figure 36:
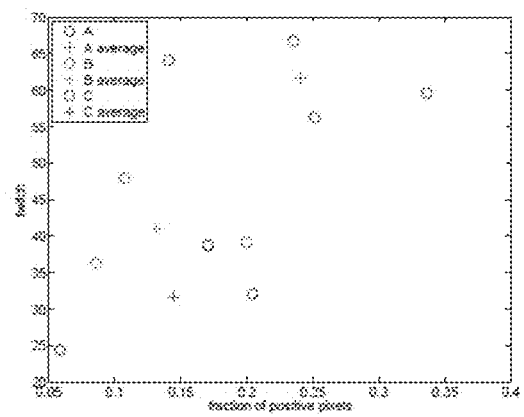
FIG. 36 depicts the correlation between the average number of microdystrophin positive pixels and twitch force measurements in samples from the three treatment/control groups (A=vehicle control, B=pBHT1CI and C=pBHT1CI-H3UDYS).
Figure 37:
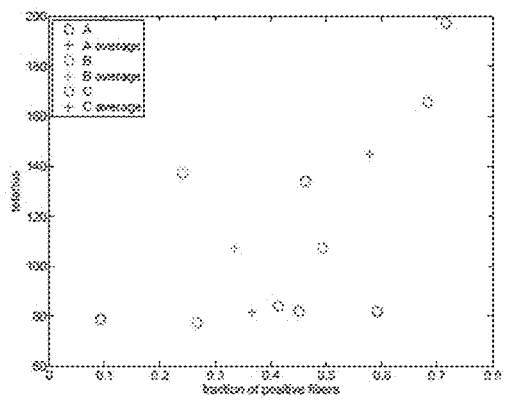
FIG. 37 depicts the correlation between the number of microdystrophin positive fibers and tetanus force measurements in samples from the three treatment/control groups (A=vehicle control, B=pBHT1CI and C=pBHT1CI-H3UDYS).
Figure 38:
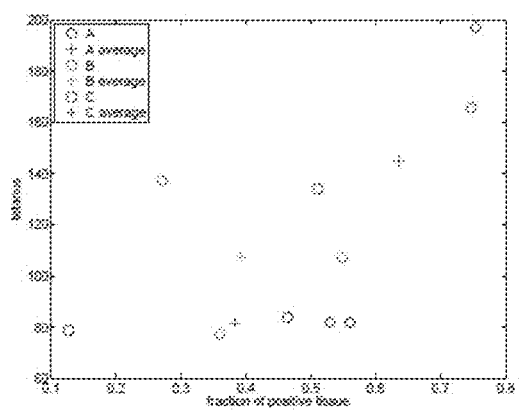
FIG. 38 depicts the correlation between the amount of microdystrophin positive tissue and tetanus force measurements in samples from the three treatment/control groups (A=vehicle control, B=pBHT1CI and C=pBHT1CI-H3UDYS).
Figure 39:
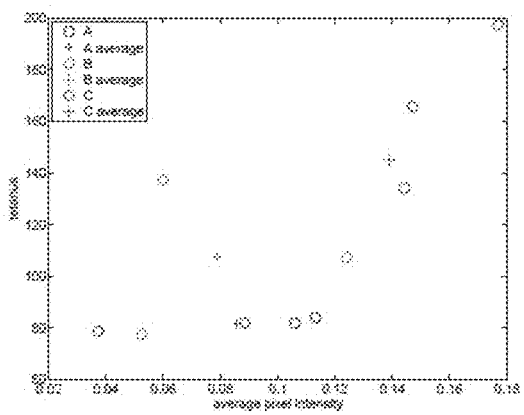
FIG. 39 depicts the correlation between the sample pixel intensity in microdystrophin stained samples and tetanus force measurements from the three treatment/control groups (A=vehicle control, B=pBHT1CI and C=pBHT1CI-H3UDYS).
Figure 40:
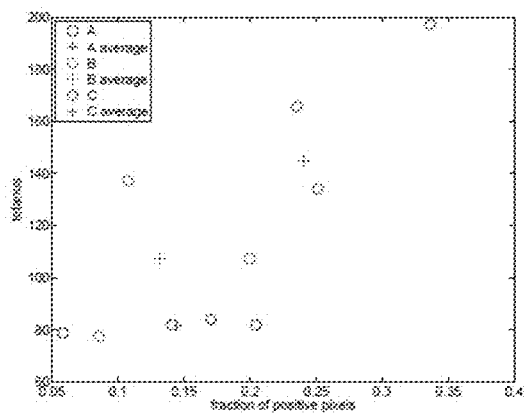
FIG. 40 depicts the correlation between the average number of microdystrophin positive pixels and tetanus force measurements in samples from the three treatment/control groups (A=vehicle control, B=pBHT1CI and C=pBHT1CI-H3UDYS).

Histological preparations of gastrocnemius muscle collected from the three treatment and control groups (#A=vehicle control, #B=pBHT1CI and #C=pBHT1CI-H3UDYS) were stained for microdystrophin. Correlation analysis between microdystrophin positively stained fibers and twitch (FIG. 33), between microdystrophin positively stained tissue and twitch (FIG. 34), between pixel intensity and twitch (FIG. 35) between positive pixels and twitch (FIG. 36), between positive fibers and tetanus (FIG. 37), between positive tissue and tetanus (FIG. 38), between pixel intensity and tetanus (FIG. 39), between positive pixels and tetanus (FIG. 40) were performed and demonstrated a correlation between higher functional measures and microdystrophin staining in the pBHT1CI-H3UDYS group. Such correlations demonstrate that the functional improvement measured in the pBHT1CI-H3UDYS group was due to the tolerizing treatment.

Figure 41:
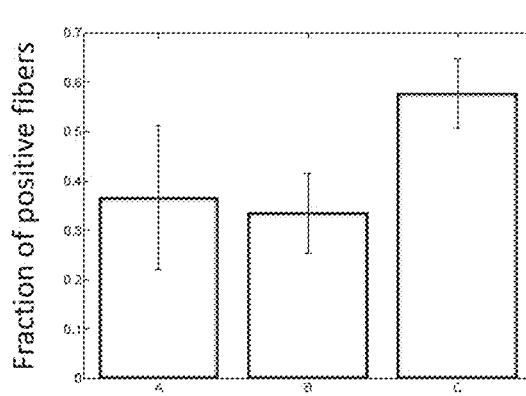
FIG. 41 depicts the average number of microdystrophin positive fibers in histologically stained muscle samples from the three treatment/control groups (A=vehicle control, B=pBHT1CI and C=pBHT1CI-H3UDYS).
Figure 42:
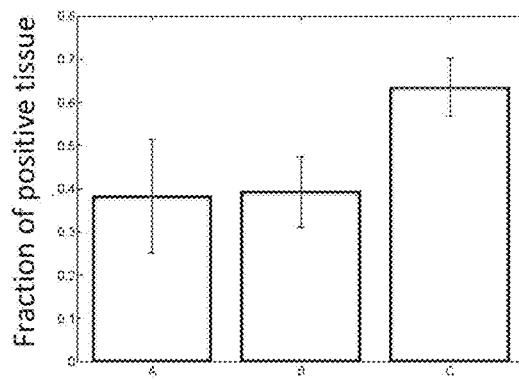
FIG. 42 depicts the average amount of positive microdystrophin stained tissue in histologically stained muscle samples from the three treatment/control groups (A=vehicle control, B=pBHT1CI and C=pBHT1CI-H3UDYS).
Figure 43:
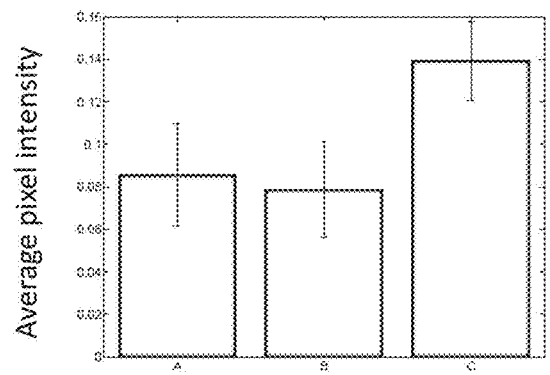
FIG. 43 depicts the average pixel intensity of microdystrophin stained muscle samples from the three treatment/control groups (A=vehicle control, B=pBHT1CI and C=pBHT1CI-H3UDYS).
Figure 44:
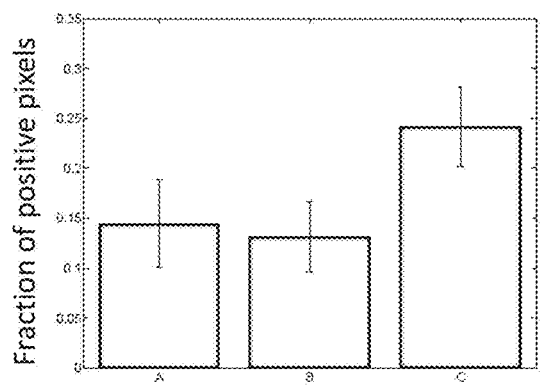
FIG. 44 depicts the average number of microdystrophin positive pixel in histologically stained muscle samples from the three treatment/control groups (A=vehicle control, B=pBHT1CI and C=pBHT1CI-H3UDYS).

The numbers of microdystrophin positively stained fibers (FIG. 41) and tissues (FIG. 42) as well as the pixel intensity (FIG. 43) and pixel numbers (FIG. 44) in images obtained from microdystrophin stained histological samples were all highest in the pBHT1CI-H3UDYS group as compared to the vehicle control and pBHT1CI groups. This analysis indicates that microdystrophin expression was highest in mice administered the microdystrophin tolerizing vector. Collectively these data clearly demonstrate not only specific and general suppression of host immune response in mice administered the tolerizing vector following gene therapy but elevated expression of the gene therapy replacement gene and muscle function in mice receiving the microdystrophin tolerizing vector following microdystrophin gene therapy.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method of reducing antibody production against dystrophin, the method comprising:
   a) delivering a Duchenne Muscular Dystrophy (DMD) gene therapy vector comprising an AAV6 vector and a dystrophin gene to a subject suffering from DMD;
   b) administering by intramuscular injection to the subject in a) an effective amount of a tolerizing DNA vector comprising a cDNA encoding human microdystrophin; wherein the tolerizing DNA vector, excluding the human microdystrophin cDNA, comprises 30 or fewer immunostimulatory CpG motifs and comprises at least one immunosuppressive GpG motif,
   wherein expression of the tolerizing DNA vector from step b) results in reducing antibody production against dystrophin.

2. The method according to claim 1, wherein the method improves the efficacy of the Duchenne Muscular Dystrophy (DMD) gene therapy vector when compared to a control subject.

3. A method of reducing antibody response to dystrophin and AAV6 capsid proteins, the method comprising:
   a) delivering a Duchenne Muscular Dystrophy (DMD) gene therapy vector comprising an AAV6 vector and a dystrophin gene to a subject suffering from DMD;
   b) administering by intramuscular injection to the subject in a) an effective amount of a tolerizing DNA vector, the tolerizing DNA vector comprising:
      i) a nucleic acid encoding human microdystrophin;
      ii) at least one immunosuppressive GpG motif and, excluding the nucleic acid of i), 30 or fewer immunostimulatory CpG motifs,
   wherein the method results in a reduced host antibody response to dystrophin and AAV6 capsid proteins.

4. The method according to claim 3, wherein the method improves the efficacy of the Duchenne Muscular Dystrophy (DMD) gene therapy vector when compared to a control subject.

* * * * *

SEQUENCE LISTING

```
<160> NUMBER OF SEQ ID NOS: 5

<210> SEQ ID NO 1
<211> LENGTH: 2999
<212> TYPE: DNA
<213> ORGANISM: Artificial Sequence
<220> FEATURE:
<223> OTHER INFORMATION: synthetic nucleic acid sequence

<400> SEQUENCE: 1
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccactag tccagtgtgg tggaattctg cagatatcca gcacagtggc     780
ggcggctcga gtctagaggg cccgtttaaa cccgctgatc agcctcgact gtgccttcta     840
```

```
gttgccagcc atctgttgtt tgcccctccc ccgtgccttc cttgaccctg gaaggtgcca      900
ctcccactgt cctttcctaa taaaatgagg aaattgcatc gcattgtctg agtaggtgtc      960
attctattct gggggggtggg gtggggcagg acagcaaggg ggaggattgg gaagacaata   1020
gcaggcatgc tggggatgcg gtgggctcta tggcttctac tgggcggttt tatggacagc   1080
aagcgaaccg gaattgccag ctggggcgcc ctctggtaag gttgggaagc cctgcaaagt   1140
aaactggatg gctttctcgc ggccaaggat ctgatgcgc aggggatcaa gctctgatca    1200
agagacagga tgaggatggt ttcgcatgat tgaacaagat ggattgcacg caggttctcc    1260
ggcagcttgg gtggagaggc tattcggcta tgactgggca caacagacaa tcggctgctc    1320
tgatgccgcc gtgttcaggc tgtcagcgca ggggcgcccg gttcttttttg tcaagaccga   1380 cctgtccggt gccctgaatg aactgcaaga cgaggcagcg cggctatcgt ggctggccac    1440
gacgggcgtt ccttgcgcag ctgtgctcga cgttgtcact gaagcgggaa gggactggct    1500
gctattgggc gaagtgccgg ggcaggatct cctgtcatct caccttgctc ctgccgagaa    1560
agtatccatc atggctgatg caatgcggcg gctgcatacg cttgatccgg ctacctgccc    1620
attcgaccac caagcgaaac atcgcatcga gcgagcacgt actcggatgg aagccggtct    1680
tgtcgatcag gatgatctgg acgaagagca tcaggggctc gcgccagccg aactgttcgc    1740
caggctcaag gcgagcatgc ccgacggcga ggatctcgtc gtgacccatg gcgatgcctg    1800
cttgccgaat atcatggtgg aaaatggcag gttttctgga ttcatcgact gtggccggct    1860
gggtgtggcg gacaggtatc aggacatagc gttggctacc cgtgatattg ctgaagagct    1920
tggcggcgaa tgggctgaca ggttcctcgt gctttacggt attgcggctc ccgattcgca    1980
gcgcattgcc ttctataggc ttcttgacga gttcttctga attattaacg cttacaattt    2040
cctgatgcgg tattttctcc ttacgcatct gtgcggtatt tcacaccgca tacaggtggc    2100
acttttcggg gaaatgtgcg cggaaccccc atttgtttat ttttctaaat acattcaaat    2160
atgtatccgc tcatgagaca ataaccctga taaatgcttc aataatagca cgtgctaaaa    2220 cttcatttttt aatttaaaag gatctaggtg aagatccttt ttgataatct catgaccaaa    2280
atcccttaac gtgagttttc gttccactga gcgtcagacc ccgtagaaaa gatcaaagga    2340
tcttcttgag atcctttttt tctgcgcgta atctgctgct tgcaaacaaa aaaaccaccg    2400
ctaccagcgg tggtttgttt gccggatcaa gagctaccaa ctcttttcc gaaggtaact    2460 ggcttcagca gagcgcagat accaaatact gtccttctag tgtagccgta gttaggccac    2520
cacttcaaga actctgtagc accgcctaca tacctcgctc tgctaatcct gttaccagtg    2580
gctgctgcca gtggcgataa gtcgtgtctt accgggttgg actcaagacg atagttaccg    2640
gataaggcgc agcggtcggg ctgaacgggg gttcgtgca cacagcccag cttggagcga    2700
acgacctaca ccgaactgag atacctacag cgtgagctat gagaaagcgc cacgcttccc    2760
gaagggagaa aggcggacag gtatccggta agcggcaggg tcggaacagg agagcgcacg    2820
agggagcttc caggggggaaa cgcctggtat ctttatagtc ctgtcgggtt tcgccacctc    2880
tgacttgagc gtcgattttt gtgatgctcg tcaggggggc ggagcctatg gaaaaacgcc    2940
agcaacgcgg ccttttacg gttcctgggc ttttgctggc cttttgctca catgttctt     2999
```

<210> SEQ ID NO 2
<211> LENGTH: 5670
<212> TYPE: DNA
<213> ORGANISM: Artificial Sequence
<220> FEATURE:

<223> OTHER INFORMATION: synthetic nucleic acid sequence

<400> SEQUENCE: 2

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca tagggactt tccattgacg tcaatgggtg gagtatttac ggtaaactgc      360
ccacttggca gtacatcaag tgtatcatat gccaagtccg cccctattg acgtcaatga      420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca gtctccacc ccattgacgt      600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaaaattg gatctccatt cgccattcag    1080
gctgcgcaac tgctgggaag gacgatcaga gcgggcctct tcgctattac gccagctggc    1140
gaaagggacg tggcaagcaa ggcgattaag ttgagttacg ccaggatttt cccagtcacg    1200
acgttgtaaa acgacggcca gagaattata atacgactca ctatagggcg aattcggatc    1260
cttgctagcc tcgagacgcg tgatatcttt ccgggggta ccgtcgactg cggccgcgaa     1320
ttccaagctt gagtattcta tcgtgtcacc taaataactt ggcgtaatca tggtcatatc    1380
tgtttcctgt gtgaaattgt tatccgctca caattccaca caacatacga gccggaagca    1440
taaagtgtaa agcctggggt gcctaatgag tgagctaact cacattaatt gcgttgcgcg    1500
atgcttccat tttgtgaggg ttaatgcttc gagaagacat gataagatac attgatgagt    1560
ttggacaaac cacaacaaga atgcagtgaa aaaaatgctt tatttgtgaa atttgtgatg    1620
ctattgcttt atttgtaacc attataagct gcaataaaca agttaacaac aacaattgca    1680
ttcattttat gtttcaggtt caggggggaga tgtgggaggt tttttaaagc aagtaaaacc    1740
tctacaaatg tggtaaaatc cgataaggat cgattccgga gcctgaatgg cgaatggacg    1800
cgccctgtag cggcgcatta agcgcggcgg gtgtggtggt tacgcgcacg tgaccgctac    1860
acttgccagc gccctagcgc ccgctccttt cgctttcttc ccttcctttc tcgccacgtt    1920
cgccggcttt ccccgtcaag ctctaaatcg ggggctccct ttagggttcc gatttagtgc    1980
tttacggcac ctcgacccca aaaaacttga ttagggtgat ggttcacgta gtgggccatc    2040
gccctgatag acgttttttc gcccttgac gttggagtcc acgttcttta atagtggact     2100
cttgttccaa actggaacaa cactcaaccc tatctcggtc tattcttttg atttataagg    2160
gattttgccg atttcggcct attggttaaa aaatgagctc atttaacaaa atttaacgc     2220
gaattttaac aaaatattaa cgcttacaat ttcgcctgtg taccttctga ggcggaaaga    2280
```

-continued

```
accagctgtg gaatgtgtgt cagttagggt gtggaaagtc cccaggctcc ccagcaggca    2340
gaagtatgca aagcatgcat ctcaattagt cagcaaccag gtgtggaaag tccccaggct    2400
ccccagcagg cagaagtatg caaagcatgc atctcaatta gtcagcaacc atagtcccgc    2460
ccctaactcc gcccatcccg cccctaactc cgcccagttc cgcccattct ccgcccatg     2520 gctgactaat ttttttatt tatgcagagg ccgaggccgc ctcggcctct gagctattcc     2580
agaagtagtg aggaggcttt tttggaggcc taggcttttg caaaaagctt gattcttctg    2640
acacaacagt ctcgaactta aggctagagc caccatgatt gaacaagatg gattgcacgc    2700
aggttctccg gccgcttggg tggagaggct attcggctat gactgggcac aacagacaat    2760
cggctgctct gatgccgccg tgttccggct gtcagcgcag gggcgcccgg ttcttttgt     2820 caagaccgac ctgtccggtg ccctgaatga actgcaggac gaggcagcgc ggctatcgtg    2880
gctggccacg acgggcgttc cttgcgcagc tgtgctcgac gttgtcactg aagcgggaag    2940
ggactggctg ctattgggcg aagtgccggg gcaggatctc ctgtcatctc accttgctcc    3000
tgccgagaaa gtatccatca tggctgatgc aatgcggcgg ctgcatacgc ttgatccggc    3060
tacctgccca ttcgaccacc aagcgaaaca tcgcatcgag cgagcacgta ctcggatgga    3120
agccggtctt gtcgatcagg atgatctgga cgaagagcat caggggctcg cgccagccga    3180
actgttcgcc aggctcaagg cgcgcatgcc cgacggcgag gatctcgtcg tgacccatgg    3240
cgatgcctgc ttgccgaata tcatggtgga aaatggccgc ttttctggat tcatcgactg    3300
tggccggctg ggtgtggcgg accgctatca ggacatagcg ttggctaccc gtgatattgc    3360
tgaagagctt ggcggcgaat gggctgaccg cttcctcgtg ctttacggta tcgccgctcc    3420
cgattcgcag cgcatcgcct tctatcgcct tcttgacgag ttcttctgag cgggactctg    3480
gggttcgaaa tgaccgacca agcgacgccc aacctgccat cacgatggcc gcaataaaat    3540
atctttattt tcattacatc tgtgtgttgg ttttttgtgt gaagatccgc gtatggtgca    3600
ctctcagtac aatctgctct gatgccgcat agttaagcca gccccgacac ccgccaacac    3660
ccgctgacgc gccctgacgg gcttgtctgc tcccggcatc cgcttacaga caagctgtga    3720
ccgtctccgg gagctgcatg tgtcagaggt tttcaccgtc atcaccgaaa cgcgcgagac    3780
gaaagggcct cgtgatacgc ctatttttat aggttaatgt catgataata atggtttctt    3840
agacgtcagg tggcacttt cggggaaatg tgcgcggaac ccctatttgt ttattttct     3900 aaatacattc aaatatgtat ccgctcatga caataaacc ctgataaatg cttcaataat    3960
attgaaaaag gaagagtatg agtattcaac atttccgtgt cgcccttatt ccctttttg    4020 cggcattttg ccttcctgtt tttgctcacc cagaaacgct ggtgaaagta aaagatgctg    4080
aagatcagtt gggtgcacga gtgggttaca tcgaactgga tctcaacagc ggtaagatcc    4140
ttgagagttt tcgccccgaa gaacgttttc caatgatgag cacttttaaa gttctgctat    4200
gtggcgcggt attatcccgt attgacgccg ggcaagagca actcggtcgc cgcatacact    4260
attctcagaa tgacttggtt gagtactcac cagtcacaga aaagcatctt acggatggca    4320
tgacagtaag agaattatgc agtgctgcca taaccatgag tgataacact gcggccaact    4380
tacttctgac aacgatcgga ggaccgaagg agctaaccgc ttttttgcac aacatggggg    4440
atcatgtaac tcgccttgat cgttgggaac cggagctgaa tgaagccata ccaaacgacg    4500
agcgtgacac cacgatgcct gtagcaatgg caacaacgtt gcgcaaacta ttaactggcg    4560
aactacttac tctagcttcc cggcaacaat taatagactg gatggaggcg gataaagttg    4620
```

```
caggaccact tctgcgctcg gcccttccgg ctggctggtt tattgctgat aaatctggag   4680
ccggtgagcg tgggtctcgc ggtatcattg cagcactggg gccagatggt aagccctccc   4740
gtatcgtagt tatctacacg acggggagtc aggcaactat ggatgaacga aatagacaga   4800
tcgctgagat aggtgcctca ctgattaagc attggtaact gtcagaccaa gtttactcat   4860
atatacttta gattgattta aaacttcatt tttaatttaa aaggatctag gtgaagatcc   4920
tttttgataa tctcatgacc aaaatccctt aacgtgagtt ttcgttccac tgagcgtcag   4980
accccgtaga aaagatcaaa ggatcttctt gagatccttt tttctgcgc gtaatctgct    5040 gcttgcaaac aaaaaaacca ccgctaccag cggtggtttg tttgccggat caagagctac   5100
caactctttt tccgaaggta actggcttca gcagagcgca gataccaaat actgtccttc   5160
tagtgtagcc gtagttaggc caccacttca agaactctgt agcaccgcct acatacctcg   5220
ctctgctaat cctgttacca gtggctgctg ccagtggcga taagtcgtgt cttaccgggt   5280
tggactcaag acgatagtta ccggataagg cgcagcggtc gggctgaacg gggggttcgt   5340
gcacacagcc cagcttggag cgaacgacct acaccgaact gagataccta cagcgtgagc   5400
tatgagaaag cgccacgctt cccgaaggga gaaaggcgga caggtatccg gtaagcggca   5460
gggtcggaac aggagagcgc acgagggagc ttccaggggg aaacgcctgg tatctttata   5520
gtcctgtcgg gtttcgccac ctctgacttg agcgtcgatt tttgtgatgc tcgtcagggg   5580
ggcggagcct atggaaaaac gccagcaacg cggccttttt acggttcctg gccttttgct   5640
ggccttttgc tcacatggct cgacagatct                                    5670

<210> SEQ ID NO 3
<211> LENGTH: 133
<212> TYPE: DNA
<213> ORGANISM: Artificial Sequence
<220> FEATURE:
<223> OTHER INFORMATION: synthetic nucliec acid sequence

<400> SEQUENCE: 3
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                     133

<210> SEQ ID NO 4
<211> LENGTH: 3677
<212> TYPE: PRT
<213> ORGANISM: Homo sapiens

<400> SEQUENCE: 4
```

Met Glu Asp Glu Arg Glu Asp Val Gln Lys Lys Thr Phe Thr Lys Trp
1               5                   10                  15

Val Asn Ala Gln Phe Ser Lys Phe Gly Lys Gln His Ile Glu Asn Leu
            20                  25                  30

Phe Ser Asp Leu Gln Asp Gly Arg Arg Leu Leu Asp Leu Leu Glu Gly
        35                  40                  45

Leu Thr Gly Gln Lys Leu Pro Lys Glu Lys Gly Ser Thr Arg Val His
    50                  55                  60

Ala Leu Asn Asn Val Asn Lys Ala Leu Arg Val Leu Gln Asn Asn Asn
65                  70                  75                  80

Val Asp Leu Val Asn Ile Gly Ser Thr Asp Ile Val Asp Gly Asn His
                85                  90                  95

Lys Leu Thr Leu Gly Leu Ile Trp Asn Ile Ile Leu His Trp Gln Val

```
                100                 105                 110
Lys Asn Val Met Lys Asn Ile Met Ala Gly Leu Gln Gln Thr Asn Ser
            115                 120                 125

Glu Lys Ile Leu Leu Ser Trp Val Arg Gln Ser Thr Arg Asn Tyr Pro
130                 135                 140

Gln Val Asn Val Ile Asn Phe Thr Thr Ser Trp Ser Asp Gly Leu Ala
145                 150                 155                 160

Leu Asn Ala Leu Ile His Ser His Arg Pro Asp Leu Phe Asp Trp Asn
                165                 170                 175

Ser Val Val Cys Gln Gln Ser Ala Thr Gln Arg Leu Glu His Ala Phe
                180                 185                 190

Asn Ile Ala Arg Tyr Gln Leu Gly Ile Glu Lys Leu Leu Asp Pro Glu
                195                 200                 205

Asp Val Asp Thr Thr Tyr Pro Asp Lys Lys Ser Ile Leu Met Tyr Ile
            210                 215                 220

Thr Ser Leu Phe Gln Val Leu Pro Gln Gln Val Ser Ile Glu Ala Ile
225                 230                 235                 240

Gln Glu Val Glu Met Leu Pro Arg Pro Pro Lys Val Thr Lys Glu Glu
                245                 250                 255

His Phe Gln Leu His His Gln Met His Tyr Ser Gln Gln Ile Thr Val
                260                 265                 270

Ser Leu Ala Gln Gly Tyr Glu Arg Thr Ser Ser Pro Lys Pro Arg Phe
                275                 280                 285

Lys Ser Tyr Ala Tyr Thr Gln Ala Ala Tyr Val Thr Thr Ser Asp Pro
            290                 295                 300

Thr Arg Ser Pro Phe Pro Ser Gln His Leu Glu Ala Pro Glu Asp Lys
305                 310                 315                 320

Ser Phe Gly Ser Ser Leu Met Glu Ser Glu Val Asn Leu Asp Arg Tyr
                325                 330                 335

Gln Thr Ala Leu Glu Glu Val Leu Ser Trp Leu Leu Ser Ala Glu Asp
                340                 345                 350

Thr Leu Gln Ala Gln Gly Glu Ile Ser Asn Asp Val Glu Val Val Lys
                355                 360                 365

Asp Gln Phe His Thr His Glu Gly Tyr Met Met Asp Leu Thr Ala His
            370                 375                 380

Gln Gly Arg Val Gly Asn Ile Leu Gln Leu Gly Ser Lys Leu Ile Gly
385                 390                 395                 400

Thr Gly Lys Leu Ser Glu Asp Glu Glu Thr Glu Val Gln Glu Gln Met
                405                 410                 415

Asn Leu Leu Asn Ser Arg Trp Glu Cys Leu Arg Val Ala Ser Met Glu
                420                 425                 430

Lys Gln Ser Asn Leu His Arg Val Leu Met Asp Leu Gln Asn Gln Lys
            435                 440                 445

Leu Lys Glu Leu Asn Asp Trp Leu Thr Lys Thr Glu Glu Arg Thr Arg
450                 455                 460

Lys Met Glu Glu Glu Pro Leu Gly Pro Asp Leu Glu Asp Leu Lys Arg
465                 470                 475                 480

Gln Val Gln Gln His Lys Val Leu Gln Glu Asp Leu Glu Gln Glu Gln
                485                 490                 495

Val Arg Val Asn Ser Leu Thr His Met Val Val Val Asp Glu Ser
            500                 505                 510

Ser Gly Asp His Ala Thr Ala Ala Leu Glu Glu Gln Leu Lys Val Leu
            515                 520                 525
```

```
Gly Asp Arg Trp Ala Asn Ile Cys Arg Trp Thr Glu Asp Arg Trp Val
    530                 535                 540

Leu Leu Gln Asp Ile Leu Leu Lys Trp Gln Arg Leu Thr Glu Glu Gln
545                 550                 555                 560

Cys Leu Phe Ser Ala Trp Leu Ser Glu Lys Glu Asp Ala Val Asn Lys
                565                 570                 575

Ile His Thr Thr Gly Phe Lys Asp Gln Asn Glu Met Leu Ser Ser Leu
                580                 585                 590

Gln Lys Leu Ala Val Leu Lys Ala Asp Leu Glu Lys Lys Lys Gln Ser
        595                 600                 605

Met Gly Lys Leu Tyr Ser Leu Lys Gln Asp Leu Leu Ser Thr Leu Lys
    610                 615                 620

Asn Lys Ser Val Thr Gln Lys Thr Glu Ala Trp Leu Asp Asn Phe Ala
625                 630                 635                 640

Arg Cys Trp Asp Asn Leu Val Gln Lys Leu Glu Lys Ser Thr Ala Gln
                645                 650                 655

Ile Ser Gln Ala Val Thr Thr Thr Gln Pro Ser Leu Thr Gln Thr Thr
                660                 665                 670

Val Met Glu Thr Val Thr Thr Val Thr Thr Arg Glu Gln Ile Leu Val
        675                 680                 685

Lys His Ala Gln Glu Glu Leu Pro Pro Pro Pro Gln Lys Lys Arg
    690                 695                 700

Gln Ile Thr Val Asp Ser Glu Ile Arg Lys Arg Leu Asp Val Asp Ile
705                 710                 715                 720

Thr Glu Leu His Ser Trp Ile Thr Arg Ser Glu Ala Val Leu Gln Ser
                725                 730                 735

Pro Glu Phe Ala Ile Phe Arg Lys Glu Gly Asn Phe Ser Asp Leu Lys
                740                 745                 750

Glu Lys Val Asn Ala Ile Glu Arg Glu Lys Ala Glu Lys Phe Arg Lys
        755                 760                 765

Leu Gln Asp Ala Ser Arg Ser Ala Gln Ala Leu Val Glu Gln Met Val
    770                 775                 780

Asn Glu Gly Val Asn Ala Asp Ser Ile Lys Gln Ala Ser Glu Gln Leu
785                 790                 795                 800

Asn Ser Arg Trp Ile Glu Phe Cys Gln Leu Leu Ser Glu Arg Leu Asn
                805                 810                 815

Trp Leu Glu Tyr Gln Asn Asn Ile Ile Ala Phe Tyr Asn Gln Leu Gln
                820                 825                 830

Gln Leu Glu Gln Met Thr Thr Thr Ala Glu Asn Trp Leu Lys Ile Gln
        835                 840                 845

Pro Thr Thr Pro Ser Glu Pro Thr Ala Ile Lys Ser Gln Leu Lys Ile
    850                 855                 860

Cys Lys Asp Glu Val Asn Arg Leu Ser Gly Leu Gln Pro Gln Ile Glu
865                 870                 875                 880

Arg Leu Lys Ile Gln Ser Ile Ala Leu Lys Glu Lys Gly Gln Gly Pro
                885                 890                 895

Met Phe Leu Asp Ala Asp Phe Val Ala Phe Thr Asn His Phe Lys Gln
                900                 905                 910

Val Phe Ser Asp Val Gln Ala Arg Glu Lys Glu Leu Gln Thr Ile Phe
        915                 920                 925

Asp Thr Leu Pro Pro Met Arg Tyr Gln Glu Thr Met Ser Ala Ile Arg
    930                 935                 940
```

```
Thr Trp Val Gln Gln Ser Glu Thr Lys Leu Ser Ile Pro Gln Leu Ser
945                 950                 955                 960

Val Thr Asp Tyr Glu Ile Met Glu Gln Arg Leu Gly Glu Leu Gln Ala
                965                 970                 975

Leu Gln Ser Ser Leu Gln Glu Gln Gln Ser Gly Leu Tyr Tyr Leu Ser
            980                 985                 990

Thr Thr Val Lys Glu Met Ser Lys Lys Ala Pro Ser Glu Ile Ser Arg
        995                 1000                1005

Lys Tyr Gln Ser Glu Phe Glu Ile Glu Gly Arg Trp Lys Lys
    1010                1015                1020

Leu Ser Ser Gln Leu Val Glu His Cys Gln Lys Leu Glu Glu Gln
    1025                1030                1035

Met Asn Lys Leu Arg Lys Ile Gln Asn His Ile Gln Thr Leu Lys
    1040                1045                1050

Lys Trp Met Ala Glu Val Asp Val Phe Leu Lys Glu Glu Trp Pro
    1055                1060                1065

Ala Leu Gly Asp Ser Glu Ile Leu Lys Lys Gln Leu Lys Gln Cys
    1070                1075                1080

Arg Leu Leu Val Ser Asp Ile Gln Thr Ile Gln Pro Ser Leu Asn
    1085                1090                1095

Ser Val Asn Glu Gly Gly Gln Lys Ile Lys Asn Glu Ala Glu Pro
    1100                1105                1110

Glu Phe Ala Ser Arg Leu Glu Thr Glu Leu Lys Glu Leu Asn Thr
    1115                1120                1125

Gln Trp Asp His Met Cys Gln Val Tyr Ala Arg Lys Glu Ala
    1130                1135                1140

Leu Lys Gly Gly Leu Glu Lys Thr Val Ser Leu Gln Lys Asp Leu
    1145                1150                1155

Ser Glu Met His Glu Trp Met Thr Gln Ala Glu Glu Tyr Leu
    1160                1165                1170

Glu Arg Asp Phe Glu Tyr Lys Thr Pro Asp Glu Leu Gln Lys Ala
    1175                1180                1185

Val Glu Glu Met Lys Arg Ala Lys Glu Glu Ala Gln Gln Lys Glu
    1190                1195                1200

Ala Lys Val Lys Leu Leu Thr Glu Ser Val Asn Ser Val Ile Ala
    1205                1210                1215

Gln Ala Pro Pro Val Ala Gln Glu Ala Leu Lys Lys Glu Leu Glu
    1220                1225                1230

Thr Leu Thr Thr Asn Tyr Gln Trp Leu Cys Thr Arg Leu Asn Gly
    1235                1240                1245

Lys Cys Lys Thr Leu Glu Glu Val Trp Ala Cys Trp His Glu Leu
    1250                1255                1260

Leu Ser Tyr Leu Glu Lys Ala Asn Lys Trp Leu Asn Glu Val Glu
    1265                1270                1275

Phe Lys Leu Lys Thr Thr Glu Asn Ile Pro Gly Gly Ala Glu Glu
    1280                1285                1290

Ile Ser Glu Val Leu Asp Ser Leu Glu Asn Leu Met Arg His Ser
    1295                1300                1305

Glu Asp Asn Pro Asn Gln Ile Arg Ile Leu Ala Gln Thr Leu Thr
    1310                1315                1320

Asp Gly Gly Val Met Asp Glu Leu Ile Asn Glu Glu Leu Glu Thr
    1325                1330                1335

Phe Asn Ser Arg Trp Arg Glu Leu His Glu Glu Ala Val Arg Arg
```

-continued

```
             1340                1345                1350

Gln  Lys  Leu  Leu  Glu  Gln  Ser  Ile  Gln  Ser  Ala  Gln  Glu  Thr  Glu
             1355                1360                1365

Lys  Ser  Leu  His  Leu  Ile  Gln  Glu  Ser  Leu  Thr  Phe  Ile  Asp  Lys
             1370                1375                1380

Gln  Leu  Ala  Ala  Tyr  Ile  Ala  Asp  Lys  Val  Asp  Ala  Ala  Gln  Met
             1385                1390                1395

Pro  Gln  Glu  Ala  Gln  Lys  Ile  Gln  Ser  Asp  Leu  Thr  Ser  His  Glu
             1400                1405                1410

Ile  Ser  Leu  Glu  Glu  Met  Lys  Lys  His  Asn  Gln  Gly  Lys  Glu  Ala
             1415                1420                1425

Ala  Gln  Arg  Val  Leu  Ser  Gln  Ile  Asp  Val  Ala  Gln  Lys  Lys  Leu
             1430                1435                1440

Gln  Asp  Val  Ser  Met  Lys  Phe  Arg  Leu  Phe  Gln  Lys  Pro  Ala  Asn
             1445                1450                1455

Phe  Glu  Gln  Arg  Leu  Gln  Glu  Ser  Lys  Met  Ile  Leu  Asp  Glu  Val
             1460                1465                1470

Lys  Met  His  Leu  Pro  Ala  Leu  Glu  Thr  Lys  Ser  Val  Glu  Gln  Glu
             1475                1480                1485

Val  Val  Gln  Ser  Gln  Leu  Asn  His  Cys  Val  Asn  Leu  Tyr  Lys  Ser
             1490                1495                1500

Leu  Ser  Glu  Val  Lys  Ser  Glu  Val  Glu  Met  Val  Ile  Lys  Thr  Gly
             1505                1510                1515

Arg  Gln  Ile  Val  Gln  Lys  Lys  Gln  Thr  Glu  Asn  Pro  Lys  Glu  Leu
             1520                1525                1530

Asp  Glu  Arg  Val  Thr  Ala  Leu  Lys  Leu  His  Tyr  Asn  Glu  Leu  Gly
             1535                1540                1545

Ala  Lys  Val  Thr  Glu  Arg  Lys  Gln  Gln  Leu  Glu  Lys  Cys  Leu  Lys
             1550                1555                1560

Leu  Ser  Arg  Lys  Met  Arg  Lys  Glu  Met  Asn  Val  Leu  Thr  Glu  Trp
             1565                1570                1575

Leu  Ala  Ala  Thr  Asp  Met  Glu  Leu  Thr  Lys  Arg  Ser  Ala  Val  Glu
             1580                1585                1590

Gly  Met  Pro  Ser  Asn  Leu  Asp  Ser  Glu  Val  Ala  Trp  Gly  Lys  Ala
             1595                1600                1605

Thr  Gln  Lys  Glu  Ile  Glu  Lys  Gln  Lys  Val  His  Leu  Lys  Ser  Ile
             1610                1615                1620

Thr  Glu  Val  Gly  Glu  Ala  Leu  Lys  Thr  Val  Leu  Gly  Lys  Lys  Glu
             1625                1630                1635

Thr  Leu  Val  Glu  Asp  Lys  Leu  Ser  Leu  Leu  Asn  Ser  Asn  Trp  Ile
             1640                1645                1650

Ala  Val  Thr  Ser  Arg  Ala  Glu  Glu  Trp  Leu  Asn  Leu  Leu  Leu  Glu
             1655                1660                1665

Tyr  Gln  Lys  His  Met  Glu  Thr  Phe  Asp  Gln  Asn  Val  Asp  His  Ile
             1670                1675                1680

Thr  Lys  Trp  Ile  Ile  Gln  Ala  Asp  Thr  Leu  Leu  Asp  Glu  Ser  Glu
             1685                1690                1695

Lys  Lys  Lys  Pro  Gln  Gln  Lys  Glu  Asp  Val  Leu  Lys  Arg  Leu  Lys
             1700                1705                1710

Ala  Glu  Leu  Asn  Asp  Ile  Arg  Pro  Lys  Val  Asp  Ser  Thr  Arg  Asp
             1715                1720                1725

Gln  Ala  Ala  Asn  Leu  Met  Ala  Asn  Arg  Gly  Asp  His  Cys  Arg  Lys
             1730                1735                1740
```

```
Leu Val Glu Pro Gln Ile Ser Glu Leu Asn His Arg Phe Ala Ala
1745                1750                1755

Ile Ser His Arg Ile Lys Thr Gly Lys Ala Ser Ile Pro Leu Lys
1760                1765                1770

Glu Leu Glu Gln Phe Asn Ser Asp Ile Gln Lys Leu Leu Glu Pro
1775                1780                1785

Leu Glu Ala Glu Ile Gln Gln Gly Val Asn Leu Lys Glu Glu Asp
1790                1795                1800

Phe Asn Lys Asp Met Asn Glu Asp Asn Glu Gly Thr Val Lys Glu
1805                1810                1815

Leu Leu Gln Arg Gly Asp Asn Leu Gln Gln Arg Ile Thr Asp Glu
1820                1825                1830

Arg Lys Arg Glu Glu Ile Lys Ile Lys Gln Gln Leu Leu Gln Thr
1835                1840                1845

Lys His Asn Ala Leu Lys Asp Leu Arg Ser Gln Arg Arg Lys Lys
1850                1855                1860

Ala Leu Glu Ile Ser His Gln Trp Tyr Gln Tyr Lys Arg Gln Ala
1865                1870                1875

Asp Asp Leu Leu Lys Cys Leu Asp Asp Ile Glu Lys Lys Leu Ala
1880                1885                1890

Ser Leu Pro Glu Pro Arg Asp Glu Arg Lys Ile Lys Glu Ile Asp
1895                1900                1905

Arg Glu Leu Gln Lys Lys Lys Glu Glu Leu Asn Ala Val Arg Arg
1910                1915                1920

Gln Ala Glu Gly Leu Ser Glu Asp Gly Ala Ala Met Ala Val Glu
1925                1930                1935

Pro Thr Gln Ile Gln Leu Ser Lys Arg Trp Arg Glu Ile Glu Ser
1940                1945                1950

Lys Phe Ala Gln Phe Arg Arg Leu Asn Phe Ala Gln Ile His Thr
1955                1960                1965

Val Arg Glu Glu Thr Met Met Val Met Thr Glu Asp Met Pro Leu
1970                1975                1980

Glu Ile Ser Tyr Val Pro Ser Thr Tyr Leu Thr Glu Ile Thr His
1985                1990                1995

Val Ser Gln Ala Leu Leu Glu Val Glu Gln Leu Leu Asn Ala Pro
2000                2005                2010

Asp Leu Cys Ala Lys Asp Phe Glu Asp Leu Phe Lys Gln Glu Glu
2015                2020                2025

Ser Leu Lys Asn Ile Lys Asp Ser Leu Gln Gln Ser Ser Gly Arg
2030                2035                2040

Ile Asp Ile Ile His Ser Lys Lys Thr Ala Ala Leu Gln Ser Ala
2045                2050                2055

Thr Pro Val Glu Arg Val Lys Leu Gln Glu Ala Leu Ser Gln Leu
2060                2065                2070

Asp Phe Gln Trp Glu Lys Val Asn Lys Met Tyr Lys Asp Arg Gln
2075                2080                2085

Gly Arg Phe Asp Arg Ser Val Glu Lys Trp Arg Arg Phe His Tyr
2090                2095                2100

Asp Ile Lys Ile Phe Asn Gln Trp Leu Thr Glu Ala Glu Gln Phe
2105                2110                2115

Leu Arg Lys Thr Gln Ile Pro Glu Asn Trp Glu His Ala Lys Tyr
2120                2125                2130
```

```
-continued

Lys Trp Tyr Leu Lys Glu Leu Gln Asp Gly Ile Gly Gln Arg Gln
    2135                2140                2145

Thr Val Val Arg Thr Leu Asn Ala Thr Gly Glu Glu Ile Ile Gln
    2150                2155                2160

Gln Ser Ser Lys Thr Asp Ala Ser Ile Leu Gln Glu Lys Leu Gly
    2165                2170                2175

Ser Leu Asn Leu Arg Trp Gln Glu Val Cys Lys Gln Leu Ser Asp
    2180                2185                2190

Arg Lys Lys Arg Leu Glu Glu Gln Lys Asn Ile Leu Ser Glu Phe
    2195                2200                2205

Gln Arg Asp Leu Asn Glu Phe Val Leu Trp Leu Glu Glu Ala Asp
    2210                2215                2220

Asn Ile Ala Ser Ile Pro Leu Glu Pro Gly Lys Glu Gln Gln Leu
    2225                2230                2235

Lys Glu Lys Leu Glu Gln Val Lys Leu Leu Val Glu Glu Leu Pro
    2240                2245                2250

Leu Arg Gln Gly Ile Leu Lys Gln Leu Asn Glu Thr Gly Gly Pro
    2255                2260                2265

Val Leu Val Ser Ala Pro Ile Ser Pro Glu Glu Gln Asp Lys Leu
    2270                2275                2280

Glu Asn Lys Leu Lys Gln Thr Asn Leu Gln Trp Ile Lys Val Ser
    2285                2290                2295

Arg Ala Leu Pro Glu Lys Gln Gly Glu Ile Glu Ala Gln Ile Lys
    2300                2305                2310

Asp Leu Gly Gln Leu Glu Lys Lys Leu Glu Asp Leu Glu Glu Gln
    2315                2320                2325

Leu Asn His Leu Leu Leu Trp Leu Ser Pro Ile Arg Asn Gln Leu
    2330                2335                2340

Glu Ile Tyr Asn Gln Pro Asn Gln Glu Gly Pro Phe Asp Val Gln
    2345                2350                2355

Glu Thr Glu Ile Ala Val Gln Ala Lys Gln Pro Asp Val Glu Glu
    2360                2365                2370

Ile Leu Ser Lys Gly Gln His Leu Tyr Lys Glu Lys Pro Ala Thr
    2375                2380                2385

Gln Pro Val Lys Arg Lys Leu Glu Asp Leu Ser Ser Glu Trp Lys
    2390                2395                2400

Ala Val Asn Arg Leu Leu Gln Glu Leu Arg Ala Lys Gln Pro Asp
    2405                2410                2415

Leu Ala Pro Gly Leu Thr Thr Ile Gly Ala Ser Pro Thr Gln Thr
    2420                2425                2430

Val Thr Leu Val Thr Gln Pro Val Val Thr Lys Glu Thr Ala Ile
    2435                2440                2445

Ser Lys Leu Glu Met Pro Ser Ser Leu Met Leu Glu Val Pro Ala
    2450                2455                2460

Leu Ala Asp Phe Asn Arg Ala Trp Thr Glu Leu Thr Asp Trp Leu
    2465                2470                2475

Ser Leu Leu Asp Gln Val Ile Lys Ser Gln Arg Val Met Val Gly
    2480                2485                2490

Asp Leu Glu Asp Ile Asn Glu Met Ile Ile Lys Gln Lys Ala Thr
    2495                2500                2505

Met Gln Asp Leu Glu Gln Arg Arg Pro Gln Leu Glu Glu Leu Ile
    2510                2515                2520

Thr Ala Ala Gln Asn Leu Lys Asn Lys Thr Ser Asn Gln Glu Ala
```

-continued

```
            2525                2530                2535
Arg Thr Ile Ile Thr Asp Arg Ile Glu Arg Ile Gln Asn Gln Trp
    2540                2545                2550

Asp Glu Val Gln Glu His Leu Gln Asn Arg Arg Gln Gln Leu Asn
    2555                2560                2565

Glu Met Leu Lys Asp Ser Thr Gln Trp Leu Glu Ala Lys Glu Glu
    2570                2575                2580

Ala Glu Gln Val Leu Gly Gln Ala Arg Ala Lys Leu Glu Ser Trp
    2585                2590                2595

Lys Glu Gly Pro Tyr Thr Val Asp Ala Ile Gln Lys Lys Ile Thr
    2600                2605                2610

Glu Thr Lys Gln Leu Ala Lys Asp Leu Arg Gln Trp Gln Thr Asn
    2615                2620                2625

Val Asp Val Ala Asn Asp Leu Ala Leu Lys Leu Leu Arg Asp Tyr
    2630                2635                2640

Ser Ala Asp Asp Thr Arg Lys Val His Met Ile Thr Glu Asn Ile
    2645                2650                2655

Asn Ala Ser Trp Arg Ser Ile His Lys Arg Val Ser Glu Arg Glu
    2660                2665                2670

Ala Ala Leu Glu Glu Thr His Arg Leu Leu Gln Gln Phe Pro Leu
    2675                2680                2685

Asp Leu Glu Lys Phe Leu Ala Trp Leu Thr Glu Ala Glu Thr Thr
    2690                2695                2700

Ala Asn Val Leu Gln Asp Ala Thr Arg Lys Glu Arg Leu Leu Glu
    2705                2710                2715

Asp Ser Lys Gly Val Lys Glu Leu Met Lys Gln Trp Gln Asp Leu
    2720                2725                2730

Gln Gly Glu Ile Glu Ala His Thr Asp Val Tyr His Asn Leu Asp
    2735                2740                2745

Glu Asn Ser Gln Lys Ile Leu Arg Ser Leu Glu Gly Ser Asp Asp
    2750                2755                2760

Ala Val Leu Leu Gln Arg Arg Leu Asp Asn Met Asn Phe Lys Trp
    2765                2770                2775

Ser Glu Leu Arg Lys Lys Ser Leu Asn Ile Arg Ser His Leu Glu
    2780                2785                2790

Ala Ser Ser Asp Gln Trp Lys Arg Leu His Leu Ser Leu Gln Glu
    2795                2800                2805

Leu Leu Val Trp Leu Gln Leu Lys Asp Asp Glu Leu Ser Arg Gln
    2810                2815                2820

Ala Pro Ile Gly Gly Asp Phe Pro Ala Val Gln Lys Gln Asn Asp
    2825                2830                2835

Val His Arg Ala Phe Lys Arg Glu Leu Lys Thr Lys Glu Pro Val
    2840                2845                2850

Ile Met Ser Thr Leu Glu Thr Val Arg Ile Phe Leu Thr Glu Gln
    2855                2860                2865

Pro Leu Glu Gly Leu Glu Lys Leu Tyr Gln Glu Pro Arg Glu Leu
    2870                2875                2880

Pro Pro Glu Glu Arg Ala Gln Asn Val Thr Arg Leu Leu Arg Lys
    2885                2890                2895

Gln Ala Glu Glu Val Asn Thr Glu Trp Glu Lys Leu Asn Leu His
    2900                2905                2910

Ser Ala Asp Trp Gln Arg Lys Ile Asp Glu Thr Leu Glu Arg Leu
    2915                2920                2925
```

```
Gln Glu Leu Gln Glu Ala Thr Asp Glu Leu Asp Leu Lys Leu Arg
    2930            2935            2940

Gln Ala Glu Val Ile Lys Gly Ser Trp Gln Pro Val Gly Asp Leu
    2945            2950            2955

Leu Ile Asp Ser Leu Gln Asp His Leu Glu Lys Val Lys Ala Leu
    2960            2965            2970

Arg Gly Glu Ile Ala Pro Leu Lys Glu Asn Val Ser His Val Asn
    2975            2980            2985

Asp Leu Ala Arg Gln Leu Thr Thr Leu Gly Ile Gln Leu Ser Pro
    2990            2995            3000

Tyr Asn Leu Ser Thr Leu Glu Asp Leu Asn Thr Arg Trp Lys Leu
    3005            3010            3015

Leu Gln Val Ala Val Glu Asp Arg Val Arg Gln Leu His Glu Ala
    3020            3025            3030

His Arg Asp Phe Gly Pro Ala Ser Gln His Phe Leu Ser Thr Ser
    3035            3040            3045

Val Gln Gly Pro Trp Glu Arg Ala Ile Ser Pro Asn Lys Val Pro
    3050            3055            3060

Tyr Tyr Ile Asn His Glu Thr Gln Thr Thr Cys Trp Asp His Pro
    3065            3070            3075

Lys Met Thr Glu Leu Tyr Gln Ser Leu Ala Asp Leu Asn Asn Val
    3080            3085            3090

Arg Phe Ser Ala Tyr Arg Thr Ala Met Lys Leu Arg Arg Leu Gln
    3095            3100            3105

Lys Ala Leu Cys Leu Asp Leu Leu Ser Leu Ser Ala Ala Cys Asp
    3110            3115            3120

Ala Leu Asp Gln His Asn Leu Lys Gln Asn Asp Gln Pro Met Asp
    3125            3130            3135

Ile Leu Gln Ile Ile Asn Cys Leu Thr Thr Ile Tyr Asp Arg Leu
    3140            3145            3150

Glu Gln Glu His Asn Asn Leu Val Asn Val Pro Leu Cys Val Asp
    3155            3160            3165

Met Cys Leu Asn Trp Leu Leu Asn Val Tyr Asp Thr Gly Arg Thr
    3170            3175            3180

Gly Arg Ile Arg Val Leu Ser Phe Lys Thr Gly Ile Ile Ser Leu
    3185            3190            3195

Cys Lys Ala His Leu Glu Asp Lys Tyr Arg Tyr Leu Phe Lys Gln
    3200            3205            3210

Val Ala Ser Ser Thr Gly Phe Cys Asp Gln Arg Arg Leu Gly Leu
    3215            3220            3225

Leu Leu His Asp Ser Ile Gln Ile Pro Arg Gln Leu Gly Glu Val
    3230            3235            3240

Ala Ser Phe Gly Gly Ser Asn Ile Glu Pro Ser Val Arg Ser Cys
    3245            3250            3255

Phe Gln Phe Ala Asn Asn Lys Pro Glu Ile Glu Ala Ala Leu Phe
    3260            3265            3270

Leu Asp Trp Met Arg Leu Glu Pro Gln Ser Met Val Trp Leu Pro
    3275            3280            3285

Val Leu His Arg Val Ala Ala Ala Glu Thr Ala Lys His Gln Ala
    3290            3295            3300

Lys Cys Asn Ile Cys Lys Glu Cys Pro Ile Ile Gly Phe Arg Tyr
    3305            3310            3315
```

Arg Ser Leu Lys His Phe Asn Tyr Asp Ile Cys Gln Ser Cys Phe
3320                3325                3330

Phe Ser Gly Arg Val Ala Lys Gly His Lys Met His Tyr Pro Met
3335                3340                3345

Val Glu Tyr Cys Thr Pro Thr Thr Ser Gly Glu Asp Val Arg Asp
3350                3355                3360

Phe Ala Lys Val Leu Lys Asn Lys Phe Arg Thr Lys Arg Tyr Phe
3365                3370                3375

Ala Lys His Pro Arg Met Gly Tyr Leu Pro Val Gln Thr Val Leu
3380                3385                3390

Glu Gly Asp Asn Met Glu Thr Pro Val Thr Leu Ile Asn Phe Trp
3395                3400                3405

Pro Val Asp Ser Ala Pro Ala Ser Ser Pro Gln Leu Ser His Asp
3410                3415                3420

Asp Thr His Ser Arg Ile Glu His Tyr Ala Ser Arg Leu Ala Glu
3425                3430                3435

Met Glu Asn Ser Asn Gly Ser Tyr Leu Asn Asp Ser Ile Ser Pro
3440                3445                3450

Asn Glu Ser Ile Asp Asp Glu His Leu Leu Ile Gln His Tyr Cys
3455                3460                3465

Gln Ser Leu Asn Gln Asp Ser Pro Leu Ser Gln Pro Arg Ser Pro
3470                3475                3480

Ala Gln Ile Leu Ile Ser Leu Glu Ser Glu Glu Arg Gly Glu Leu
3485                3490                3495

Glu Arg Ile Leu Ala Asp Leu Glu Glu Glu Asn Arg Asn Leu Gln
3500                3505                3510

Ala Glu Tyr Asp Arg Leu Lys Gln Gln His Glu His Lys Gly Leu
3515                3520                3525

Ser Pro Leu Pro Ser Pro Pro Glu Met Met Pro Thr Ser Pro Gln
3530                3535                3540

Ser Pro Arg Asp Ala Glu Leu Ile Ala Glu Ala Lys Leu Leu Arg
3545                3550                3555

Gln His Lys Gly Arg Leu Glu Ala Arg Met Gln Ile Leu Glu Asp
3560                3565                3570

His Asn Lys Gln Leu Glu Ser Gln Leu His Arg Leu Arg Gln Leu
3575                3580                3585

Leu Glu Gln Pro Gln Ala Glu Ala Lys Val Asn Gly Thr Thr Val
3590                3595                3600

Ser Ser Pro Ser Thr Ser Leu Gln Arg Ser Asp Ser Ser Gln Pro
3605                3610                3615

Met Leu Leu Arg Val Val Gly Ser Gln Thr Ser Asp Ser Met Gly
3620                3625                3630

Glu Glu Asp Leu Leu Ser Pro Pro Gln Asp Thr Ser Thr Gly Leu
3635                3640                3645

Glu Glu Val Met Glu Gln Leu Asn Asn Ser Phe Pro Ser Ser Arg
3650                3655                3660

Gly Arg Asn Thr Pro Gly Lys Pro Met Arg Glu Asp Thr Met
3665                3670                3675

<210> SEQ ID NO 5
<211> LENGTH: 3685
<212> TYPE: PRT
<213> ORGANISM: Homo sapiens

<400> SEQUENCE: 5

-continued

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
        50                  55                  60

Glu Lys Gly Ser Thr Arg Val His Ala Leu Asn Asn Val Asn Lys Ala
65              70                  75                  80

Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
            115                 120                 125

Ala Gly Leu Gln Gln Thr Asn Ser Glu Lys Ile Leu Leu Ser Trp Val
            130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
            165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
            210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
            275                 280                 285

Thr Ser Ser Pro Lys Pro Arg Phe Lys Ser Tyr Ala Tyr Thr Gln Ala
            290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
            325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
            355                 360                 365

Ser Asn Asp Val Glu Val Val Lys Asp Gln Phe His Thr His Glu Gly
            370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415
```

-continued

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
            435                 440                 445

Leu Met Asp Leu Gln Asn Gln Lys Leu Lys Glu Leu Asn Asp Trp Leu
            450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
            485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
            515                 520                 525

Leu Glu Glu Gln Leu Lys Val Leu Gly Asp Arg Trp Ala Asn Ile Cys
            530                 535                 540

Arg Trp Thr Glu Asp Arg Trp Val Leu Gln Asp Ile Leu Leu Lys
545                 550                 555                 560

Trp Gln Arg Leu Thr Glu Glu Gln Cys Leu Phe Ser Ala Trp Leu Ser
            565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
            595                 600                 605

Asp Leu Glu Lys Lys Lys Gln Ser Met Gly Lys Leu Tyr Ser Leu Lys
            610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
            645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
            675                 680                 685

Thr Thr Arg Glu Gln Ile Leu Val Lys His Ala Gln Glu Glu Leu Pro
690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
            725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
            755                 760                 765

Glu Lys Ala Glu Lys Phe Arg Lys Leu Gln Asp Ala Ser Arg Ser Ala
            770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
            805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr

```
                835                 840                 845
Ala Glu Asn Trp Leu Lys Ile Gln Pro Thr Thr Pro Ser Glu Pro Thr
    850                 855                 860
Ala Ile Lys Ser Gln Leu Lys Ile Cys Lys Asp Glu Val Asn Arg Leu
865                 870                 875                 880
Ser Asp Leu Gln Pro Gln Ile Glu Arg Leu Lys Ile Gln Ser Ile Ala
                885                 890                 895
Leu Lys Glu Lys Gly Gln Gly Pro Met Phe Leu Asp Ala Asp Phe Val
            900                 905                 910
Ala Phe Thr Asn His Phe Lys Gln Val Phe Ser Asp Val Gln Ala Arg
        915                 920                 925
Glu Lys Glu Leu Gln Thr Ile Phe Asp Thr Leu Pro Pro Met Arg Tyr
    930                 935                 940
Gln Glu Thr Met Ser Ala Ile Arg Thr Trp Val Gln Gln Ser Glu Thr
945                 950                 955                 960
Lys Leu Ser Ile Pro Gln Leu Ser Val Thr Asp Tyr Glu Ile Met Glu
                965                 970                 975
Gln Arg Leu Gly Glu Leu Gln Ala Leu Gln Ser Ser Leu Gln Glu Gln
            980                 985                 990
Gln Ser Gly Leu Tyr Tyr Leu Ser Thr Thr Val Lys Glu Met Ser Lys
        995                1000                1005
Lys Ala Pro Ser Glu Ile Ser Arg Lys Tyr Gln Ser Glu Phe Glu
    1010                1015                1020
Glu Ile Glu Gly Arg Trp Lys Lys Leu Ser Ser Gln Leu Val Glu
    1025                1030                1035
His Cys Gln Lys Leu Glu Glu Gln Met Asn Lys Leu Arg Lys Ile
    1040                1045                1050
Gln Asn His Ile Gln Thr Leu Lys Lys Trp Met Ala Glu Val Asp
    1055                1060                1065
Val Phe Leu Lys Glu Glu Trp Pro Ala Leu Gly Asp Ser Glu Ile
    1070                1075                1080
Leu Lys Lys Gln Leu Lys Gln Cys Arg Leu Leu Val Ser Asp Ile
    1085                1090                1095
Gln Thr Ile Gln Pro Ser Leu Asn Ser Val Asn Glu Gly Gly Gln
    1100                1105                1110
Lys Ile Lys Asn Glu Ala Glu Pro Glu Phe Ala Ser Arg Leu Glu
    1115                1120                1125
Thr Glu Leu Lys Glu Leu Asn Thr Gln Trp Asp His Met Cys Gln
    1130                1135                1140
Gln Val Tyr Ala Arg Lys Glu Ala Leu Lys Gly Gly Leu Glu Lys
    1145                1150                1155
Thr Val Ser Leu Gln Lys Asp Leu Ser Glu Met His Glu Trp Met
    1160                1165                1170
Thr Gln Ala Glu Glu Glu Tyr Leu Glu Arg Asp Phe Glu Tyr Lys
    1175                1180                1185
Thr Pro Asp Glu Leu Gln Lys Ala Val Glu Glu Met Lys Arg Ala
    1190                1195                1200
Lys Glu Glu Ala Gln Gln Lys Glu Ala Lys Val Lys Leu Leu Thr
    1205                1210                1215
Glu Ser Val Asn Ser Val Ile Ala Gln Ala Pro Pro Val Ala Gln
    1220                1225                1230
Glu Ala Leu Lys Lys Glu Leu Glu Thr Leu Thr Thr Asn Tyr Gln
    1235                1240                1245
```

```
Trp Leu Cys Thr Arg Leu Asn Gly Lys Cys Lys Thr Leu Glu Glu
    1250                1255                1260

Val Trp Ala Cys Trp His Glu Leu Leu Ser Tyr Leu Glu Lys Ala
    1265                1270                1275

Asn Lys Trp Leu Asn Glu Val Glu Phe Lys Leu Lys Thr Thr Glu
    1280                1285                1290

Asn Ile Pro Gly Gly Ala Glu Glu Ile Ser Glu Val Leu Asp Ser
    1295                1300                1305

Leu Glu Asn Leu Met Arg His Ser Glu Asp Asn Pro Asn Gln Ile
    1310                1315                1320

Arg Ile Leu Ala Gln Thr Leu Thr Asp Gly Gly Val Met Asp Glu
    1325                1330                1335

Leu Ile Asn Glu Glu Leu Glu Thr Phe Asn Ser Arg Trp Arg Glu
    1340                1345                1350

Leu His Glu Glu Ala Val Arg Arg Gln Lys Leu Leu Glu Gln Ser
    1355                1360                1365

Ile Gln Ser Ala Gln Glu Thr Glu Lys Ser Leu His Leu Ile Gln
    1370                1375                1380

Glu Ser Leu Thr Phe Ile Asp Lys Gln Leu Ala Ala Tyr Ile Ala
    1385                1390                1395

Asp Lys Val Asp Ala Ala Gln Met Pro Gln Glu Ala Gln Lys Ile
    1400                1405                1410

Gln Ser Asp Leu Thr Ser His Glu Ile Ser Leu Glu Glu Met Lys
    1415                1420                1425

Lys His Asn Gln Gly Lys Glu Ala Ala Gln Arg Val Leu Ser Gln
    1430                1435                1440

Ile Asp Val Ala Gln Lys Lys Leu Gln Asp Val Ser Met Lys Phe
    1445                1450                1455

Arg Leu Phe Gln Lys Pro Ala Asn Phe Glu Gln Arg Leu Gln Glu
    1460                1465                1470

Ser Lys Met Ile Leu Asp Glu Val Lys Met His Leu Pro Ala Leu
    1475                1480                1485

Glu Thr Lys Ser Val Glu Gln Glu Val Val Gln Ser Gln Leu Asn
    1490                1495                1500

His Cys Val Asn Leu Tyr Lys Ser Leu Ser Glu Val Lys Ser Glu
    1505                1510                1515

Val Glu Met Val Ile Lys Thr Gly Arg Gln Ile Val Gln Lys Lys
    1520                1525                1530

Gln Thr Glu Asn Pro Lys Glu Leu Asp Glu Arg Val Thr Ala Leu
    1535                1540                1545

Lys Leu His Tyr Asn Glu Leu Gly Ala Lys Val Thr Glu Arg Lys
    1550                1555                1560

Gln Gln Leu Glu Lys Cys Leu Lys Leu Ser Arg Lys Met Arg Lys
    1565                1570                1575

Glu Met Asn Val Leu Thr Glu Trp Leu Ala Ala Thr Asp Met Glu
    1580                1585                1590

Leu Thr Lys Arg Ser Ala Val Glu Gly Met Pro Ser Asn Leu Asp
    1595                1600                1605

Ser Glu Val Ala Trp Gly Lys Ala Thr Gln Lys Glu Ile Glu Lys
    1610                1615                1620

Gln Lys Val His Leu Lys Ser Ile Thr Glu Val Gly Glu Ala Leu
    1625                1630                1635
```

```
Lys Thr Val Leu Gly Lys Lys Glu Thr Leu Val Glu Asp Lys Leu
    1640            1645            1650

Ser Leu Leu Asn Ser Asn Trp Ile Ala Val Thr Ser Arg Ala Glu
    1655            1660            1665

Glu Trp Leu Asn Leu Leu Leu Glu Tyr Gln Lys His Met Glu Thr
    1670            1675            1680

Phe Asp Gln Asn Val Asp His Ile Thr Lys Trp Ile Ile Gln Ala
    1685            1690            1695

Asp Thr Leu Leu Asp Glu Ser Glu Lys Lys Lys Pro Gln Gln Lys
    1700            1705            1710

Glu Asp Val Leu Lys Arg Leu Lys Ala Glu Leu Asn Asp Ile Arg
    1715            1720            1725

Pro Lys Val Asp Ser Thr Arg Asp Gln Ala Ala Asn Leu Met Ala
    1730            1735            1740

Asn Arg Gly Asp His Cys Arg Lys Leu Val Glu Pro Gln Ile Ser
    1745            1750            1755

Glu Leu Asn His Arg Phe Ala Ala Ile Ser His Arg Ile Lys Thr
    1760            1765            1770

Gly Lys Ala Ser Ile Pro Leu Lys Glu Leu Glu Gln Phe Asn Ser
    1775            1780            1785

Asp Ile Gln Lys Leu Leu Glu Pro Leu Glu Ala Glu Ile Gln Gln
    1790            1795            1800

Gly Val Asn Leu Lys Glu Glu Asp Phe Asn Lys Asp Met Asn Glu
    1805            1810            1815

Asp Asn Glu Gly Thr Val Lys Glu Leu Leu Gln Arg Gly Asp Asn
    1820            1825            1830

Leu Gln Gln Arg Ile Thr Asp Glu Arg Lys Arg Glu Glu Ile Lys
    1835            1840            1845

Ile Lys Gln Gln Leu Leu Gln Thr Lys His Asn Ala Leu Lys Asp
    1850            1855            1860

Leu Arg Ser Gln Arg Arg Lys Lys Ala Leu Glu Ile Ser His Gln
    1865            1870            1875

Trp Tyr Gln Tyr Lys Arg Gln Ala Asp Asp Leu Leu Lys Cys Leu
    1880            1885            1890

Asp Asp Ile Glu Lys Lys Leu Ala Ser Leu Pro Glu Pro Arg Asp
    1895            1900            1905

Glu Arg Lys Ile Lys Glu Ile Asp Arg Glu Leu Gln Lys Lys Lys
    1910            1915            1920

Glu Glu Leu Asn Ala Val Arg Arg Gln Ala Glu Gly Leu Ser Glu
    1925            1930            1935

Asp Gly Ala Ala Met Ala Val Glu Pro Thr Gln Ile Gln Leu Ser
    1940            1945            1950

Lys Arg Trp Arg Glu Ile Glu Ser Lys Phe Ala Gln Phe Arg Arg
    1955            1960            1965

Leu Asn Phe Ala Gln Ile His Thr Val Arg Glu Glu Thr Met Met
    1970            1975            1980

Val Met Thr Glu Asp Met Pro Leu Glu Ile Ser Tyr Val Pro Ser
    1985            1990            1995

Thr Tyr Leu Thr Glu Ile Thr His Val Ser Gln Ala Leu Leu Glu
    2000            2005            2010

Val Glu Gln Leu Leu Asn Ala Pro Asp Leu Cys Ala Lys Asp Phe
    2015            2020            2025

Glu Asp Leu Phe Lys Gln Glu Glu Ser Leu Lys Asn Ile Lys Asp
```

-continued

```
              2030                2035                2040
Ser Leu Gln Gln Ser Ser Gly Arg Ile Asp Ile Ile His Ser Lys
      2045                2050                2055
Lys Thr Ala Ala Leu Gln Ser Ala Thr Pro Val Glu Arg Val Lys
      2060                2065                2070
Leu Gln Glu Ala Leu Ser Gln Leu Asp Phe Gln Trp Glu Lys Val
      2075                2080                2085
Asn Lys Met Tyr Lys Asp Arg Gln Gly Arg Phe Asp Arg Ser Val
      2090                2095                2100
Glu Lys Trp Arg Arg Phe His Tyr Asp Ile Lys Ile Phe Asn Gln
      2105                2110                2115
Trp Leu Thr Glu Ala Glu Gln Phe Leu Arg Lys Thr Gln Ile Pro
      2120                2125                2130
Glu Asn Trp Glu His Ala Lys Tyr Lys Trp Tyr Leu Lys Glu Leu
      2135                2140                2145
Gln Asp Gly Ile Gly Gln Arg Gln Thr Val Val Arg Thr Leu Asn
      2150                2155                2160
Ala Thr Gly Glu Glu Ile Ile Gln Gln Ser Ser Lys Thr Asp Ala
      2165                2170                2175
Ser Ile Leu Gln Glu Lys Leu Gly Ser Leu Asn Leu Arg Trp Gln
      2180                2185                2190
Glu Val Cys Lys Gln Leu Ser Asp Arg Lys Lys Arg Leu Glu Glu
      2195                2200                2205
Gln Lys Asn Ile Leu Ser Glu Phe Gln Arg Asp Leu Asn Glu Phe
      2210                2215                2220
Val Leu Trp Leu Glu Glu Ala Asp Asn Ile Ala Ser Ile Pro Leu
      2225                2230                2235
Glu Pro Gly Lys Glu Gln Gln Leu Lys Glu Lys Leu Glu Gln Val
      2240                2245                2250
Lys Leu Leu Val Glu Glu Leu Pro Leu Arg Gln Gly Ile Leu Lys
      2255                2260                2265
Gln Leu Asn Glu Thr Gly Gly Pro Val Leu Val Ser Ala Pro Ile
      2270                2275                2280
Ser Pro Glu Glu Gln Asp Lys Leu Glu Asn Lys Leu Lys Gln Thr
      2285                2290                2295
Asn Leu Gln Trp Ile Lys Val Ser Arg Ala Leu Pro Glu Lys Gln
      2300                2305                2310
Gly Glu Ile Glu Ala Gln Ile Lys Asp Leu Gly Gln Leu Glu Lys
      2315                2320                2325
Lys Leu Glu Asp Leu Glu Glu Gln Leu Asn His Leu Leu Leu Trp
      2330                2335                2340
Leu Ser Pro Ile Arg Asn Gln Leu Glu Ile Tyr Asn Gln Pro Asn
      2345                2350                2355
Gln Glu Gly Pro Phe Asp Val Lys Glu Thr Glu Ile Ala Val Gln
      2360                2365                2370
Ala Lys Gln Pro Asp Val Glu Glu Ile Leu Ser Lys Gly Gln His
      2375                2380                2385
Leu Tyr Lys Glu Lys Pro Ala Thr Gln Pro Val Lys Arg Lys Leu
      2390                2395                2400
Glu Asp Leu Ser Ser Glu Trp Lys Ala Val Asn Arg Leu Leu Gln
      2405                2410                2415
Glu Leu Arg Ala Lys Gln Pro Asp Leu Ala Pro Gly Leu Thr Thr
      2420                2425                2430
```

```
Ile Gly Ala Ser Pro Thr Gln Thr Val Thr Leu Val Thr Gln Pro
    2435                2440                2445

Val Val Thr Lys Glu Thr Ala Ile Ser Lys Leu Glu Met Pro Ser
    2450                2455                2460

Ser Leu Met Leu Glu Val Pro Ala Leu Ala Asp Phe Asn Arg Ala
    2465                2470                2475

Trp Thr Glu Leu Thr Asp Trp Leu Ser Leu Leu Asp Gln Val Ile
    2480                2485                2490

Lys Ser Gln Arg Val Met Val Gly Asp Leu Glu Asp Ile Asn Glu
    2495                2500                2505

Met Ile Ile Lys Gln Lys Ala Thr Met Gln Asp Leu Glu Gln Arg
    2510                2515                2520

Arg Pro Gln Leu Glu Glu Leu Ile Thr Ala Ala Gln Asn Leu Lys
    2525                2530                2535

Asn Lys Thr Ser Asn Gln Glu Ala Arg Thr Ile Ile Thr Asp Arg
    2540                2545                2550

Ile Glu Arg Ile Gln Asn Gln Trp Asp Glu Val Gln Glu His Leu
    2555                2560                2565

Gln Asn Arg Arg Gln Gln Leu Asn Glu Met Leu Lys Asp Ser Thr
    2570                2575                2580

Gln Trp Leu Glu Ala Lys Glu Ala Glu Gln Val Leu Gly Gln
    2585                2590                2595

Ala Arg Ala Lys Leu Glu Ser Trp Lys Glu Gly Pro Tyr Thr Val
    2600                2605                2610

Asp Ala Ile Gln Lys Lys Ile Thr Glu Thr Lys Gln Leu Ala Lys
    2615                2620                2625

Asp Leu Arg Gln Trp Gln Thr Asn Val Asp Val Ala Asn Asp Leu
    2630                2635                2640

Ala Leu Lys Leu Leu Arg Asp Tyr Ser Ala Asp Asp Thr Arg Lys
    2645                2650                2655

Val His Met Ile Thr Glu Asn Ile Asn Ala Ser Trp Arg Ser Ile
    2660                2665                2670

His Lys Arg Val Ser Glu Arg Glu Ala Ala Leu Glu Glu Thr His
    2675                2680                2685

Arg Leu Leu Gln Gln Phe Pro Leu Asp Leu Glu Lys Phe Leu Ala
    2690                2695                2700

Trp Leu Thr Glu Ala Glu Thr Thr Ala Asn Val Leu Gln Asp Ala
    2705                2710                2715

Thr Arg Lys Glu Arg Leu Leu Glu Asp Ser Lys Gly Val Lys Glu
    2720                2725                2730

Leu Met Lys Gln Trp Gln Asp Leu Gln Gly Glu Ile Glu Ala His
    2735                2740                2745

Thr Asp Val Tyr His Asn Leu Asp Glu Asn Ser Gln Lys Ile Leu
    2750                2755                2760

Arg Ser Leu Glu Gly Ser Asp Asp Ala Val Leu Leu Gln Arg Arg
    2765                2770                2775

Leu Asp Asn Met Asn Phe Lys Trp Ser Glu Leu Arg Lys Lys Ser
    2780                2785                2790

Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820
```

```
Lys Asp Asp Glu Leu Ser Arg Gln Ala Pro Ile Gly Gly Asp Phe
2825                2830                2835

Pro Ala Val Gln Lys Gln Asn Asp Val His Arg Ala Phe Lys Arg
2840                2845                2850

Glu Leu Lys Thr Lys Glu Pro Val Ile Met Ser Thr Leu Glu Thr
2855                2860                2865

Val Arg Ile Phe Leu Thr Glu Gln Pro Leu Glu Gly Leu Glu Lys
2870                2875                2880

Leu Tyr Gln Glu Pro Arg Glu Leu Pro Pro Glu Glu Arg Ala Gln
2885                2890                2895

Asn Val Thr Arg Leu Leu Arg Lys Gln Ala Glu Glu Val Asn Thr
2900                2905                2910

Glu Trp Glu Lys Leu Asn Leu His Ser Ala Asp Trp Gln Arg Lys
2915                2920                2925

Ile Asp Glu Thr Leu Glu Arg Leu Gln Glu Leu Gln Glu Ala Thr
2930                2935                2940

Asp Glu Leu Asp Leu Lys Leu Arg Gln Ala Glu Val Ile Lys Gly
2945                2950                2955

Ser Trp Gln Pro Val Gly Asp Leu Leu Ile Asp Ser Leu Gln Asp
2960                2965                2970

His Leu Glu Lys Val Lys Ala Leu Arg Gly Glu Ile Ala Pro Leu
2975                2980                2985

Lys Glu Asn Val Ser His Val Asn Asp Leu Ala Arg Gln Leu Thr
2990                2995                3000

Thr Leu Gly Ile Gln Leu Ser Pro Tyr Asn Leu Ser Thr Leu Glu
3005                3010                3015

Asp Leu Asn Thr Arg Trp Lys Leu Leu Gln Val Ala Val Glu Asp
3020                3025                3030

Arg Val Arg Gln Leu His Glu Ala His Arg Asp Phe Gly Pro Ala
3035                3040                3045

Ser Gln His Phe Leu Ser Thr Ser Val Gln Gly Pro Trp Glu Arg
3050                3055                3060

Ala Ile Ser Pro Asn Lys Val Pro Tyr Tyr Ile Asn His Glu Thr
3065                3070                3075

Gln Thr Thr Cys Trp Asp His Pro Lys Met Thr Glu Leu Tyr Gln
3080                3085                3090

Ser Leu Ala Asp Leu Asn Asn Val Arg Phe Ser Ala Tyr Arg Thr
3095                3100                3105

Ala Met Lys Leu Arg Arg Leu Gln Lys Ala Leu Cys Leu Asp Leu
3110                3115                3120

Leu Ser Leu Ser Ala Ala Cys Asp Ala Leu Asp Gln His Asn Leu
3125                3130                3135

Lys Gln Asn Asp Gln Pro Met Asp Ile Leu Gln Ile Ile Asn Cys
3140                3145                3150

Leu Thr Thr Ile Tyr Asp Arg Leu Glu Gln Glu His Asn Asn Leu
3155                3160                3165

Val Asn Val Pro Leu Cys Val Asp Met Cys Leu Asn Trp Leu Leu
3170                3175                3180

Asn Val Tyr Asp Thr Gly Arg Thr Gly Arg Ile Arg Val Leu Ser
3185                3190                3195

Phe Lys Thr Gly Ile Ile Ser Leu Cys Lys Ala His Leu Glu Asp
3200                3205                3210

Lys Tyr Arg Tyr Leu Phe Lys Gln Val Ala Ser Ser Thr Gly Phe
```

```
                3215                3220                3225
Cys Asp Gln Arg Arg Leu Gly Leu Leu Leu His Asp Ser Ile Gln
    3230                3235                3240

Ile Pro Arg Gln Leu Gly Glu Val Ala Ser Phe Gly Gly Ser Asn
    3245                3250                3255

Ile Glu Pro Ser Val Arg Ser Cys Phe Gln Phe Ala Asn Asn Lys
    3260                3265                3270

Pro Glu Ile Glu Ala Ala Leu Phe Leu Asp Trp Met Arg Leu Glu
    3275                3280                3285

Pro Gln Ser Met Val Trp Leu Pro Val Leu His Arg Val Ala Ala
    3290                3295                3300

Ala Glu Thr Ala Lys His Gln Ala Lys Cys Asn Ile Cys Lys Glu
    3305                3310                3315

Cys Pro Ile Ile Gly Phe Arg Tyr Arg Ser Leu Lys His Phe Asn
    3320                3325                3330

Tyr Asp Ile Cys Gln Ser Cys Phe Phe Ser Gly Arg Val Ala Lys
    3335                3340                3345

Gly His Lys Met His Tyr Pro Met Val Glu Tyr Cys Thr Pro Thr
    3350                3355                3360

Thr Ser Gly Glu Asp Val Arg Asp Phe Ala Lys Val Leu Lys Asn
    3365                3370                3375

Lys Phe Arg Thr Lys Arg Tyr Phe Ala Lys His Pro Arg Met Gly
    3380                3385                3390

Tyr Leu Pro Val Gln Thr Val Leu Glu Gly Asp Asn Met Glu Thr
    3395                3400                3405

Pro Val Thr Leu Ile Asn Phe Trp Pro Val Asp Ser Ala Pro Ala
    3410                3415                3420

Ser Ser Pro Gln Leu Ser His Asp Asp Thr His Ser Arg Ile Glu
    3425                3430                3435

His Tyr Ala Ser Arg Leu Ala Glu Met Glu Asn Ser Asn Gly Ser
    3440                3445                3450

Tyr Leu Asn Asp Ser Ile Ser Pro Asn Glu Ser Ile Asp Asp Glu
    3455                3460                3465

His Leu Leu Ile Gln His Tyr Cys Gln Ser Leu Asn Gln Asp Ser
    3470                3475                3480

Pro Leu Ser Gln Pro Arg Ser Pro Ala Gln Ile Leu Ile Ser Leu
    3485                3490                3495

Glu Ser Glu Glu Arg Gly Glu Leu Glu Arg Ile Leu Ala Asp Leu
    3500                3505                3510

Glu Glu Glu Asn Arg Asn Leu Gln Ala Glu Tyr Asp Arg Leu Lys
    3515                3520                3525

Gln Gln His Glu His Lys Gly Leu Ser Pro Leu Pro Ser Pro Pro
    3530                3535                3540

Glu Met Met Pro Thr Ser Pro Gln Ser Pro Arg Asp Ala Glu Leu
    3545                3550                3555

Ile Ala Glu Ala Lys Leu Leu Arg Gln His Lys Gly Arg Leu Glu
    3560                3565                3570

Ala Arg Met Gln Ile Leu Glu Asp His Asn Lys Gln Leu Glu Ser
    3575                3580                3585

Gln Leu His Arg Leu Arg Gln Leu Leu Glu Gln Pro Gln Ala Glu
    3590                3595                3600

Ala Lys Val Asn Gly Thr Thr Val Ser Ser Pro Ser Thr Ser Leu
    3605                3610                3615
```

```
Gln Arg  Ser Asp Ser Ser Gln  Pro Met Leu Leu Arg  Val Val Gly
    3620             3625                 3630

Ser Gln  Thr Ser Asp Ser Met  Gly Glu Glu Asp Leu  Leu Ser Pro
    3635             3640                 3645

Pro Gln  Asp Thr Ser Thr Gly  Leu Glu Glu Val Met  Glu Gln Leu
    3650             3655                 3660

Asn Asn  Ser Phe Pro Ser Ser  Arg Gly Arg Asn Thr  Pro Gly Lys
    3665             3670                 3675

Pro Met  Arg Glu Asp Thr Met
    3680             3685
```